(12) United States Patent
Cheung et al.

(10) Patent No.: US 10,316,093 B2
(45) Date of Patent: Jun. 11, 2019

(54) ANTIBODIES, COMPOSITIONS, AND USES

(71) Applicant: Memorial Sloan Kettering Cancer Center, New York, NY (US)

(72) Inventors: Nai-Kong V. Cheung, New York, NY (US); Mahiuddin Ahmed, Verona, NJ (US); Qi Zhao, Tseung Kwan (HK)

(73) Assignee: MEMORIAL SLOAN KETTERING CANCER CENTER, New York, NY (US)

(*) Notice: Subject to any disclaimer, the term of this patent is extended or adjusted under 35 U.S.C. 154(b) by 273 days.

(21) Appl. No.: 15/505,872

(22) PCT Filed: Aug. 26, 2015

(86) PCT No.: PCT/US2015/047013
§ 371 (c)(1),
(2) Date: Feb. 22, 2017

(87) PCT Pub. No.: WO2016/033225
PCT Pub. Date: Mar. 3, 2016

(65) Prior Publication Data
US 2017/0240637 A1    Aug. 24, 2017

Related U.S. Application Data

(60) Provisional application No. 62/042,457, filed on Aug. 27, 2014.

(51) Int. Cl.
*A61K 39/395* (2006.01)
*C07K 16/28* (2006.01)
*C07K 16/32* (2006.01)
*A61K 35/17* (2015.01)
*A61K 51/10* (2006.01)
*C12N 15/85* (2006.01)
*A61K 39/00* (2006.01)

(52) U.S. Cl.
CPC .......... *C07K 16/2827* (2013.01); *A61K 35/17* (2013.01); *A61K 51/1027* (2013.01); *C07K 16/2809* (2013.01); *C07K 16/32* (2013.01); *C12N 15/85* (2013.01); *A61K 2039/505* (2013.01); *A61K 2039/53* (2013.01); *A61K 2039/552* (2013.01); *C07K 2299/00* (2013.01); *C07K 2317/24* (2013.01); *C07K 2317/31* (2013.01); *C07K 2317/51* (2013.01); *C07K 2317/515* (2013.01); *C07K 2317/55* (2013.01); *C07K 2317/56* (2013.01); *C07K 2317/565* (2013.01); *C07K 2317/567* (2013.01); *C07K 2317/622* (2013.01); *C07K 2317/732* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 7,666,424 B2 | 2/2010 | Cheung et al. |
| 7,737,258 B2 | 6/2010 | Cheung |
| 8,501,471 B2 | 8/2013 | Cheung |
| 9,062,110 B2 | 6/2015 | Cheung |
| 9,963,509 B2 * | 5/2018 | DuBridge .......... C07K 16/2827 |
| 2010/0143245 A1 | 6/2010 | Cheung |

FOREIGN PATENT DOCUMENTS

WO    WO-2011/109400 A2    9/2011
WO    WO-2011/160119 A2    12/2011

OTHER PUBLICATIONS

Adams, P.D. et al., PHENIX: a comprehensive Python-based system for macromolecular structure solution, 66(Pt 2):213-221 (2010).
Ahmed, M. et al., Humanized Affinity-matured Monoclonal Antibody 8H9 Has Potent Antitumor Activity and Binds to FG Loop of Tumor Antigen B7—H3, J. Biol. Chem., 290(50):30018-29 (2015).
Alvarez, R.D. et al., A Phase 1 study of combined modality (90)Yttrium-CC49 intraperitoneal radioimmunotherapy for ovarian cancer, Clin Cancer Res, 8(9):2806-2811 (2002).
Bailey, S., The CCP4 suite: programs for protein crystallography, Acta Crystallogr D Biol Crystallogr, 50(Pt 4):760-763 (1994).
Balm, M. and Hammack, J., Leptomeningeal carcinomatosis. Presenting features and prognostic factors, Arch Neurol, 53(7):626-632 (1996).
Boorjian, S.A. et al., T-Cell Coregulatory Molecule Expression in Urothelial Cell Carcinoma: Clinicopathologic Correlations and Association With Survival, Clin Cancer Res, 14(15):4800-4808 (2008).
Brahmer, J.R. et al., Safety and Activity of Anti-PD-L1 Antibody in Patients with Advanced Cancer, N Engl J Med, 366(26):2455-2465 (2012).
Bruno, M.K. and Raizer, J., Leptomeningeal metastases from solid tumors (meningeal carcinomatosis), Cancer Treat Res, 125:31-52 (2005).
Calabro, L. et al., Expression and regulation of B7—H3 immunoregulatory receptor, in human mesothelial and mesothelioma cells: Immunotherapeutic implications, 226(10):2595-2600 (2011).
Castriconi, R. et al., Indentification of 4Ig-B7—H3 as a neuroblastoma-associated molecule that exerts a protective role from an NK cell-mediated lysis, PNAS, 101(34):12640-12645 (2004).

(Continued)

*Primary Examiner* — Misook Yu
*Assistant Examiner* — Meera Natarajan
(74) *Attorney, Agent, or Firm* — Choate, Hall & Stewart, LLP; Brenda Herschback Jarrell; Tracy L. Vrablik

(57) ABSTRACT

The present disclosure describes anti-B7H3 antibody agents and uses relating thereto. Among other things, the present disclosure demonstrates particular immunomodulatory effectiveness of certain such antibodies. The present disclosure further describes particularly high-affinity or otherwise useful antibodies and antibody agents based thereon, including particularly certain humanized and/or affinity matured versions of an 8H9 antibody. In some embodiments, provided antibody agents are useful, for example, in the treatment of cancer. In some embodiments, provided antibody agents are useful in relieving immunosuppression, for example mediated by B7H3-positive cells.

26 Claims, 22 Drawing Sheets
Specification includes a Sequence Listing.

(56) References Cited

OTHER PUBLICATIONS

Caussa, L. et al., Role of Palliative Radiotherapy in the Management of Metastatic Pediatric Neuroblastoma: A Restrospective Single-Institution Study, 79(1):214-219 (2011).

Chamberlain, M.C., Neoplastic meningitis, J Clin Oncol, 23(15):3605-3613 (2005).

Chao, M.P. et al., Anti-CD47 antibody synergizes with rituximab to promote phagocytosis and eradicate non-Hodgkin lymphoma, Cell, 142(5):699-713 (2010).

Chao, M.P. et al., Calreticulin is the dominant pro-phagocytic signal on multiple human cancers and is counterbalanced by CD47, Sci Transl Med, 2(63):63ra94 (2010).

Chao, M.P. et al., Therapeutic antibody targeting of CD47 eliminates human acute lymphoblastic leukemia, Cancer Res, 71(4):1374-1384 (2011).

Chapoval, A.I. et al., B7—H3: a costimulatory molecule for T cell activation and IFN-gamma production, Nat Immunol, 2(3):269-274 (2001).

Chen, R. et al., ZDOCK: an initial-stage protein-docking algorithm, Proteins, 52(1):80-87 (2003).

Cheung, N. et al., Anti-idiotypic antibody facilitates scFv chimeric immune receptor gene transduction and clonal expansion of human lymphocytes for tumor therapy, Hybrid Hybridom, 22:209-218 (2003).

Cheung, N.K. et al., Murine anti-GD2 monoclonal antibody 3F8 combined with granulocyte-macrophage colony-stimulating factor and 13-cis-retinoic acid in high-rish patients with stage 4 neuroblastoma in first remission, J Clin Oncol, 30(26):3264-3270 (2012).

Cheung, N.K.V. et al., Humanizing murine IgG3 anti-GD2 antibody m3F8 substantially improves antibody-dependent cell-mediated cytotoxicity while retaining targeting in vivo, Oncoimmunology, 1(4):477-486 (2012).

Crispen, P.L. et al., Tumor Cell and Tumor Vasculature Expression of B7—H3 Predict Survival in Clear Cell Renal Cell Carcinoma, Clin Cancer Res, 14(16):5150-5157 (2008).

Croog, V.J. et al., Whole Neuraxis Irradiation to Address Central Nervous System Relapse in High-Rish Neuroblastoma, Int J Radiat Oncol Biol Phys, 78(3):849-854 (2010).

Davson, H. and Segal, M.B., The return of the cerebrospinal fluid to the blood: the drainage mechanism, Physiology of the CSF and Blood Brain Barriers, Boca Raton, FL: CRC Press, 489-523 (1996).

Dunkel, I.J. et al., High dose chemotherapy with autologous bone marrow rescue for children with diffuse pontine brain stem tumors, J. Neurooncol., 37(1):67-73 (1998).

Eskander, R.N. and Tewari, K.S., Emerging treatment options for management of malignant ascites in patients with ovarian cancer, Int J Womens Health, 4:395-404 (2012).

Freilich, R.J. et al., Neuroimaging and cerebrospinal fluid cytology in the diagnosis of leptomeningeal metastasis, Ann Neurol, 38(1):51-57 (1995).

Gleissner, B. and Chamberlain, M.C., Neoplastic meningitis, Lancet Neurol, 5(5):443-452 (2006).

Godal, R. et al., NK cell killing of AML and ALL blasts by Killer-Immunoglobulin Receptor (KIR) negative NK cells after NKG2A and LIR-1 blockade, Biol Blood Marrow Transplant, 16(5):612-621 (2010).

Gregorio, A. et al., Small round blue cell tumours: diagnostic and prognostic usefulness of the expression of B7—H3 surface molecule, 53(1):73-80 (2008).

Grossman, S.A. and Moynihan, T.J., Neoplastic meningitis, Neurol Clin, 9(4):843-856 (1991).

Grossman, S.A. and Spence, A., NCCN clinical practice guidelines for carcinomatous/lymphomatous, Oncology, 13(11A):144-152 (1999).

Hofmeyer, K.A. et al., The contrasting role of B7—H3, Proc Natl Acad Sci USA, 105(30:10277-10278 (2008).

Holm-Nielson, P., Pathogenesis of ascites in peritoneal carcinomatosis, Acta Pathol Microbiol Scand, 33(1):10-21 (1953).

International Search Report for PCT/US2015/047013, 6 pages (dated Feb. 5, 2016).

Juhl, H. et al., Additive cytotoxicity of different monoclonal antibody-cobra venom factor conjugates for human neuroblastoma cells, Immunobiology, 197(5):444-459 (1997).

Kaplan, A.M. et al., Brainstem gliomas in children. A Children's Cancer Group review of 119 cases, Pediatr Neurosurg, 24(4):185-192 (1996).

Koppe, M.J. et al., Peritoneal carcinomatosis of colorectal origin: incidence and current treatment strategies, Ann Surg, 243(2):212-222 (2006).

Kramer, K et al., Radionecrosis in Children Treated with Conventional Radiation Therapy and Intrathecal Radioimmunotherapy for CNS Neuroblastoma: Is it a Concern?, Advances in Neuroblastoma Research: Information Book, abstract POC053, 249 (2014).

Kramer, K. et al, Radioimmunotherapy (RIT) of Cancer Metastatic to the Central Nervous System (CNS): Phase I study of Intrathecal 131I—8H9, American Association for Cancer Research LB-4 (Presentation), 23 slides (2007).

Kramer, K. et al., Compartmental intrathecal radioimmunotherapy: results for treatment for metastatic CNS neuroblastoma, J Neurooncol, 97(3):409-418 (2010).

Kramer, K. et al., Effective intrathecal radioimmunotherapy-based salvage regimen for metastatic CNS neuroblastoma (NB), Abstracts from the Thirteenth International Symposium on Pediatric Neuro-Oncology (ISPNO), 443-444 (2008).

Kramer, K. et al., Neuroblastoma metastatic to the central nervous system. The Memorial Sloan-kettering Cancer Center Experience and a Literature Review, Cancer, 91(8):1510-1519 (2001).

Kramer, K. et al., Phase I study of targeted radioimmunotherapy for leptomeningeal cancers using intra-Ommaya 131-I—3F8, J Clin Oncol, 25(34):5465-5470 (2007).

Kramer, K. et al., Recurrent Neuroblastoma Metastatic to the Central Nervous System: Is it curable?, Advances in Neuroblastoma Research: Information Book, abstract OR073, 138 (2014).

Laske, D.W. et al., Chronic interstitial infusion of protein to primate brain: determination of drug distribution and clearance with single-photon emission computerized tomograph imaging, J Neurosurg, 87(4):586-594 (1997).

Lemke, D. et al., Costimulatory protein 4IgB7H3 drives the malignant phenotype of glioblastoma by mediating immune escape and invasiveness, Clin. Cancer Res., 18(1):105-117(2012).

Littman, P. et al., Central nervous system (CNS) prophylaxis in children with low risk acute lymphoblastic leukemia (ALL), Int J Radiat Oncol Biol Phys, 13(10):1443-1449 (1987).

Loo, D. et al., Deveopment of an Fc-Enhanced Anti-B7—H3 Monoclonal Antibody With Potent Antitumor Activity, Clin Cancer Res, 18(14):3834-3845 (2012).

Loos, M. et al., Expression of the costimulatory molecule B7—H3 is associated with prolonged survival in human pancreatic cancer, BMC Cancer, 9:463(2009).

Luther, N. et al., Interstitial infusion of glioma-targeted recombinant immunotoxin 8H9scFv-PE38, Mol Cancer Ther, 9(4):1039-1046 (2010).

Luther, N. et al., Intraparenchymal and intratumoral interstitial infusion of anti-glioma monoclonal antibody 8H9, Neurosurgery, 62(6):1166-1174 (2008).

Luther, N. et al., The potential of theragnostic 124I—8H9 convection-enhanced delivery in diffuse intrinsic pontine glioma, Neuro Oncol, 16(6):800-806 (2014).

Maher, E.A. et al., Brain metastasis: Opportunities in basic and translational research, Cancer Research, 69(15):6015-6020 (2009).

Majeti, R. et al., CD47 is an adverse prognostic factor and therapeutic antibody target on human acute myeloid leukemia stem cells, Cell, 138(2):286-299 (2009).

McCoy, A.J. et al., Phaser crystallographic software, J Appl Crystallogr, 40(Pt 4):658-674 (2007).

Mellman, I. et al., Cancer immunotherapy comes of age, Nature, 480(7378):480-489 (2011).

Modak, MJ et al., Intraperitoneal radioimmunotherapy (RIT) for desmoplastic small round cell tumor (DSRCT): Initial results from a phase I trial, ASCO Annual Meeting, J. Clin. Oncol., Abstract 3033 (2013).

(56) References Cited

OTHER PUBLICATIONS

Modak, S. et al., Monoclonal Antibody 8H9 Targets a Novel Cell Surface Antigen Expressed by a Wide Spectrum of Human Solid Tumors, Cancer Research, 61:4048-4054 (2001).
Modak, S. et al., Radioimmunotargeting of human rhabdomyosarcoma using monoclonal antibody 8H9, Cancer Biotherapy and Rediopharmaceuticals, 20(5):534-546 (2005).
Morrison, P.F. et al., High-flow microinfusion: tissue penetration and pharmacodynamics, Am J Physiol, 266(1 Pt 2):R292-305 (1994).
NCI Protocol ID 09-090 NCT01099644.
NCT0150291 Clinical Trial as Described on Clinicaltrials.gov on Aug. 21, 2014.
Occhiogrosso, G. et al., Prolonged convection-enhanced delivery into the rat brainstem, Neurosurgery, 52(2):388-393 (2003).
Onda, M. et al., In vitro and in vivo cytotoxic activities of recombinant immunotoxin 8H9(Fv)-PE38 against breast cancer, osteosarcoma, and neuroblastoma, Cancer Res., 64(4):1419-24 (2004).
Posner, J.B., Neurologic Complications of Cancer, Comtemporary Neurology Series, Philadelphia, F.A. Davis Company (1995).
Reardon, D.A. et al., A pilot study:131I-antitenascin monoclonal antibody 81c6 to deliver a 44-Gy resection cavity boost, Neuro Oncol, 10(2):182-189 (2008).
Reardon, D.A. et al., Salvage radioimmunotherapy with murine iodine-131-labeled antitenascin monoclonal antibody 81C6 for patients with recurrent primary and metastatic malignant brain tumors: phase II study results, J Clin Oncol, 24(1):115-122 (2006).
Rocchia, W. et al., Rapid grid-based construction of the molecular surface and the use of induced surface charge to calculate reaction field energies: applications to the molecular systems and geometric objects, J Comput Chem, 23(1):128-137 (2002).
Romagne, F. et al., Preclinical characterization of 1-7F9, a novel human anti-KIR receptor therapeutic antibody that augments natural killer-mediated killing of tumor cells, Blood, 114(13):2667-2677 (2009).
Roth, T.J. et al., B7—H3 Ligand Expression by Prostate Cancer: A Novel Marker of Prognosis and Potential Target for Therapy, Cancer Research, 67(16):7893-7900 (2007).
Sadeghi, B. et al., Peritoneal carcinomatosis from non-gynecologic malignancies: results of the EVOCAPE 1 multicentric prospective study, Cancer, 88(2):358-363 (2000).
Saif, M.W. et al., Management of ascites due to gastrointestinal malignancy, Ann Saudi Med, 29(5):369-377 (2009).
Sanchez, R. and Sali, A., Evaluation of comparative protein structure modeling by MODELLER-3, Proteins, Suppl 1:50-58 (1997).
Sangisetty, S.L. and Miner, T.J., Malignang ascites: A review of prognostic factors, pathophysiology and therapeutic measures, World J Gastrointest Surg, 4(4):87-95 (2012).
Smith, D.H. et al., Protein accumulation in traumatic brain injury, Neuromolecular Med, 4(1-2):59-72 (2003).
Spector, R. and Mock, D.M., Biotin transport and metabolism in the central nervous system, Neurochem Res, 13(3):213-219 (1988).
Steinberger, P. et al., Molecular characterization of human 4Ig-B7—H3, a member of the B7 family with four Ig-like domains, J Immunol, 172(4):2352-2359 (2004).
Sugarbaker, P.H. et al., Prospective morbidity and mortality assessment of cytoreductive surgery plus perioperative intraperitoneal chemotherapy to treat peritoneal dissemination of appendiceal mucinous malignancy, Ann Surg Oncol, 13(5):635-644 (2006).
Suh, W.L. et al., The B7 family member of B7—H3 preferentially down-regulates T helper type 1-mediated immune responses, Nat Immunol, 4(9):899-906 (2003).
Sun, M. et al., Characterization of Mouse and Human B7—H3 Genes, J Immunol, 168(12):6294-6297 (2002).
Sun, X. et al., Mouse B7—H3 induces antitumor immunity, Gene Therapy, 10:1728-1734 (2003).
Tarek, N. et al., Unlicense NK cells target neuroblastoma following anti-GD2 antibody treatment, J Clin Invest, 122(9):3260-3270 (2012).
Topalian, S.L. et al, Safety, Activity, and Immune Correlates of Anti-PD-1 Antibody in Cancer, N Engl J Med, 366(26):2443-2454 (2012).
Topalian, S.L. et al., Targeting the Pd—1/B7—HI(Pd—Li) pathway to activate anti-tumor immunity, Curr Opin Immunol, 24(2):207-12 (2012).
Verheijen, R.H. et al., Phase III trial of intraperitoneal therapy with yttrium-90-labeled HMFG1 murine monoclonal antibody in patients with epithelial ovarian cancer after a surgically defined complete remission, J Clin Oncol, 24(4):571-578 (2006).
Vigdorovich, V. et al., Structure and T-cell inhibition properties of B7 family member, B7—H3, Structure, 21(5):707-717 (2013).
Wang, L. et al., B7—H3 is Overexpressed in Patients Suffering Osteosarcoma and Associated with Tumor Aggressiveness and Metastasis, PLoS One, 8(8):e70689 (2013).
Wasserstrom, W.R. et al., Diagnosis and treatment of leptomeningeal metastases from solid tumors: experience with 90 patients, Cancer, 49(4):759-772 (1982).
Wilcox, R.A. et al., The B7 Homologues and their Receptors in Hematologic Malignancies, European Journal of Haematology, 88(6):465-475 (2012).
Willingham, S.B. et al., The CD47-signal regulatory protein alpha (SIRPa) interaction is a therapeutic target for human solid tumors, Proc Natl Acad Sci USA, 109(17):6662-6667 (2012).
Written Opinion for PCT/US2015/047013, 9 pages (dated Feb. 5, 2016).
Wu, C.P. et al., Relationship between co-stimulatory molecule B7—H3 expression and gastric carcinoma histology prognosis, World J Gastroenterol, 12(3):457-459 (2006).
Xu, H. et al., MicroRNA miR-29 modulates expression of immunoinhibitory molecule B7—H3: Potential implications for immune based therapy of human solid tumors, Cancer Res, 69(15):6275-6281 (2009).
Yamato, I. et al., Clinical importance of B7—H3 expression in human pancreatic cancer, Br J Cancer, 101(10):1709-1716 (2009).
Zalutsky, M.R. et al., Clinical Experience with alpha-Particle-Emitting 211At: Treatment of Recurrent Brain Tumor Patients with 211At-Labeled Chimeric Antitenascin Monoclonal Antibody 81C6, J Nucl Med, 49(1):30-38 (2008).
Zang, X. et al., Tumor associated endothelial expression of B7—H3 predicts survival in ovarian carcinomas, Mod Pathol, 23(8):1104-1112 (2010).
Zhang, X. et al., B7—H3 and B7x are highly expressed in human prostate cancer and associated with disease spread and poor outcome, Proc Natl Acad Sci USA, 104(49):19458-19463 (2007).
Zhao, Q. et al., Human Monoclonal Antibody Fragments Binding to Insulin-like Growth Factors 1 and 2 with Picomolar Affinity, Mol Cancer Ther, 10(9):1677-1685 (2011).
Zhao, X.W. et al., CD47-signal regulatory protein-alpha (SIRPalpha) interactions form a barrier for antibody-mediated tumor cell destruction, Proc Natl Acad Sci USA, 108(45):18342-18347 (2011).
Zhou, Z. et al., B7—H3, a potential therapeutic target, is expressed in diffuse intrinsic pontine glioma, J Neurooncol, 111(3):257-264 (2013).

* cited by examiner

SEQUENCE LISTING

<160> NUMBER OF SEQ ID NOS: 105

<210> SEQ ID NO 1
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Arg Thr Val Ala Ala

```
                    100                 105                 110
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Ile Ser Asp Tyr
                20                  25                  30

Leu His Trp Tyr Gln Gln Lys Pro Gly Gln Ala Pro Arg Leu Leu Ile
            35                  40                  45

Lys Tyr Ala Ser Gln Ser Ile Ser Gly Ile Pro Ala Arg Phe Ser Gly
        50                  55                  60

Ser Gly Ser Gly Thr Glu Phe Thr Leu Thr Ile Ser Ser Val Gln Pro
65                  70                  75                  80

Glu Asp Val Gly Val Tyr Tyr Cys Gln Asn Gly His Ser Phe Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 214
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ala Arg Phe Ser Gly
50                  55                  60

Ser Gly Ser Gly Thr Glu Phe Thr Leu Thr Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Ile Val Met Thr Gln Ser Pro Ala Thr Leu Ser Val Ser Pro Gly
1               5                   10                  15

Glu Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ala Arg Phe Ser Gly
50                  55                  60

Ser Gly Ser Gly Ser Glu Phe Thr Leu Thr Ile Asn Ser Val Glu Pro
65                  70                  75                  80

Glu Asp Val Gly Val Tyr Tyr Cys Gln Asn Gly His Ser Phe Pro Leu
                85                  90                  95
```

```
Thr Phe Gly Gln Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Ile Ser Asp Tyr
            20                  25                  30

Leu Tyr Trp Tyr Gln Gln Lys Ser His Glu Ser Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Ser Glu Phe Thr Leu Thr Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Gln Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
```

<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Ile Ser Asp Tyr
            20                  25                  30

Leu His Trp Tyr Gln Gln Lys Ser His Gln Ala Pro Arg Leu Leu Ile
        35                  40                  45

Lys Tyr Ala Ser Gln Ser Ile Ser Gly Ile Pro Ala Arg Phe Ser Gly
50                  55                  60

Ser Gly Ser Gly Ser Glu Phe Thr Leu Thr Ile Ser Ser Leu Gln Pro
65                  70                  75                  80

Glu Asp Phe Gly Val Tyr Tyr Cys Gln Asn Gly His Ser Phe Pro Leu
                85                  90                  95

Thr Phe Gly Gln Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 7
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

```
Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Ile Ser Asp Tyr
            20                  25                  30

Leu Tyr Trp Tyr Gln Gln Lys Ser His Gln Ala Pro Arg Leu Leu Ile
        35                  40                  45

Lys Tyr Ala Ser Gln Ser Ile Ser Gly Ile Pro Ala Arg Phe Ser Gly
50                  55                  60

Ser Gly Ser Gly Ser Glu Phe Thr Leu Thr Ile Ser Ser Leu Gln Pro
65                  70                  75                  80

Glu Asp Phe Gly Val Tyr Tyr Cys Gln Asn Gly His Ser Phe Pro Leu
                85                  90                  95
```

```
Thr Phe Gly Gln Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 8
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Val Met Thr Gln Ser Pro Ala Thr Leu Ser Val Thr Pro Gly
1               5                   10                  15

Asp Arg Val Thr Leu Ser Cys Arg Ala Ser Gln Ser Ile Ser Asp Tyr
            20                  25                  30

Leu Tyr Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 9
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9
```

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Gln Thr Thr Ala Thr Trp Phe Ala Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

```
Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445
```

<210> SEQ ID NO 10
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Asn Tyr
                20                  25                  30

Asp Ile Asn Trp Val Arg Gln Ala Pro Gly Gln Gly Leu Glu Trp Ile
                35                  40                  45

Gly Trp Ile Phe Pro Gly Asp Gly Ser Thr Gln Tyr Asn Glu Lys Phe
            50                  55                  60

Lys Gly Lys Ala Thr Leu Thr Thr Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gln Thr Thr Ala Thr Trp Phe Ala Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Arg Val Glu Pro Lys Ser Cys Asp Lys Thr
                210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285
```

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 11
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Asn Tyr
            20                  25                  30

Asp Ile Asn Trp Val Arg Gln Ala Pro Gly Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Thr Ser Thr Ala Tyr
65                  70                  75                  80

Met Glu Leu Ser Arg Leu Thr Ser Glu Asp Thr Ala Val Tyr Phe Cys
                85                  90                  95

Ala Arg Gln Thr Thr Ala Thr Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser 195                 200                 205
Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 12
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Asn Tyr
                20                  25                  30

Asp Ile Asn Trp Val Arg Gln Arg Pro Glu Gln Gly Leu Glu Trp Ile
            35                  40                  45

Gly Trp Ile Phe Pro Gly Asp Gly Ser Thr Gln Tyr Asn Glu Lys Phe
        50                  55                  60

Lys Gly Lys Ala Thr Leu Thr Thr Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gln Thr Thr Ala Thr Trp Phe Ala Tyr Trp Gly Gln Gly Thr
            100                 105                 110

```
Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
    195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
    435                 440                 445

<210> SEQ ID NO 13
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
            20                  25                  30
```

-continued

Asp Ile Asn Trp Val Arg Gln Arg Pro Gly Gln Gly Leu Glu Trp Ile
         35                  40                  45

Gly Trp Ile Phe Pro Gly Asp Ser Thr Gln Tyr Asn Glu Lys Phe
     50                  55                  60

Lys Gly Lys Ala Thr Leu Thr Thr Asp Thr Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Gln Thr Thr Gly Thr Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

-continued

<210> SEQ ID NO 14
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Arg Val Thr Met Thr Thr Asp Thr Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Arg Gln Thr Thr Ala Thr Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

```
Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 15
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Ala Glu Val Val Lys Pro Gly Ala
1               5                   10                  15

Ser Val Lys Val Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
        35                  40                  45

Gly Trp Ile Phe Pro Gly Asp Asp Ser Thr Gln Tyr Asn Glu Lys Phe
    50                  55                  60

Lys Gly Arg Val Thr Met Thr Thr Asp Thr Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Arg Gln Thr Thr Gly Thr Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
```

```
                275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
            355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 16
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Gln Ser Gly Ala Glu Leu Val Lys Pro Gly Ala
1               5                   10                  15
Ser Val Lys Leu Ser Cys Lys Thr Ser Gly Tyr Thr Phe Thr Asn Tyr
            20                  25                  30
Asp Ile Asn Trp Val Arg Gln Arg Pro Gly Gln Gly Leu Glu Trp Ile
        35                  40                  45
Gly Trp Ile Phe Pro Gly Asp Asp Ser Thr Gln Tyr Asn Glu Lys Phe
    50                  55                  60
Lys Gly Lys Ala Thr Leu Thr Thr Asp Thr Ser Ser Ser Thr Ala Tyr
65                  70                  75                  80
Met Gln Leu Ser Arg Leu Thr Ser Glu Asp Ser Ala Val Tyr Phe Cys
                85                  90                  95
Ala Arg Gln Thr Thr Gly Thr Trp Phe Ala Tyr Trp Gly Gln Gly Thr
            100                 105                 110
Leu Val Thr Val Ser Ala Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
```

```
Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 17
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Asn Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gln Thr Thr Ala Thr Trp Phe Ala Tyr Trp Gly Gln Gly Thr
            100                 105                 110
```

```
Leu Val Thr Val Ser Ser Gly Gly Gly Gly Ser Gly Gly Gly Gly Ser
            115                 120                 125

Gly Gly Gly Gly Ser Glu Ile Val Met Thr Gln Ser Pro Ala Thr Leu
    130                 135                 140

Ser Val Ser Pro Gly Glu Arg Val Ser Leu Ser Cys Arg Ala Ser Gln
145                 150                 155                 160

Ser Ile Ser Asp Tyr Leu His Trp Tyr Gln Gln Lys Ser His Glu Ser
                165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser Gly Ser Glu Phe Thr Leu Thr Ile
            195                 200                 205

Asn Ser Val Glu Pro Glu Asp Val Gly Val Tyr Tyr Cys Gln Asn Gly
            210                 215                 220

His Ser Phe Pro Leu Thr Phe Gly Gln Gly Thr Lys Leu Glu Leu Lys
225                 230                 235                 240

Arg

<210> SEQ ID NO 18
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
            35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gln Thr Thr Ala Thr Trp Phe Ala Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Glu Ile Val Met Thr Gln Ser Pro Ala Thr Leu
    130                 135                 140

Ser Val Ser Pro Gly Glu Arg Val Thr Leu Ser Cys Arg Ala Ser Gln
145                 150                 155                 160

Ser Ile Ser Asp Tyr Leu Tyr Trp Tyr Gln Gln Lys Ser His Glu Ser
                165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser Gly Ser Glu Phe Thr Leu Thr Ile
            195                 200                 205

Asn Ser Val Glu Pro Glu Asp Val Gly Val Tyr Tyr Cys Gln Asn Gly
            210                 215                 220
```

His Ser Phe Pro Leu Thr Phe Gly Gln Gly Thr Lys Leu Glu Leu Lys
225                 230                 235                 240

Arg

<210> SEQ ID NO 19
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Gln Ser Gly Ala Glu Val Val Lys Pro Gly Ala
1               5                   10                  15

Ser Cys Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gln Thr Thr Ala Thr Trp Phe Ala Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Val Gly Ser Glu Ile Val Met Thr Gln Ser Pro Ala Thr Leu
    130                 135                 140

Ser Val Ser Pro Gly Glu Arg Val Thr Leu Ser Cys Arg Ala Ser Gln
145                 150                 155                 160

Ser Ile Gly Asp Tyr Leu Tyr Trp Tyr Gln Gln Lys Ser His Glu Ser
                165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser Gly Ser Glu Phe Thr Leu Thr Ile
        195                 200                 205

Asn Ser Val Glu Pro Glu Asp Val Gly Val Tyr Tyr Cys Gln Asn Gly
    210                 215                 220

His Ser Phe Pro Leu Thr Phe Gly Gln Gly Thr Lys Leu Glu Leu Lys
225                 230                 235                 240

Arg

<210> SEQ ID NO 20
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr

```
                    20                  25                  30
Asp Ile Asn Trp Val Arg Gln Arg Pro Gly Gln Gly Leu Glu Trp Val
            35                  40                  45
Gly Trp Ile Phe Pro Gly Asp Gly Ser Thr Gln Tyr Asn Glu Lys Phe
        50                  55                  60
Lys Gly Lys Ala Thr Leu Thr Thr Asp Thr Ser Thr Ser Thr Ala Tyr
65                  70                  75                  80
Met Glu Leu Ser Ser Leu Arg Ser Glu Asp Thr Ala Val Tyr Phe Cys
                85                  90                  95
Ala Arg Gln Thr Thr Ser Thr Trp Phe Ala Tyr Trp Gly Gln Gly Thr
            100                 105                 110
Leu Val Thr Val Ser Ser Gly Gly Gly Gly Ser Gly Gly Gly Gly Ser
        115                 120                 125
Gly Gly Gly Gly Ser Glu Ile Val Met Thr Gln Ser Pro Ala Thr Leu
    130                 135                 140
Ser Val Ser Pro Gly Glu Arg Val Thr Leu Ser Cys Arg Ala Ser Gln
145                 150                 155                 160
Pro Ile Ser Asp Tyr Leu Tyr Trp Tyr Gln Gln Lys Ser His Glu Ser
                165                 170                 175
Pro Arg Leu Leu Ile Lys Tyr Ala Ser Gln Ser Ile Ser Gly Ile Pro
            180                 185                 190
Ala Arg Phe Ser Gly Ser Gly Ser Gly Ser Glu Phe Thr Leu Thr Ile
        195                 200                 205
Asn Ser Val Glu Pro Glu Asp Val Gly Val Tyr Tyr Cys Gln Asn Gly
    210                 215                 220
Tyr Ser Phe Pro Leu Thr Phe Gly Gln Gly Thr Lys Leu Glu Leu Lys
225                 230                 235                 240
Arg

<210> SEQ ID NO 21
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Val Lys Pro Gly Ala
1               5                   10                  15
Ser Val Lys Leu Ser Cys Lys Thr Ser Gly Tyr Thr Phe Thr Asn Tyr
            20                  25                  30
Asp Ile Asn Trp Val Arg Gln Arg Pro Gly Gln Gly Leu Glu Trp Ile
        35                  40                  45
Gly Trp Ile Phe Pro Gly Asp Asp Ser Thr Gln Tyr Asn Glu Lys Phe
    50                  55                  60
Lys Gly Lys Ala Thr Leu Thr Thr Asp Thr Ser Thr Ser Thr Ala Tyr
65                  70                  75                  80
Met Glu Leu Ser Ser Leu Arg Pro Glu Asp Thr Ala Val Tyr Phe Cys
                85                  90                  95
Ala Arg Gln Thr Thr Gly Thr Trp Phe Ala Tyr Trp Gly Gln Gly Thr
            100                 105                 110
Leu Val Thr Val Ser Ser Gly Gly Gly Gly Ser Gly Gly Gly Gly Ser
        115                 120                 125
Gly Gly Gly Gly Ser Glu Ile Val Met Thr Gln Ser Pro Ala Thr Leu
```

```
                130                 135                 140
Ser Val Ser Pro Gly Glu Arg Val Thr Leu Ser Cys Arg Ala Ser Gln
145                 150                 155                 160

Ser Ile Ser Asp Tyr Leu Tyr Trp Tyr Gln Gln Lys Ser His Glu Ser
                165                 170                 175

Pro Arg Leu Leu Ile Lys Tyr Ala Ser Gln Ser Ile Pro Gly Ile Pro
                180                 185                 190

Ala Arg Phe Ser Gly Ser Gly Ser Gly Ser Glu Phe Thr Leu Thr Ile
                195                 200                 205

Asn Ser Val Glu Pro Glu Asp Val Gly Val Tyr Tyr Cys Gln Asn Gly
                210                 215                 220

His Ser Phe Pro Leu Thr Phe Gly Gln Gly Thr Lys Leu Glu Leu Lys
225                 230                 235                 240

Arg

<210> SEQ ID NO 22
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
                20                  25                  30

Asp Ile Asn Trp Val Arg Gln Arg Pro Gly Gln Gly Leu Glu Trp Ile
                35                  40                  45

Gly Trp Ile Phe Pro Gly Asp Gly Ser Thr Gln Tyr Asn Glu Lys Phe
            50                  55                  60

Lys Gly Lys Ala Thr Leu Thr Thr Asp Thr Ser Thr Ser Thr Ala Tyr
65                  70                  75                  80

Met Glu Leu Ser Ser Leu Gly Ser Glu Asp Thr Ala Val Tyr Phe Cys
                85                  90                  95

Thr Arg Gln Thr Thr Ala Thr Trp Phe Ala Tyr Trp Gly Gln Gly Thr
                100                 105                 110

Leu Val Thr Val Ser Ser Gly Gly Gly Ser Gly Gly Gly Gly Ser
                115                 120                 125

Ser Gly Gly Gly Ser Glu Ile Val Met Thr Gln Ser Pro Ala Thr Leu
            130                 135                 140

Ser Val Ser Pro Gly Glu Arg Val Thr Leu Ser Cys Arg Ala Ser Gln
145                 150                 155                 160

Ser Ile Gly Asp Tyr Leu Tyr Trp Tyr Gln Gln Lys Ser His Glu Ser
                165                 170                 175

Pro Arg Leu Leu Ile Lys Tyr Ala Ser Gln Ser Ile Ser Gly Ile Pro
                180                 185                 190

Ala Arg Phe Ser Gly Ser Gly Ser Gly Ser Glu Phe Thr Leu Thr Ile
                195                 200                 205

Asn Ser Val Glu Pro Glu Asp Val Gly Val Tyr Tyr Cys Gln Asn Gly
                210                 215                 220

His Ser Phe Pro Leu Thr Phe Gly Gln Gly Thr Lys Leu Glu Leu Lys
225                 230                 235                 240

Arg
```

<210> SEQ ID NO 23
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Thr Ser Thr Ala Tyr
65                  70                  75                  80

Leu Glu Leu Ser Ser Leu Gly Ser Glu Asp Thr Ala Val Tyr Phe Cys
                85                  90                  95

Ala Arg Gln Thr Thr Gly Thr Trp Phe Ala Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Met Thr Gln Ser Pro Ala Thr Leu
    130                 135                 140

Ser Val Ser Pro Gly Glu Arg Val Thr Leu Ser Cys Arg Ala Ser Gln
145                 150                 155                 160

Ser Ile Ser Asp Tyr Leu Tyr Trp Tyr Gln Gln Lys Ser His Glu Ser
                165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser Gly Ser Glu Phe Thr Leu Thr Ile
        195                 200                 205

Asn Ser Val Glu Pro Glu Asp Val Gly Val Tyr Tyr Cys Gln Asn Gly
    210                 215                 220

His Ser Phe Pro Leu Thr Phe Gly Gln Gly Thr Lys Leu Glu Leu Lys
225                 230                 235                 240

Arg

<210> SEQ ID NO 24
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Val Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
        35                  40                  45

```
Gly Trp Ile Phe Pro Gly Asp Ser Thr Gln Tyr Asn Glu Lys Phe
 50                  55                  60

Lys Gly Lys Ala Thr Leu Thr Thr Asp Thr Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Gln Thr Thr Gly Thr Trp Phe Ala Tyr Trp Gly Gln Gly Thr
                100                 105                 110

Leu Val Thr Val Ser Ser Gly Gly Gly Ser Gly Gly Gly Gly Ser
                115                 120                 125

Gly Gly Gly Gly Ser Glu Ile Val Met Thr Gln Ser Pro Ala Thr Leu
130                 135                 140

Ser Val Ser Pro Gly Glu Arg Val Thr Leu Ser Cys Arg Ala Ser Gln
145                 150                 155                 160

Ser Ile Ser Asp Tyr Leu Tyr Trp Tyr Gln Gln Lys Ser His Glu Ser
                165                 170                 175

Pro Arg Leu Leu Ile Lys Tyr Ala Ser Gln Ser Ile Ser Gly Ile Pro
                180                 185                 190

Ala Arg Phe Ser Gly Ser Gly Ser Gly Ser Glu Phe Thr Leu Thr Ile
                195                 200                 205

Asn Ser Val Glu Pro Glu Asp Val Gly Val Tyr Tyr Cys Gln Asn Gly
210                 215                 220

His Ser Phe Pro Leu Thr Phe Gly Gln Gly Thr Lys Leu Glu Leu Lys
225                 230                 235                 240

Arg

<210> SEQ ID NO 25
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Gln Ser Gly Ala Glu Val Val Lys Pro Gly Ala
 1               5                  10                  15

Ser Val Lys Val Ser Cys Lys Ala Ser Gly Tyr Thr Phe Thr Asn Tyr
                 20                  25                  30

Asp Ile Asn Trp Val Arg Gln Arg Pro Glu Gln Gly Leu Glu Trp Ile
             35                  40                  45

Gly Trp Ile Phe Pro Gly Asp Gly Ser Thr Gln Tyr Asn Glu Lys Phe
 50                  55                  60

Lys Gly Arg Val Thr Met Thr Thr Asp Thr Ser Thr Ser Thr Val Tyr
 65                  70                  75                  80

Met Glu Leu Ser Ser Leu Arg Ser Glu Asp Thr Ala Val Tyr Phe Cys
                 85                  90                  95

Ala Arg Gln Thr Thr Ala Thr Trp Phe Ala Tyr Trp Gly Gln Gly Thr
                100                 105                 110

Leu Val Thr Val Ser Ser Gly Gly Gly Gly Ser Gly Gly Gly Gly Ser
                115                 120                 125

Gly Gly Gly Gly Ser Glu Ile Val Met Thr Gln Ser Pro Ala Thr Leu
130                 135                 140

Ser Val Ser Pro Gly Glu Arg Val Thr Leu Ser Cys Arg Ala Ser Gln
145                 150                 155                 160
```

```
Ser Ile Ser Asp Tyr Leu His Trp Tyr Gln Gln Lys Ser His Gln Ala
            165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser Gly Ser Glu Phe Thr Leu Thr Ile
            195                 200                 205

Ser Ser Leu Gln Pro Glu Asp Phe Gly Val Tyr Tyr Cys Gln Asn Gly
            210                 215                 220

His Ser Phe Pro Leu Thr Phe Gly Gln Gly Thr Lys Leu Glu Leu Lys
225                 230                 235                 240

Arg

<210> SEQ ID NO 26
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Gln Ser Gly Ala Glu Val Val Lys Pro Gly Ala
1               5                   10                  15

Ser Val Lys Val Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
            35                  40                  45

Gly Trp Ile Phe Pro Gly Asp Asp Ser Thr Gln Tyr Asn Glu Lys Phe
        50                  55                  60

Lys Gly Arg Val Thr Met Thr Thr Asp Thr Ser Thr Ser Thr Val Tyr
65                  70                  75                  80

Met Glu Leu Ser Ser Leu Arg Ser Glu Asp Thr Ala Val Tyr Phe Cys
            85                  90                  95

Ala Arg Gln Thr Thr Gly Thr Trp Phe Ala Tyr Trp Gly Gln Gly Thr
            100                 105                 110

Leu Val Thr Val Ser Ser Gly Gly Gly Ser Gly Gly Gly Gly Ser
            115                 120                 125

Gly Gly Gly Gly Ser Glu Ile Val Met Thr Gln Ser Pro Ala Thr Leu
        130                 135                 140

Ser Val Ser Pro Gly Glu Arg Val Thr Leu Ser Cys Arg Ala Ser Gln
145                 150                 155                 160

Ser Ile Ser Asp Tyr Leu Tyr Trp Tyr Gln Gln Lys Ser His Gln Ala
            165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser Gly Ser Glu Phe Thr Leu Thr Ile
            195                 200                 205

Ser Ser Leu Gln Pro Glu Asp Phe Gly Val Tyr Tyr Cys Gln Asn Gly
            210                 215                 220

His Ser Phe Pro Leu Thr Phe Gly Gln Gly Thr Lys Leu Glu Leu Lys
225                 230                 235                 240

Arg

<210> SEQ ID NO 27
<211> LENGTH: 241
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 27

```
Gln Val Gln Leu Gln Gln Ser Gly Ala Glu Leu Val Lys Pro Gly Ala
1               5                   10                  15

Ser Val Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
        35                  40                  45

Gly Trp Ile Phe Pro Gly Asp Asp Ser Thr Gln Tyr Asn Glu Lys Phe
    50                  55                  60

Lys Gly Lys Ala Thr Leu Thr Thr Asp Thr Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Gln Thr Thr Gly Thr Trp Phe Ala Tyr Trp Gly Gln Gly Thr
            100                 105                 110

Leu Val Thr Val Ser Ala Gly Gly Gly Ser Gly Gly Gly Gly Ser
            115                 120                 125

Gly Gly Gly Gly Ser Asp Ile Val Met Thr Gln Ser Pro Ala Thr Leu
130                 135                 140

Ser Val Thr Pro Gly Asp Arg Val Thr Leu Ser Cys Arg Ala Ser Gln
145                 150                 155                 160

Ser Ile Ser Asp Tyr Leu Tyr Trp Tyr Gln Gln Lys Ser His Glu Ser
                165                 170                 175

Pro Arg Leu Leu Ile Lys Tyr Ala Ser Gln Ser Ile Ser Gly Ile Pro
            180                 185                 190

Ser Arg Phe Ser Gly Ser Gly Ser Gly Ser Asp Phe Thr Leu Ser Ile
        195                 200                 205

Asn Ser Val Glu Pro Glu Asp Val Gly Val Tyr Tyr Cys Gln Asn Gly
    210                 215                 220

His Ser Phe Pro Leu Thr Phe Gly Ala Gly Thr Lys Leu Glu Leu Lys
225                 230                 235                 240

Arg
```

<210> SEQ ID NO 28
<211> LENGTH: 256
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Gly Gly Gly Gly Ser Gly Gly Gly Gly Ser Gly Gly Gly Gly Ser Gln
1               5                   10                  15

Val Gln Leu Val Gln Ser Gly Gly Val Val Gln Pro Gly Arg Ser
            20                  25                  30

Leu Arg Leu Ser Cys Lys Ala Ser Gly Tyr Thr Phe Thr Arg Tyr Thr
        35                  40                  45

Met His Trp Val Arg Gln Ala Pro Gly Lys Gly Leu Glu Trp Ile Gly
    50                  55                  60

Tyr Ile Asn Pro Ser Arg Gly Tyr Thr Asn Tyr Asn Gln Lys Phe Lys
65                  70                  75                  80
```

Asp Arg Phe Thr Ile Ser Arg Asp Asn Ser Lys Asn Thr Ala Phe Leu
                85                  90                  95

Gln Met Asp Ser Leu Arg Pro Glu Asp Thr Gly Val Tyr Phe Cys Ala
            100                 105                 110

Arg Tyr Tyr Asp Asp His Tyr Cys Leu Asp Tyr Trp Gly Gln Gly Thr
        115                 120                 125

Pro Val Thr Val Ser Ser Gly Gly Gly Ser Gly Gly Gly Gly Ser
    130                 135                 140

Gly Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Ser Ala Ser Ser
                165                 170                 175

Ser Val Ser Tyr Met Asn Trp Tyr Gln Gln Thr Pro Gly Lys Ala Pro
            180                 185                 190

Lys Arg Trp Ile Tyr Asp Thr Ser Lys Leu Ala Ser Gly Val Pro Ser
        195                 200                 205

Arg Phe Ser Gly Ser Gly Ser Gly Thr Asp Tyr Thr Phe Thr Ile Ser
    210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Gln Gly Thr Lys Leu Gln Ile Thr Arg
                245                 250                 255

<210> SEQ ID NO 29
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Gly Gly Gly Ser Gly Gly Gly Ser Gly Gly Gly Gly Ser His
1               5                   10                  15

Val Lys Leu Gln Glu Ser Gly Pro Gly Leu Val Gln Pro Ser Gln Ser
            20                  25                  30

Leu Ser Leu Thr Cys Thr Val Ser Gly Phe Ser Leu Thr Asp Tyr Gly
        35                  40                  45

Val His Trp Val Arg Gln Ser Pro Gly Lys Gly Leu Glu Trp Leu Gly
    50                  55                  60

Val Ile Trp Ser Gly Gly Gly Thr Ala Tyr Asn Thr Ala Leu Ile Ser
65                  70                  75                  80

Arg Leu Asn Ile Tyr Arg Asp Asn Ser Lys Asn Gln Val Phe Leu Glu
                85                  90                  95

Met Asn Ser Leu Gln Ala Glu Asp Thr Ala Met Tyr Tyr Cys Ala Arg
            100                 105                 110

Arg Gly Ser Tyr Pro Tyr Asn Tyr Phe Asp Ala Trp Gly Cys Gly Thr
        115                 120                 125

Thr Val Thr Val Ser Ser Gly Gly Gly Ser Gly Gly Gly Gly Ser
    130                 135                 140

Gly Gly Gly Gly Ser Gln Ala Val Val Ile Gln Glu Ser Ala Leu Thr
145                 150                 155                 160

Thr Pro Pro Gly Glu Thr Val Thr Leu Thr Cys Gly Ser Ser Thr Gly
                165                 170                 175

Ala Val Thr Ala Ser Asn Tyr Ala Asn Trp Val Gln Glu Lys Pro Asp

```
                    180                 185                 190
His Cys Phe Thr Gly Leu Ile Gly Gly His Asn Asn Arg Pro Pro Gly
        195                 200                 205

Val Pro Ala Arg Phe Ser Gly Ser Leu Ile Gly Asp Lys Ala Ala Leu
    210                 215                 220

Thr Ile Ala Gly Thr Gln Thr Glu Asp Glu Ala Ile Tyr Phe Cys Ala
225                 230                 235                 240

Leu Trp Tyr Ser Asp His Trp Val Ile Gly Gly Thr Arg Leu Thr
                245                 250                 255

Val Leu Gly

<210> SEQ ID NO 30
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Gly Gly Gly Ser Gly Gly Gly Ser Gly Gly Gly Gly Ser Gln
1               5                   10                  15

Val Gln Leu Val Gln Ser Gly Gly Val Val Gln Pro Gly Arg Ser
            20                  25                  30

Leu Arg Leu Ser Cys Lys Ala Ser Gly Tyr Thr Phe Thr Arg Tyr Thr
            35                  40                  45

Met His Trp Val Arg Gln Ala Pro Gly Lys Gly Leu Glu Trp Ile Gly
50                  55                  60

Tyr Ile Asn Pro Ser Arg Gly Tyr Thr Asn Tyr Asn Gln Lys Phe Lys
65                  70                  75                  80

Asp Arg Phe Thr Ile Ser Arg Asp Asn Ser Lys Asn Thr Ala Phe Leu
                85                  90                  95

Gln Met Asp Ser Leu Arg Pro Glu Asp Thr Gly Val Tyr Phe Cys Ala
            100                 105                 110

Arg Tyr Tyr Asp Asp His Tyr Cys Leu Asp Tyr Trp Gly Gln Gly Thr
            115                 120                 125

Pro Val Thr Val Ser Ser Gly Gly Gly Ser Gly Gly Gly Gly Ser
    130                 135                 140

Gly Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Ser Ala Ser Ser
                165                 170                 175

Ser Val Ser Tyr Met Asn Trp Tyr Gln Gln Thr Pro Gly Lys Ala Pro
            180                 185                 190

Lys Arg Trp Ile Tyr Asp Thr Ser Lys Leu Ala Ser Gly Val Pro Ser
            195                 200                 205

Arg Phe Ser Gly Ser Gly Ser Gly Thr Asp Tyr Thr Phe Thr Ile Ser
    210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Gln Gly Thr Lys Leu Gln Ile Thr Arg
                245                 250                 255

<210> SEQ ID NO 31
<211> LENGTH: 259
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 31

Gly Gly Gly Gly Ser Gly Gly Gly Ser Gly Gly Gly Gly Ser His
1               5                   10                  15

Val Lys Leu Gln Glu Ser Gly Pro Gly Leu Val Gln Pro Ser Gln Ser
            20                  25                  30

Leu Ser Leu Thr Cys Thr Val Ser Gly Phe Ser Leu Thr Asp Tyr Gly
            35                  40                  45

Val His Trp Val Arg Gln Ser Pro Gly Lys Gly Leu Glu Trp Leu Gly
    50                  55                  60

Val Ile Trp Ser Gly Gly Gly Thr Ala Tyr Asn Thr Ala Leu Ile Ser
65                  70                  75                  80

Arg Leu Asn Ile Tyr Arg Asp Asn Ser Lys Asn Gln Val Phe Leu Glu
                85                  90                  95

Met Asn Ser Leu Gln Ala Glu Asp Thr Ala Met Tyr Tyr Cys Ala Arg
            100                 105                 110

Arg Gly Ser Tyr Pro Tyr Asn Tyr Phe Asp Ala Trp Gly Cys Gly Thr
            115                 120                 125

Thr Val Thr Val Ser Ser Gly Gly Gly Ser Gly Gly Gly Gly Ser
130                 135                 140

Gly Gly Gly Gly Ser Gln Ala Val Val Ile Gln Glu Ser Ala Leu Thr
145                 150                 155                 160

Thr Pro Pro Gly Glu Thr Val Thr Leu Thr Cys Gly Ser Ser Thr Gly
                165                 170                 175

Ala Val Thr Ala Ser Asn Tyr Ala Asn Trp Val Gln Glu Lys Pro Asp
            180                 185                 190

His Cys Phe Thr Gly Leu Ile Gly Gly His Asn Asn Arg Pro Pro Gly
        195                 200                 205

Val Pro Ala Arg Phe Ser Gly Ser Leu Ile Gly Asp Lys Ala Ala Leu
    210                 215                 220

Thr Ile Ala Gly Thr Gln Thr Glu Asp Glu Ala Ile Tyr Phe Cys Ala
225                 230                 235                 240

Leu Trp Tyr Ser Asp His Trp Val Ile Gly Gly Gly Thr Arg Leu Thr
                245                 250                 255

Val Leu Gly

<210> SEQ ID NO 32
<211> LENGTH: 4
<212> TYPE: PRT
<213> ORGANISM: Unknown
<220> FEATURE:
<223> OTHER INFORMATION: Description of Unknown: Conserved mammalian
      peptide

<400> SEQUENCE: 32

Ile Arg Asp Phe
1

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 33

Arg Ala Ser Gln Ser Ile Ser Asp Tyr Leu His
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Ala Ser Gln Ser Ile Ser Asp Tyr Leu Tyr
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Ala Ser Gln Ser Ile Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Ala Ser Gln Ser Ile Ser
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Asn Gly His Ser Phe Pro Leu Thr
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Asn Gly His Ser Phe Pro Leu Thr
1               5

<210> SEQ ID NO 39
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ser Gln Ser Ile Ser Asp Tyr
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Gln Ser Ile Ser Asp Tyr
1               5

<210> SEQ ID NO 41
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Tyr Ala Ser
1

<210> SEQ ID NO 42
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Ala Ser
1

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly His Ser Phe Pro Leu
1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly His Ser Phe Pro Leu
```

```
<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Ser Gln Ser Ile Ser Asp Tyr
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Ser Gln Ser Ile Ser Asp Tyr
1               5

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Tyr Ala Ser Gln Ser Ile Ser Gly Ile Pro Ser Arg
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Tyr Ala Ser Gln Ser Ile Ser Gly Ile Pro Ala Arg
1               5                   10

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly His Ser Phe Pro Leu
1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 50

Gly His Ser Phe Pro Leu
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Ser Ile Ser Asp Tyr
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Ser Ile Ser Asp Tyr
1               5

<210> SEQ ID NO 53
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Tyr Ala Ser
1

<210> SEQ ID NO 54
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Tyr Ala Ser
1

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Asn Gly His Ser Phe Pro Leu Thr
1               5

<210> SEQ ID NO 56

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Asn Gly His Ser Phe Pro Leu Thr
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asn Tyr Asp Ile Asn
1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asn Tyr Asp Ile Asn
1               5

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Trp Ile Phe Pro Gly Asp Gly Ser Thr Gln Tyr Asn Glu Lys Phe Lys
1               5                   10                  15

Gly

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Trp Ile Phe Pro Gly Asp Asp Ser Thr Gln Tyr Asn Glu Lys Phe Lys
1               5                   10                  15

Gly

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 61

Gln Thr Thr Ala Thr Trp Phe Ala Tyr
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Thr Thr Gly Thr Trp Phe Ala Tyr
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Tyr Thr Phe Thr Asn Tyr
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Tyr Thr Phe Thr Asn Tyr
1               5

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Pro Gly Asp Gly
1

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Pro Gly Asp Asp
1

<210> SEQ ID NO 67

```
<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Thr Thr Ala Thr Trp Phe Ala
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Thr Thr Gly Thr Trp Phe Ala
1               5

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Ser Gly Tyr Thr Phe Thr Asn Tyr Asp
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Ser Gly Tyr Thr Phe Thr Asn Tyr Asp
1               5                   10

<210> SEQ ID NO 71
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ile Phe Pro Gly Asp Gly Ser Thr Gln Tyr Asn Glu Lys Phe Lys Gly
1               5                   10                  15

Lys Ala

<210> SEQ ID NO 72
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 72

Ile Phe Pro Gly Asp Asp Ser Thr Gln Tyr Asn Glu Lys Phe Lys Gly
1               5                   10                  15

Arg Val

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Thr Thr Ala Thr Trp Phe Ala
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Thr Thr Gly Thr Trp Phe Ala
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Tyr Thr Phe Thr Asn Tyr Asp
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Tyr Thr Phe Thr Asn Tyr Asp
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ile Phe Pro Gly Asp Gly Ser Thr
1               5

<210> SEQ ID NO 78
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ile Phe Pro Gly Asp Asp Ser Thr
1               5

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Arg Gln Thr Thr Ala Thr Trp Phe Ala Tyr
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Arg Gln Thr Thr Gly Thr Trp Phe Ala Tyr
1               5                   10

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tcagttttgg cccaggcggc c                                              21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
accactagtt gggccggcct g                                              21

<210> SEQ ID NO 83
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cttcgctgtt tttcaatatt ttctgttatt gcttcagttt tggcccaggc ggcc          54
```

```
<210> SEQ ID NO 84
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gagccgccac cctcagaacc gccaccctca gagccaccac tagttgggcc ggcctg          56

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Phe Val Ser Ile Arg Asp Phe Gly
1               5

<210> SEQ ID NO 86
<211> LENGTH: 4
<212> TYPE: PRT
<213> ORGANISM: Unknown
<220> FEATURE:
<223> OTHER INFORMATION: Description of Unknown: Conserved mammalian
      peptide

<400> SEQUENCE: 86

Ile Gln Asp Phe
1

<210> SEQ ID NO 87
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Asn Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gln Thr Thr Ala Thr Trp Phe Ala Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Met Thr Gln Ser Pro Ala Thr Leu
    130                 135                 140
```

```
Ser Val Ser Pro Gly Glu Arg Val Ser Leu Ser Cys Arg Ala Ser Gln
145                 150                 155                 160

Ser Ile Ser Asp Tyr Leu His Trp Tyr Gln Gln Lys Ser His Glu Ser
            165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser
            195                 200

<210> SEQ ID NO 88
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Val Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gln Thr Thr Ala Thr Trp Phe Ala Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Glu Ile Val Met Thr Gln Ser Pro Ala Thr Leu
    130                 135                 140

Ser Val Ser Pro Gly Glu Arg Val Thr Leu Ser Cys Arg Ala Ser Gln
145                 150                 155                 160

Ser Ile Ser Asp Tyr Leu Tyr Trp Tyr Gln Gln Lys Ser His Glu Ser
            165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser
            195                 200

<210> SEQ ID NO 89
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (18)..(18)
<223> OTHER INFORMATION: Any amino acid
```

<400> SEQUENCE: 89

```
Gln Val Xaa Xaa Val Gln Ser Gly Ala Glu Val Val Lys Pro Gly Ala
1               5                   10                  15

Ser Xaa Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gln Thr Thr Ala Thr Trp Phe Ala Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Val Gly Ser Glu Ile Val Met Thr Gln Ser Pro Ala Thr Leu
    130                 135                 140

Ser Val Ser Pro Gly Glu Arg Val Thr Leu Ser Cys Arg Ala Ser Gln
145                 150                 155                 160

Ser Ile Gly Asp Tyr Leu Tyr Trp Tyr Gln Gln Lys Ser His Glu Ser
                165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser
        195                 200
```

<210> SEQ ID NO 90
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid

<400> SEQUENCE: 90

```
Gln Val Xaa Leu Val Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Thr Ser Thr Ala Tyr
65                  70                  75                  80

Leu Glu Leu Ser Ser Leu Gly Ser Glu Asp Thr Ala Val Tyr Phe Cys
                85                  90                  95

Ala Arg Gln Thr Thr Gly Thr Trp Phe Ala Tyr Trp Gly Gln Gly Thr
            100                 105                 110

Leu Val Thr Val Ser Ser Gly Gly Gly Gly Ser Gly Gly Gly Gly Ser
        115                 120                 125
```

Gly Gly Gly Gly Ser Glu Ile Val Met Thr Gln Ser Pro Ala Thr Leu
            130                 135                 140

Ser Val Ser Pro Gly Glu Arg Val Thr Leu Ser Cys Arg Ala Ser Gln
145                 150                 155                 160

Ser Ile Ser Asp Tyr Leu Tyr Trp Tyr Gln Gln Lys Ser His Glu Ser
            165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser
            195                 200

<210> SEQ ID NO 91
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid

<400> SEQUENCE: 91

Gln Val Xaa Leu Val Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gln Thr Thr Ala Thr Trp Phe Ala Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Val Gly Ser Glu Ile Val Met Thr Gln Ser Pro Ala Thr Leu
            130                 135                 140

Ser Val Ser Pro Gly Glu Arg Val Thr Leu Ser Cys Arg Ala Ser Gln
145                 150                 155                 160

Ser Ile Gly Asp Tyr Leu Tyr Trp Tyr Gln Gln Lys Ser His Glu Ser
            165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser
            195                 200

<210> SEQ ID NO 92
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 92

Gln Val Gln Leu Val Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Thr Ser Thr Ala Tyr
65                  70                  75                  80

Met Glu Leu Ser Ser Leu Gly Ser Glu Asp Thr Ala Val Tyr Phe Cys
                85                  90                  95

Ala Arg Gln Thr Thr Ala Thr Trp Phe Ala Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Met Thr Gln Ser Pro Ala Thr Leu
    130                 135                 140

Ser Val Ser Pro Gly Glu Arg Val Thr Leu Ser Cys Arg Ala Ser Gln
145                 150                 155                 160

Ser Ile Ser Asp Tyr Leu Tyr Trp Tyr Gln Gln Lys Ser His Glu Ser
                165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser
        195                 200

<210> SEQ ID NO 93
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Val Gln Leu Val Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Thr Ser Thr Ala Tyr
65                  70                  75                  80

Leu Glu Leu Ser Ser Leu Gly Ser Glu Asp Thr Ala Val Tyr Phe Cys
                85                  90                  95

Ala Arg Gln Thr Thr Gly Thr Trp Phe Ala Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Met Thr Gln Ser Pro Ala Thr Leu
    130                 135                 140
```

```
Ser Val Ser Pro Gly Glu Arg Val Thr Leu Ser Cys Arg Ala Ser Gln
145                 150                 155                 160

Ser Ile Ser Asp Tyr Leu Tyr Trp Tyr Gln Gln Lys Ser His Glu Ser
                165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser
        195                 200
```

<210> SEQ ID NO 94
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid

<400> SEQUENCE: 94

```
Gln Val Xaa Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Asn Tyr
            20                  25                  30

Asp Ile Asn Trp Ala Arg Gln Arg Pro Gly Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Thr Gly Thr Ala Tyr
65                  70                  75                  80

Met Glu Leu Ser Ser Leu Arg Ser Glu Asp Thr Ala Val Tyr Phe Cys
                85                  90                  95

Ala Arg Gln Thr Thr Ala Thr Trp Phe Ala Tyr Trp Gly Gln Gly Thr
            100                 105                 110

Val Val Thr Val Ser Ser Gly Gly Gly Gly Ser Gly Gly Gly Gly Ser
        115                 120                 125

Gly Gly Gly Gly Asn Glu Ile Val Met Thr Gln Ser Pro Ala Thr Leu
    130                 135                 140

Ser Val Ser Pro Gly Glu Arg Val Thr Leu Ser Cys Arg Ala Ser Gln
145                 150                 155                 160

Ser Ile Ser Asp Tyr Val Tyr Trp Tyr Gln Gln Lys Pro His Glu Ser
                165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser
        195                 200
```

<210> SEQ ID NO 95
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid
<220> FEATURE:

```
<221> NAME/KEY: MOD_RES
<222> LOCATION: (5)..(5)
<223> OTHER INFORMATION: Any amino acid

<400> SEQUENCE: 95

Gln Val Xaa Leu Xaa Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
        35                  40                  45

Gly Trp Ile Phe Pro Gly Asp Gly Ser Thr Gln Tyr Asn Glu Lys Phe
50                  55                  60

Lys Gly Lys Ala Thr Leu Thr Thr Asp Thr Ser Thr Ser Thr Ala Tyr
65                  70                  75                  80

Leu Glu Leu Ser Ser Leu Gly Ser Glu Asp Thr Ala Val Tyr Phe Cys
                85                  90                  95

Ala Arg Gln Thr Thr Gly Thr Trp Phe Ala Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Met Thr Gln Ser Pro Ala Thr Leu
130                 135                 140

Ser Val Ser Pro Gly Glu Arg Val Thr Leu Ser Cys Arg Ala Ser Gln
145                 150                 155                 160

Ser Ile Ser Asp Tyr Leu Tyr Trp Tyr Gln Gln Lys Ser His Glu Ser
                165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser
            195                 200

<210> SEQ ID NO 96
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Val Gln Leu Val Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
        35                  40                  45

Gly Trp Ile Phe Pro Gly Asp Gly Ser Thr Gln Tyr Asn Glu Lys Phe
50                  55                  60

Lys Gly Lys Ala Thr Leu Thr Thr Asp Thr Ser Thr Ser Thr Ala Tyr
65                  70                  75                  80

Met Glu Leu Ser Ser Leu Ser Ser Glu Asp Thr Ala Val Tyr Phe Cys
                85                  90                  95

Ala Arg Gln Thr Thr Ala Thr Trp Phe Ala Tyr Trp Gly Gln Gly Thr
            100                 105                 110

Leu Val Thr Val Ser Ser Gly Gly Gly Gly Ser Gly Gly Gly Gly Ser
        115                 120                 125
```

Gly Gly Gly Gly Ser Glu Ile Val Met Thr Gln Ser Pro Ala Thr Leu
            130                 135                 140

Ser Val Ser Pro Gly Glu Arg Val Thr Leu Ser Cys Arg Ala Ser Gln
145                 150                 155                 160

Glu Ile Ser Asp Tyr Leu Tyr Trp Tyr Gln Gln Lys Ser His Glu Ser
                165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser
        195                 200

<210> SEQ ID NO 97
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Val Gln Leu Val Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Val
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gln Thr Thr Ser Thr Trp Phe Ala Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Glu Ile Val Met Thr Gln Ser Pro Ala Thr Leu
    130                 135                 140

Ser Val Ser Pro Gly Glu Arg Val Thr Leu Ser Cys Arg Ala Ser Gln
145                 150                 155                 160

Glu Ile Ser Asp Tyr Leu Tyr Trp Tyr Gln Gln Lys Ser His Glu Ser
                165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser
        195                 200

<210> SEQ ID NO 98
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gln Val Gln Leu Val Gln Ser Gly Ala Glu Val Val Lys Pro Gly Ala
1               5                   10                  15

```
Ser Val Lys Leu Ser Cys Lys Thr Ser Gly Tyr Thr Phe Thr Asn Tyr
         20                  25                  30

Asp Ile Asn Trp Val Arg Gln Arg Pro Gly Gln Gly Leu Glu Trp Ile
         35                  40                  45

Gly Trp Ile Phe Pro Gly Asp Gly Ser Thr Gln Tyr Asn Glu Lys Phe
 50                      55                  60

Lys Gly Lys Ala Thr Leu Thr Thr Asp Thr Ser Thr Ser Thr Ala Tyr
 65                  70                  75                  80

Leu Glu Leu Ser Ser Leu Gly Ser Glu Asp Thr Ala Val Tyr Phe Cys
                 85                  90                  95

Ala Arg Gln Thr Thr Gly Thr Trp Phe Ala Tyr Trp Gly Gln Gly Thr
                100                 105                 110

Leu Val Thr Val Ser Ser Gly Gly Gly Ser Gly Gly Gly Gly Ser
                115                 120                 125

Gly Gly Gly Gly Ser Glu Ile Val Met Thr Gln Ser Pro Ala Thr Leu
130                 135                 140

Ser Val Ser Pro Gly Glu Arg Val Thr Leu Ser Cys Arg Ala Ser Gln
145                 150                 155                 160

Ser Ile Ser Asp Tyr Leu Tyr Trp Tyr Gln Gln Lys Ser His Glu Ser
                165                 170                 175

Pro Arg Leu Leu Ile Lys Tyr Ala Ser Gln Ser Ile Ser Gly Ile Pro
                180                 185                 190

Ala Arg Phe Ser Gly Ser Gly Ser
                195                 200

<210> SEQ ID NO 99
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(6)
<223> OTHER INFORMATION: Any amino acid
<220> FEATURE:
<221> NAME/KEY: MOD_RES
<222> LOCATION: (17)..(19)
<223> OTHER INFORMATION: Any amino acid

<400> SEQUENCE: 99

Gln Xaa Xaa Xaa Xaa Ser Gly Ala Glu Val Val Lys Pro Gly Ala
 1               5                  10                  15

Xaa Xaa Xaa Leu Ser Cys Lys Thr Ser Gly Tyr Thr Phe Thr Asn Tyr
         20                  25                  30

Asp Ile Asn Trp Val Arg Gln Arg Pro Gly Gln Gly Leu Glu Trp Ile
         35                  40                  45

Gly Trp Ile Phe Pro Gly Asp Gly Ser Thr Gln Tyr Asn Glu Lys Phe
 50                      55                  60

Lys Gly Lys Ala Thr Leu Thr Thr Asp Thr Ser Thr Ser Thr Ala Tyr
 65                  70                  75                  80

Leu Glu Leu Ser Ser Leu Gly Ser Glu Asp Thr Ala Val Tyr Phe Cys
                 85                  90                  95

Ala Arg Gln Thr Thr Gly Thr Trp Phe Ala Tyr Trp Gly Gln Gly Thr
                100                 105                 110

Leu Val Thr Val Ser Ser Gly Gly Gly Ser Gly Gly Gly Gly Ser
                115                 120                 125
```

```
Gly Gly Gly Gly Ser Glu Ile Val Met Thr Gln Ser Pro Ala Thr Leu
        130                 135                 140

Ser Val Ser Pro Gly Glu Arg Val Thr Leu Ser Cys Arg Ala Ser Gln
145                 150                 155                 160

Ser Ile Ser Asp Tyr Leu Tyr Trp Tyr Gln Gln Lys Ser His Glu Ser
                165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser
        195                 200

<210> SEQ ID NO 100
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (170)..(171)
<223> OTHER INFORMATION: Any amino acid

<400> SEQUENCE: 100

Gln Val Xaa Xaa Xaa Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Thr Ser Thr Ala Tyr
65                  70                  75                  80

Leu Glu Leu Ser Ser Leu Gly Ser Glu Asp Thr Ala Val Tyr Phe Cys
                85                  90                  95

Ala Arg Gln Thr Thr Gly Thr Trp Phe Ala Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Glu Ile Val Met Thr Gln Ser Pro Ala Thr Leu
        130                 135                 140

Ser Val Ser Pro Gly Glu Arg Val Thr Leu Ser Cys Arg Ala Ser Gln
145                 150                 155                 160

Ser Ile Ser Asp Tyr Leu Tyr Trp Tyr Xaa Xaa Lys Ser His Glu Ser
                165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser
        195                 200

<210> SEQ ID NO 101
<211> LENGTH: 200
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(5)
<223> OTHER INFORMATION: Any amino acid

<400> SEQUENCE: 101

Gln Xaa Xaa Xaa Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
        35                  40                  45

Gly Trp Ile Phe Pro Gly Asp Gly Ser Thr Gln Tyr Asn Glu Lys Phe
50                  55                  60

Lys Gly Lys Ala Thr Leu Thr Thr Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gln Thr Thr Ala Thr Trp Phe Ala Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Val Gly Ser Glu Ile Val Met Thr Gln Ser Pro Ala Thr Leu
130                 135                 140

Ser Val Ser Pro Gly Glu Arg Val Thr Leu Ser Cys Arg Ala Ser Gln
145                 150                 155                 160

Ser Ile Gly Asp Tyr Leu Tyr Trp Tyr Gln Gln Lys Ser His Glu Ser
            165                 170                 175

Pro Arg Leu Leu Ile Lys Tyr Ala Ser Gln Ser Ile Ser Gly Ile Pro
        180                 185                 190

Ala Arg Phe Ser Gly Ser Gly Ser
            195                 200

<210> SEQ ID NO 102
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(5)
<223> OTHER INFORMATION: Any amino acid

<400> SEQUENCE: 102

Gln Val Xaa Xaa Xaa Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
        35                  40                  45

Gly Trp Ile Phe Pro Gly Asp Asp Ser Thr Gln Tyr Asn Glu Lys Phe
50                  55                  60

Lys Gly Lys Ala Thr Leu Thr Thr Asp Thr Ser Thr Ser Thr Ala Tyr
65                  70                  75                  80
```

```
Met Glu Leu Ser Ser Leu Arg Ser Glu Asp Thr Ala Val Tyr Phe Cys
                85                  90                  95

Ala Arg Gln Thr Thr Gly Thr Trp Phe Ala Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Glu Ile Val Met Thr Gln Ser Pro Ala Thr Leu
            130                 135                 140

Ser Val Ser Pro Gly Glu Arg Val Thr Leu Ser Cys Arg Ala Ser Gln
145                 150                 155                 160

Ser Ile Ser Asp Tyr Leu Tyr Trp Tyr Gln Gln Lys Ser His Glu Ser
                165                 170                 175

Pro Arg Leu Leu Ile Lys Tyr Ala Ser Gln Ser Ile Pro Gly Ile Pro
            180                 185                 190

Ala Arg Phe Ser Gly Ser Gly Ser
            195                 200

<210> SEQ ID NO 103
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 103

Gln Val Xaa Leu Xaa Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gln Thr Thr Ala Thr Trp Phe Ala Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Glu Ile Val Met Thr Gln Ser Pro Ala Thr Leu
            130                 135                 140

Ser Val Ser Pro Gly Glu Arg Val Thr Leu Ser Cys Arg Ala Ser Gln
145                 150                 155                 160

Ser Ile Ser Asp Tyr Leu Tyr Trp Tyr Gln Gln Lys Ser His Glu Ser
                165                 170                 175

Pro Arg Leu Leu Ile Lys Tyr Ala Ser Gln Ser Ile Ser Gly Ile Pro
            180                 185                 190
```

```
Ala Arg Phe Ser Gly Ser Gly Ser
        195                 200

<210> SEQ ID NO 104
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid

<400> SEQUENCE: 104

Gln Val Xaa Leu Val Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
            20                  25                  30

Asp Ile Asn Trp Val Arg Gln Arg Pro Gly Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Thr Ser Thr Ala Tyr
65                  70                  75                  80

Met Glu Leu Ser Ser Leu Gly Ser Glu Asp Thr Ala Val Tyr Phe Cys
                85                  90                  95

Thr Arg Gln Thr Thr Ala Thr Trp Phe Ala Tyr Trp Gly Gln Gly Thr
            100                 105                 110

Leu Val Thr Val Ser Ser Gly Gly Gly Gly Ser Gly Gly Gly Gly Ser
        115                 120                 125

Ser Gly Gly Gly Ser Glu Ile Val Met Thr Gln Ser Pro Ala Thr Leu
    130                 135                 140

Ser Val Ser Pro Gly Glu Arg Val Thr Leu Ser Cys Arg Ala Ser Gln
145                 150                 155                 160

Ser Ile Gly Asp Tyr Leu Tyr Trp Tyr Gln Gln Lys Ser His Glu Ser
                165                 170                 175

Pro Arg Leu Leu Ile Lys Tyr Ala Ser Gln Ser Ile Ser Gly Ile Pro
            180                 185                 190

Ala Arg Phe Ser Gly Ser Gly Ser
        195                 200

<210> SEQ ID NO 105
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 105

Gln Val Xaa Leu Xaa Gln Ser Gly Ala Glu Val Val Lys Pro Gly Ala
1               5                   10                  15
```

-continued

```
Ser Val Lys Leu Ser Cys Lys Thr Ser Gly Tyr Thr Phe Thr Asn Tyr
             20                  25                  30

Asp Ile Asn Trp Val Arg Gln Arg Pro Gly Gln Gly Leu Glu Trp Ile
         35                  40                  45

Gly Trp Ile Phe Pro Gly Asp Gly Ser Thr Gln Tyr Asn Glu Lys Phe
     50                  55                  60

Lys Gly Lys Ala Thr Leu Thr Thr Asp Thr Ser Thr Ser Thr Ala Tyr
 65                  70                  75                  80

Leu Glu Leu Ser Ser Leu Gly Ser Glu Asp Thr Ala Val Tyr Phe Cys
                 85                  90                  95

Ala Arg Gln Thr Thr Gly Thr Trp Phe Ala Tyr Trp Gly Gln Gly Thr
             100                 105                 110

Leu Val Thr Val Ser Ser Gly Gly Gly Gly Ser Gly Gly Gly Gly Ser
             115                 120                 125

Gly Gly Gly Gly Ser Glu Ile Val Met Thr Gln Ser Pro Ala Thr Leu
         130                 135                 140

Ser Val Ser Pro Gly Glu Arg Val Thr Leu Ser Cys Arg Ala Ser Gln
145                 150                 155                 160

Ser Ile Ser Asp Tyr Leu Tyr Trp Tyr Gln Gln Lys Ser His Glu Ser
             165                 170                 175

Pro Arg Leu Leu Ile Lys Tyr Ala Ser Gln Ser Ile Ser Gly Ile Pro
             180                 185                 190

Ala Arg Phe Ser Gly Ser Gly Ser
             195                 200
```

ANTIBODIES, COMPOSITIONS, AND USES

The present specification makes reference to a Sequence Listing (submitted electronically as a .txt file named "2003080-0937_SL.txt" on Aug. 26, 2015). The .txt file was generated on Jul. 31, 2015 and is 129,896 bytes in size. The entire contents of the Sequence Listing are herein incorporated by reference. The below Description of the Sequences lists the identity of the sequences in the Sequence Listing.

BACKGROUND

Tumors often create a micro-environment that suppresses the immune system. Removing this immunologic block has been a focus of many efforts to develop effective therapies.

SUMMARY

The present invention provides novel antibodies that bind to B7H3. In some embodiments, such antibodies share significant sequence identity with 8H9. In some embodiments, provided antibodies represent affinity matured humanized variants of 8H9.

In some embodiments, provided antibodies bind an epitope in B7H3 that is recognized by 8H9. Among other things, the present invention provides the surprising insight that m8H9, and humanized variants thereof, bind to a distinct epitope on B7H3 that is not recognized by certain other antibodies to B7H3. The present invention therefore defines a useful set of new antibodies—those that are not m8H9 but bind to the same epitope.

The present invention provides an antibody agent that binds specifically to protein 2Ig-B7H3 or 4Ig-B7H3 and includes an immunoglobulin light chain as set forth in a SEQ ID NO. selected from the group consisting of SEQ ID NO.: 1, 2, 3, 4, 5, 6, 7 and 8, and includes an immunoglobulin heavy chain as set forth in a SEQ ID NO. selected from the group consisting of SEQ ID NO.: 9, 10, 11, 12, 13, 14, 15 and 16.

In some embodiments, the immunoglobulin light chain is set forth in SEQ ID NO.: 1 and the immunoglobulin heavy chain is set forth in SEQ ID NO.: 9. In some embodiments, the antibody agent is an antibody having immunoglobulin light chains set forth in SEQ ID NO.: 1 and immunoglobulin heavy chains set forth in SEQ ID NO.: 9. In some embodiments, the immunoglobulin light chain is set forth in SEQ ID NO.: 2 and the immunoglobulin heavy chain is set forth in SEQ ID NO.: 10. In some embodiments, the antibody agent is an antibody having immunoglobulin light chains set forth in SEQ ID NO.: 2 and immunoglobulin heavy chains set forth in SEQ ID NO.: 10. In some embodiments, the immunoglobulin light chain is set forth in SEQ ID NO.: 3 and the immunoglobulin heavy chain is set forth in SEQ ID NO.: 11. In some embodiments, the antibody agent is an antibody having immunoglobulin light chains set forth in SEQ ID NO.: 3 and immunoglobulin heavy chains set forth in SEQ ID NO.: 11. In some embodiments, the immunoglobulin light chain is set forth in SEQ ID NO.: 4 and the immunoglobulin heavy chain is set forth in SEQ ID NO.: 12. In some embodiments, the antibody agent is an antibody having immunoglobulin light chains set forth in SEQ ID NO.: 4 and immunoglobulin heavy chains set forth in SEQ ID NO.: 12. In some embodiments, the immunoglobulin light chain is set forth in SEQ ID NO.: 2 and the immunoglobulin heavy chain is set forth in SEQ ID NO.: 11. In some embodiments, the antibody agent is an antibody having immunoglobulin light chains set forth in SEQ ID NO.: 2 and immunoglobulin heavy chains set forth in SEQ ID NO.: 11. In some embodiments, the immunoglobulin light chain is set forth in SEQ ID NO.: 3 and the immunoglobulin heavy chain is set forth in SEQ ID NO.: 10. In some embodiments, the antibody agent is an antibody having immunoglobulin light chains set forth in SEQ ID NO.: 3 and immunoglobulin heavy chains set forth in SEQ ID NO.: 10. In some embodiments, the immunoglobulin light chain is set forth in SEQ ID NO.: 5 and the immunoglobulin heavy chain is set forth in SEQ ID NO.: 13. In some embodiments, the antibody agent is an antibody having immunoglobulin light chains set forth in SEQ ID NO.: 5 and immunoglobulin heavy chains set forth in SEQ ID NO.: 13. In some embodiments, the immunoglobulin light chain is set forth in SEQ ID NO.: 6 and the immunoglobulin heavy chain is set forth in SEQ ID NO.: 14. In some embodiments, the antibody agent is an antibody having immunoglobulin light chains set forth in SEQ ID NO.: 6 and immunoglobulin heavy chains set forth in SEQ ID NO.: 14. In some embodiments, the immunoglobulin light chain is set forth in SEQ ID NO.: 7 and the immunoglobulin heavy chain is set forth in SEQ ID NO.: 15. In some embodiments, the antibody agent is an antibody having immunoglobulin light chains set forth in SEQ ID NO.: 7 and immunoglobulin heavy chains set forth in SEQ ID NO.: 15. In some embodiments, the immunoglobulin light chain is set forth in SEQ ID NO.: 8 and the immunoglobulin heavy chain is set forth in SEQ ID NO.: 16. In some embodiments, the antibody agent is an antibody having immunoglobulin light chains set forth in SEQ ID NO.: 8 and immunoglobulin heavy chains set forth in SEQ ID NO.: 16. In some embodiments, the immunoglobulin light chain comprises a threonine residue at position 20 and a tyrosine residue at position 34, and wherein the immunoglobulin heavy chain comprises a threonine residue at position 24, a glycine residue at position 42, an aspartic acid residue at position 56, and a glycine residue at position 102.

The present invention provides murine 8H9 antibody, wherein the immunoglobulin light chains includes a threonine residue at position 20 and a tyrosine residue at position 34, and wherein the immunoglobulin heavy chains includes a threonine residue at position 24, a glycine residue at position 42, an aspartic acid residue at position 56, and a glycine residue at position 102.

In some embodiments, any of the antibodies disclosed herein includes one or more of a threonine residue at position 20 and a tyrosine residue at position 34 of the immunoglobulin light chain, and a threonine residue at position 24, a glycine residue at position 42, an aspartic acid residue at position 56, and a glycine residue at position 102 of the immunoglobulin heavy chain, or includes a homologous amino acid substitution thereof at any of these positions.

In some embodiments, an immunoglobulin light chain is fused to a polypeptide set forth in SEQ ID NO.: 30 or SEQ ID NO.: 31.

In some embodiments, any of the antibody agents disclosed herein is conjugated to a therapeutic agent or detection agent.

In some embodiments, any of the antibody agents disclosed herein, including antibodies, is conjugated to a radioisotope, a drug conjugate, a nanoparticle, an immune-toxins, or any other payload.

In some embodiments, any of the antibody agents disclosed herein, including antibodies, is conjugated to a diagnostic or imaging agent, or both.

In some embodiments, an antibody agent is a bispecific antibody.

In some embodiments, an antibody agent has a first and a second specificity, and the first specificity binds to protein 2Ig-B7H3 or 4Ig-B7H3, and the second specificity binds to CD3 on T cells or DOTA.

The present invention provides an scFv that binds specifically to protein 2Ig-B7H3 or 4Ig-B7H3 and includes the polypeptide set forth in a SEQ ID NO. selected from the group consisting of SEQ ID NO.: 17, 18, 19, 20, 21, 22, 23, 24, 25, 26 and 27.

In some embodiments, a polypeptide of an scFv includes a threonine at position 24, a glycine at position 42, an aspartic acid residue at position 56, a glycine residue at position 102, a threonine residue at position 153 and a tyrosine residue at position 167.

In some embodiments, a scFv includes one or more of a threonine at position 24, a glycine at position 42, a aspartic acid residue at position 56, a glycine residue at position 102, a threonine residue at position 153 and a tyrosine residue at position 167, or includes a homologous amino acid substitution thereof at any of these positions.

In some embodiments, a polypeptide of an scFv is fused to a second polypeptide set forth in SEQ ID NO.: 28 or SEQ ID NO.: 29.

In some embodiments, the scFv is conjugated to a therapeutic agent or detection agent.

In some embodiments, any of the scFvs disclosed herein is part of a chimeric antigen receptor.

The present invention provides an antibody agent that binds specifically to the epitope set forth in SEQ ID NO.: 32 located in the FG loop in the V-domain of protein 2Ig-B7H3 and in the V1 and V2 domains of protein 4Ig-B7H3, which antibody agent is not m8H9.

The present invention provides an antibody agent that binds specifically to the FG loop in the V-domain of protein 2Ig-B7H3 and in the V1 and V2 domains of protein 4Ig-B7H3 with a $K_D$ of less than 2 nM, which antibody agent is not m8H9.

In some embodiments, any of the antibody agents disclosed herein suppresses an inhibitory effect of B7H3 on T cell proliferation and function.

In some embodiments, any of the antibody agents disclosed herein suppresses an inhibitory effect of B7H3 on NK cell activity and function.

The present invention provides a pharmaceutical composition including any of the antibody agents, scFvs, or humanized antibodies or antigen-binding fragments thereof disclosed herein, and a pharmaceutically acceptable carrier.

The present invention provides a method of treating cancer, including administering to a patient in need thereof a therapeutically effective amount of any one or more of the antibody agents, scFvs, humanized antibodies or antigen-binding fragments thereof disclosed herein.

The present invention provides a method of modulating the immune system, including administering to a patient in need thereof a therapeutically effective amount of any one or more of the antibody agents, scFvs, humanized antibodies or antigen-binding fragments thereof disclosed herein.

The present invention provides a method of treating cancer, the method including steps of administering to a subject a composition including an anti-B7H3 antibody agent that binds to B7H3's FG-loop.

In some embodiments, the cancer is or includes a neuroblastoma. In some embodiments, the cancer is or includes a cervical cancer. In some embodiments, the cancer includes B7H3-positive tumor cells.

The present invention provides a method of enhancing T-cell mediated cytotoxicity in a subject, the method including steps of administering to a subject a composition including an anti-B7H3 antibody agent that binds to B7H3's FG-loop.

In some embodiments, the antibody agent is or includes an 8H9 antibody agent.

In some embodiments, the 8H9 antibody agent includes a polypeptide that includes a light chain CDR1 sequence selected from the group consisting of SEQ ID NO.: 33, 34, 39, 40, 45, 46, 51 and 52.

In some embodiments, the 8H9 antibody agent includes a polypeptide that includes a light chain CDR2 sequence selected from the group consisting of SEQ ID NO.: 35, 36, 41, 42, 47, 48, 53 and 54.

In some embodiments, the 8H9 antibody agent includes a polypeptide that includes a light chain CDR3 sequence selected from the group consisting of SEQ ID NO.: 37, 38, 43, 44, 49, 50, 55 and 56.

In some embodiments, the 8H9 antibody agent includes a polypeptide that includes a heavy chain CDR1 sequence selected from the group consisting of SEQ ID NO.: 57, 58, 63, 64, 69, 70, 75 and 76.

In some embodiments, the 8H9 antibody agent includes a polypeptide that includes a heavy chain CDR2 sequence selected from the group consisting of SEQ ID NO.: 59, 60, 65, 66, 71, 72, 77 and 78.

In some embodiments, the 8H9 antibody agent includes a polypeptide that includes a heavy chain CDR3 sequence selected from the group consisting of SEQ ID NO.: 61, 62, 67, 68, 73, 74, 79 and 80.

In some embodiments, the 8H9 antibody agent includes a polypeptide that includes a light chain CDR1 sequence selected from the group consisting of SEQ ID NO.: 33, 34, 39, 40, 45, 46, 51 and 52; a light chain CDR2 sequence selected from the group consisting of SEQ ID NO.: 35, 36, 41, 42, 47, 48, 53 and 54; and a light chain CDR3 sequence selected from the group consisting of SEQ ID NO.: 37, 38, 43, 44, 49, 50, 55 and 56.

In some embodiments, the 8H9 antibody agent includes a polypeptide that includes a heavy chain CDR1 sequence selected from the group consisting of SEQ ID NO.: 57, 58, 63, 64, 69, 70, 75 and 76; a heavy chain CDR2 sequence selected from the group consisting of SEQ ID NO.: 59, 60, 65, 66, 71, 72, 77 and 78; and a heavy chain CDR3 sequence selected from the group consisting of SEQ ID NO.: 61, 62, 67, 68, 73, 74, 79 and 80.

In some embodiments, the 8H9 antibody agent includes a polypeptide that includes a light chain CDR1 sequence selected from the group consisting of SEQ ID NO.: 33, 34, 39, 40, 45, 46, 51 and 52; a light chain CDR2 sequence selected from the group consisting of SEQ ID NO.: 35, 36, 41, 42, 47, 48, 53 and 54; and a light chain CDR3 sequence selected from the group consisting of SEQ ID NO.: 37, 38, 43, 44, 49, 50, 55 and 56; and a heavy chain CDR1 sequence selected from the group consisting of SEQ ID NO.: 57, 58, 63, 64, 69, 70, 75 and 76; a heavy chain CDR2 sequence selected from the group consisting of SEQ ID NO.: 59, 60, 65, 66, 71, 72, 77 and 78; and a heavy chain CDR3 sequence selected from the group consisting of SEQ ID NO.: 61, 62, 67, 68, 73, 74, 79 and 80.

In some embodiments, any of the antibody agents disclosed herein includes or consists of an 8H9 antibody or antigen-binding fragment thereof.

In some embodiments, the 8H9 antibody is or comprises m8H9, h8H9, or ham8H9.

In some embodiments, the 8H9 antibody comprises a heavy chain as set forth in one of SEQ ID NOs: 9-16 and a light chain as set forth in one of SEQ ID NOs: 1-8.

In some embodiments, any of the antibody agents disclosed herein competes with an 8H9 antibody for binding to B7H3.

The present invention provides a DNA or RNA encoding any of the antibody agents or fragments thereof disclosed herein.

The present invention provides a cell that expresses any of the antibody agents or fragments thereof disclosed herein.

The present invention provides a method of preparing a cell that expresses an antibody agent or fragment thereof, including transfecting or virally transducing the cell with a DNA or RNA encoding any of the antibody agents disclosed herein.

In some embodiments, the cell is virally transduced within a patient.

In some embodiments, the cell is an immune cell.

In some embodiments, the cell is an antigen-presenting cell.

In some embodiments, the cell is a T cell. In some embodiments, the cell is an NK cell.

The present invention provides a vaccine including any of the DNAs or RNAs disclosed herein.

The present invention provides a method of vaccinating a patient, including administering any of the vaccines disclosed herein to a patient in need thereof.

In some embodiments, the patient is canine or feline.

The present invention provides a chimeric antigen receptor including any of the antibody agents or fragments thereof disclosed herein.

In some embodiments, a DNA or RNA encodes a chimeric antigen receptor.

The present invention provides a cell expressing any of the chimeric antigen receptors disclosed herein (e.g., a T cell or an NK cell).

The present invention provides a method of preparing a cell including transfecting or virally transducing a cell with any of the DNAs or RNAs disclosed herein.

The present invention provides a method of adoptive cell therapy, including a step of administering a therapeutically effective amount of any of the cells disclosed herein to a patient in need thereof.

The present invention provides a method of treating a patient by targeting a peptide epitope set forth in SEQ ID NO.: 32, including administering any of the antibody agents or fragments thereof disclosed herein to a patient in need thereof.

In some embodiments, the patient is selected from the group of a human, a dog, a cat, a chimpanzee, an orangutan, a gibbon, a macaque, a marmoset, a pig, a horse, a panda, and an elephant.

The present invention provides a method of treating a patient including administering any of the cells disclosed herein to a patient in need thereof.

The present invention provides a method of treating a patient including administering a virus including a DNA or RNA encoding any of the antibody agents or fragments thereof disclosed herein to a patient in need thereof.

The present invention provides a method of treating a patient by compartmental radioimmunotherapy (cRIT), including administering any of the antibody agents or fragments thereof disclosed herein to a patient in need thereof.

In some embodiments, the antibody is administered intrathecally, intraperitoneally, or by convection enhanced delivery.

BRIEF DESCRIPTION OF THE DRAWING

The Drawing included herein, which is composed of the following Figures, is for illustration purposes only not for limitation.

BRIEF DESCRIPTION OF THE SEQUENCE LISTING

Figure 1:
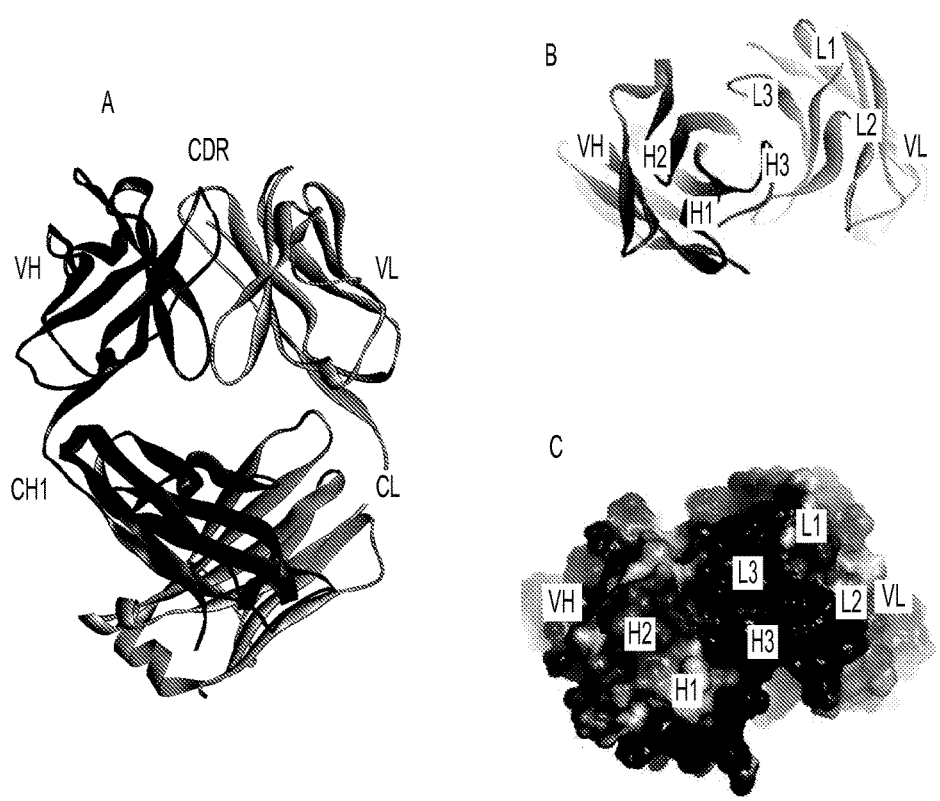
FIG. 1 shows a ribbon diagram of the crystal structure of ch8H9 Fab. A: Side view of Fab showing individual Ig domains and complementarity determining region (CDR). B: Top down view on antigen binding site, showing the orientation of the 6 CDR loops. C: Electrostatic surface potential of antigen binding site rendered from negatively charged (red) to positively charged (blue) in range from −1 to +1 kT/e.
Figure 2:
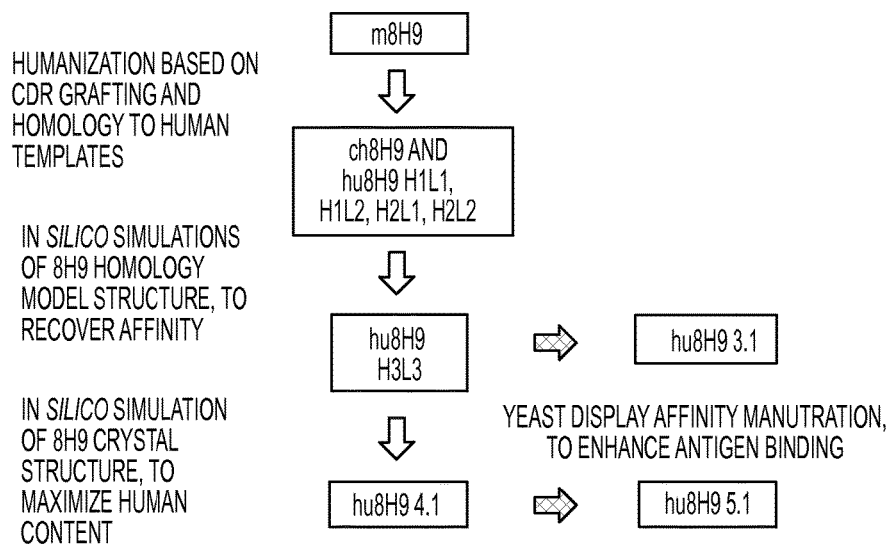
FIG. 2 illustrates a provided strategy for developing humanized and affinity matured 8H9 antibodies or antigen-binding fragments thereof.

```
SEQ ID NO.: 1 (ch8H9 Light chain) is
DIVMTQSPATLSVTPGDRVSLSCRASQSISDYLHWYQQKSHESPRLL

IKYASQSISGIPSRFSGSGSGSDFTLSINSVEPEDVGVYYCQNGHSF

PLTFGAGTKLELKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

SEQ ID NO.: 2 (hu8H9 L1 Light chain) is
EIVMTQSPATLSVSPGERVTLSCRASQSISDYLHWYQQKPGQAPRLL

IKYASQSISGIPARFSGSGSGTEFTLTISSVQPEDVGVYYCQNGHSF

PLTFGQGTKLEIKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

SEQ ID NO.: 3 (hu8H9 L2 Light chain) is
EIVMTQSPATLSVSPGERVTLSCRASQSISDYLHWYQQKSHESPRLL

IKYASQSISGIPARFSGSGSGTEFTLTINSVEPEDVGVYYCQNGHSF

PLTFGQGTKLEIKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

SEQ ID NO.: 4 (hu8H9 L3 Light chain) is
EIVMTQSPATLSVSPGERVSLSCRASQSISDYLHWYQQKSHESPRLL

IKYASQSISGIPARFSGSGSGSEFTLTINSVEPEDVGVYYCQNGHSF

PLTFGQGTKLELKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

SEQ ID NO.: 5 (hu8H9 3.1 Light chain) is
EIVMTQSPATLSVSPGERVTLSCRASQSISDYLYWYQQKSHESPRLL

IKYASQSISGIPARFSGSGSGSEFTLTINSVEPEDVGVYYCQNGHSF

PLTFGQGTKLELKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

SEQ ID NO.: 6 (hu8H9 4.1 Light chain) is
EIVMTQSPATLSVSPGERVTLSCRASQSISDYLHWYQQKSHQAPRLL

IKYASQSISGIPARFSGSGSGSEFTLTISSLQPEDFGVYYCQNGHSF

PLTFGQGTKLELKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

SEQ ID NO.: 7 (hu8H9 5.1 Light chain) is
EIVMTQSPATLSVSPGERVTLSCRASQSISDYLYWYQQKSHQAPRLL

IKYASQSISGIPARFSGSGSGSEFTLTISSLQPEDFGVYYCQNGHSF

PLTFGQGTKLELKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

SEQ ID NO.: 8 (ch8H9 6.1 Light chain; ch8H9 + 6
affinity maturation mutations) is
DIVMTQSPATLSVTPGDRVTLSCRASQSISDYLYWYQQKSHESPRLL

IKYASQSISGIPSRFSGSGSGSDFTLSINSVEPEDVGVYYCQNGHSF

PLTFGAGTKLELKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

SEQ ID NO.: 9 (ch8H9 Heavy chain) is
QVQLQQSGAELVKPGASVKLSCKASGYTFTNYDINWVRQRPEQGLEW

IGWIFPGDGSTQYNEKFKGKATLTTDTSSSTAYMQLSRLTSEDSAVY

FCARQTTATWFAYWGQGTLVTVSAASTKGPSVFPLAPSSKSTSGGTA

ALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPEL

LGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPGK

SEQ ID NO.: 10 (hu8H9 H1 Heavy chain) is
QVQLVQSGAEVKKPGASVKLSCKASGYTFTNYDINWVRQAPGQGLEW

IGWIFPGDGSTQYNEKFKGKATLTTDTSTSTAYMELSSLRSEDTAVY

FCARQTTATWFAYWGQGTLVTVSSASTKGPSVFPLAPSSKSTSGGTA
```

ALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPEL

LGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPGK

SEQ ID NO.: 11 (hu8H9 H2 Heavy chain) is
QVQLVQSGAEVVKPGASVKLSCKASGYTFTNYDINWVRQAPGQGLEW

IGWIFPGDGSTQYNEKFKGKATLTTDTSTSTAYMELSRLTSEDTAVY

FCARQTTATWFAYWGQGTLVTVSSASTKGPSVFPLAPSSKSTSGGTA

ALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPEL

LGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPGK

SEQ ID NO.: 12 (hu8H9 H3 Heavy chain) is
QVQLVQSGAEVVKPGASVKLSCKASGYTFTNYDINWVRQRPEQGLEW

IGWIFPGDGSTQYNEKFKGKATLTTDTSTSTAYMELSSLRSEDTAVY

FCARQTTATWFAYWGQGTLVTVSSASTKGPSVFPLAPSSKSTSGGTA

ALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPEL

LGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPGK

SEQ ID NO.: 13 (hu8H9 3.1 Heavy chain) is
QVQLVQSGAEVVKPGASVKLSCKTSGYTFTNYDINWVRQRPGQGLEW

IGWIFPGDDSTQYNEKFKGKATLTTDTSTSTAYMELSSLRSEDTAVY

FCARQTTGTWFAYWGQGTLVTVSSASTKGPSVFPLAPSSKSTSGGTA

ALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPEL

LGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPGK

SEQ ID NO.: 14 (hu8H9 4.1 Heavy chain) is
QVQLVQSGAEVVKPGASVKVSCKASGYTFTNYDINWVRQRPEQGLEW

IGWIFPGDGSTQYNEKFKGRVTMTTDTSTSTVYMELSSLRSEDTAVY

FCARQTTATWFAYWGQGTLVTVSSASTKGPSVFPLAPSSKSTSGGTA

ALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPEL

LGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPGK

SEQ ID NO.: 15 (hu8H9 5.1 Heavy chain) is
QVQLVQSGAEVVKPGASVKVSCKTSGYTFTNYDINWVRQRPGQGLEW

IGWIFPGDDSTQYNEKFKGRVTMTTDTSTSTVYMELSSLRSEDTAVY

FCARQTTGTWFAYWGQGTLVTVSSASTKGPSVFPLAPSSKSTSGGTA

ALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPEL

LGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPGK

SEQ ID NO.: 16 (ch8H9 6.1 Heavy chain; ch8H9 +
6 affinity maturation mutations) is
QVQLQQSGAELVKPGASVKLSCKTSGYTFTNYDINWVRQRPGQGLEW

IGWIFPGDDSTQYNEKFKGKATLTTDTSSSTAYMQLSRLTSEDSAVY

FCARQTTGTWFAYWGQGTLVTVSAASTKGPSVFPLAPSSKSTSGGTA

ALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPEL

LGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPGK

SEQ ID NO.: 17 (hu8H9 H3L3 scFv) is
QVQLVQSGAEVVKPGASVKLSCKASGYTFTNYDINWVRQRPEQGLEW

IGWIFPGDGSTQYNEKFKGKATLTTDTSTSTAYMELSSLRSEDTAVY

FCARQTTATWFAYWGQGTLVTVSSGGGGSGGGGSGGGGSEIVMTQSP

ATLSVSPGERVSLSCRASQSISDYLHWYQQKSHESPRLLIKYASQSI

SGIPARFSGSGSGSEFTLTINSVEPEDVGVYYCQNGHSFPLTFGQGT

KLELKR

SEQ ID NO.: 18 (hu8H9 clone S3.3 scFv) is
QVQLVQSGAEVVKPGASVKLSCKTSGYTFTNYDINWVRQRPGQGLEW
IGWIFPGDGSTQYNEKFKGKATLTTDTSTSTAYMELSSLRSEDTAVY
FCARQTTATWFAYWGQGTLVTVSSGGGGSGGGGSGGGGSEIVMTQSP
ATLSVSPGERVTLSCRASQSISDYLYWYQQKSHESPRLLIKYASQSI
SGIPARFSGSGSGSEFTLTINSVEPEDVGVYYCQNGHSFPLTFGQGT
KLELKR SEQ ID NO.: 19 (hu8H9 clone S7.2 scFv) is
QVQLVQSGAEVVKPGASCKLSCKTSGYTFTNYDINWVRQRPGQGLEW
IGWIFPGDGSTQYNEKFKGKATLTTDTSTSTAYMELSSLRSEDTAVY
FCARQTTATWFAYWGQGTLVTVSSGGGGSGGGGSGGVGSEIVMTQSP
ATLSVSPGERVTLSCRASQSIGDYLYWYQQKSHESPRLLIKYASQSI
SGIPARFSGSGSGSEFTLTINSVEPEDVGVYYCQNGHSFPLTFGQGT
KLELKR SEQ ID NO.: 20 (hu8H9 clone S7.17 scFv) is
QVQLVQSGAEVVKPGASVKLSCKTSGYTFTNYDINWVRQRPGQGLEW
VGWIFPGDGSTQYNEKFKGKATLTTDTSTSTAYMELSSLRSEDTAVY
FCARQTTSTWFAYWGQGTLVTVSSGGGGSGGGGSGGGGSEIVMTQSP
ATLSVSPGERVTLSCRASQPISDYLYWYQQKSHESPRLLIKYASQSI
SGIPARFSGSGSGSEFTLTINSVEPEDVGVYYCQNGYSFPLTFGQGT
KLELKR SEQ ID NO.: 21 (hu8H9 clone S7.22 scFv) is
QVQLVQSGAEVVKPGASVKLSCKTSGYTFTNYDINWVRQRPGQGLEW
IGWIFPGDDSTQYNEKFKGKATLTTDTSTSTAYMELSSLRPEDTAVY
FCARQTTGTWFAYWGQGTLVTVSSGGGGSGGGGSGGGGSEIVMTQSP
ATLSVSPGERVTLSCRASQSISDYLYWYQQKSHESPRLLIKYASQSI
PGIPARFSGSGSGSEFTLTINSVEPEDVGVYYCQNGHSFPLTFGQGT
KLELKR SEQ ID NO.: 22 (hu8H9 clone S7.28 scFv) is
QVQLVQSGAEVVKPGASVKLSCKTSGYTFTNYDINWVRQRPGQGLEW
IGWIFPGDGSTQYNEKFKGKATLTTDTSTSTAYMELSSLGSEDTAVY
FCTRQTTATWFAYWGQGTLVTVSSGGGGSGGGGSSGGGSEIVMTQSP
ATLSVSPGERVTLSCRASQSIGDYLYWYQQKSHESPRLLIKYASQSI
SGIPARFSGSGSGSEFTLTINSVEPEDVGVYYCQNGHSFPLTFGQGT
KLELKR SEQ ID NO.: 23 (hu8H9 clone S7.29 scFv) is
QVQLVQSGAEVVKPGASVKLSCKTSGYTFTNYDINWVRQRPGQGLEW
IGWIFPGDGSTQYNEKFKGKATLTTDTSTSTAYLELSSLGSEDTAVY
FCARQTTGTWFAYWGQGTLVTVSSGGGGSGGGGSGGGGSEIVMTQSP
ATLSVSPGERVTLSCRASQSISDYLYWYQQKSHESPRLLIKYASQSI
SGIPARFSGSGSGSEFTLTINSVEPEDVGVYYCQNGHSFPLTFGQGT
KLELKR SEQ ID NO.: 24 (hu8H9 3.1 scFv) is
QVQLVQSGAEVVKPGASVKLSCKTSGYTFTNYDINWVRQRPGQGLEW
IGWIFPGDDSTQYNEKFKGKATLTTDTSTSTAYMELSSLRSEDTAVY
FCARQTTGTWFAYWGQGTLVTVSSGGGGSGGGGSGGGGSEIVMTQSP
ATLSVSPGERVTLSCRASQSISDYLYWYQQKSHESPRLLIKYASQSI
SGIPARFSGSGSGSEFTLTINSVEPEDVGVYYCQNGHSFPLTFGQGT
KLELKR SEQ ID NO.: 25 (hu8H9 4.1 scFv) is
QVQLVQSGAEVVKPGASVKVSCKASGYTFTNYDINWVRQRPEQGLEW
IGWIFPGDGSTQYNEKFKGRVTMTTDTSTSTVYMELSSLRSEDTAVY
FCARQTTATWFAYWGQGTLVTVSSGGGGSGGGGSGGGGSEIVMTQSP
ATLSVSPGERVTLSCRASQSISDYLHWYQQKSHQAPRLLIKYASQSI
SGIPARFSGSGSGSEFTLTISSLQPEDFGVYYCQNGHSFPLTFGQGT
KLELKR SEQ ID NO.: 26 (hu8H9 5.1 scFv) is
QVQLVQSGAEVVKPGASVKVSCKTSGYTFTNYDINWVRQRPGQGLEW
IGWIFPGDDSTQYNEKFKGRVTMTTDTSTSTVYMELSSLRSEDTAVY
FCARQTTGTWFAYWGQGTLVTVSSGGGGSGGGGSGGGGSEIVMTQSP
ATLSVSPGERVTLSCRASQSISDYLYWYQQKSHQAPRLLIKYASQSI
SGIPARFSGSGSGSEFTLTISSLQPEDFGVYYCQNGHSFPLTFGQGT
KLELKR SEQ ID NO.: 27 (ch8H9 6.1 scFv) is
QVQLQQSGAELVKPGASVKLSCKTSGYTFTNYDINWVRQRPGQGLEW
IGWIFPGDDSTQYNEKFKGKATLTTDTSSSTAYMQLSRLTSEDSAVY
FCARQTTGTWFAYWGQGTLVTVSAGGGGSGGGGSGGGGSDIVMTQSP
ATLSVTPGDRVTLSCRASQSISDYLYWYQQKSHESPRLLIKYASQSI
SGIPSRFSGSGSGSDFTLSINSVEPEDVGVYYCQNGHSFPLTFGAGT
KLELKR SEQ ID NO.: 28 (linker huOKT3 (anti-CD3) scFv)
is
GGGGSGGGGSGGGGSQVQLVQSGGGVVQPGRSLRLSCKASGYTFTRY
TMHWVRQAPGKGLEWIGYINPSRGYTNYNQKFKDRFTISRDNSKNTA
FLQMDSLRPEDTGVYFCARYYDDHYCLDYWGQGTPVTVSSGGGGSGG
GGSGGGGSDIQMTQSPSSLSASVGDRVTITCSASSSVSYMNWYQQTP
GKAPKRWIYDTSKLASGVPSRFSGSGSGTDYTFTISSLQPEDIATYY
CQQWSSNPFTFGQGTKLQITR SEQ ID NO.: 29 (linker C825 (anti-DOTA) scFv)
is
GGGGSGGGGSGGGGSHVKLQESGPGLVQPSQSLSLTCTVSGFSLTDY
GVHWVRQSPGKGLEWLGVIWSGGGTAYNTALISRLNIYRDNSKNQVF
LEMNSLQAEDTAMYYCARRGSYPYNYFDAWGCGTTVTVSSGGGGSGG
GGSGGGGSQAVVIQESALTTPPGETVTLTCGSSTGAVTASNYANWVQ
EKPDHCFTGLIGGHNNRPPGVPARFSGSLIGDKAALTIAGTQTEDEA
IYFCALWYSDHWVIGGGTRLTVLG SEQ ID NO.: 30 (linker huOKT3 (anti-CD3) scFv) is
GGGGSGGGGSGGGGSQVQLVQSGGGVVQPGRSLRLSCKASGYTFTRY

TMHWVRQAPGKGLEWIGYINPSRGYTNYNQKFKDRFTISRDNSKNTA

FLQMDSLRPEDTGVYFCARYYDDHYCLDYWGQGTPVTVSSGGGGSGG

GGSGGGGSDIQMTQSPSSLSASVGDRVTITCSASSSVSYMNWYQQTP

GKAPKRWIYDTSKLASGVPSRFSGSGSGTDYTFTISSLQPEDIATYY

CQQWSSNPFTFGQGTKLQITR

SEQ ID NO.: 31 (linker C825 (anti-DOTA) scFv) is
GGGGSGGGGSGGGGSHVKLQESGPGLVQPSQSLSLTCTVSGFSLTDY

GVHWVRQSPGKGLEWLGVIWSGGGTAYNTALISRLNIYRDNSKNQVF

LEMNSLQAEDTAMYYCARRGSYPYNYFDAWGCGTTVTVSSGGGGSGG

GGSGGGGSQAVVIQESALTTPPGETVTLTCGSSTGAVTASNYANWVQ

EKPDHCFTGLIGGHNNRPPGVPARFSGSLIGDKAALTIAGTQTEDEA

IYFCALWYSDHWVIGGGTRLTVLG

SEQ ID NO.: 32 is IRDF

|  | CDRL1 | CDRL2 | CDRL3 |
|---|---|---|---|
| Kabat | | | |
| m8h9, ch8H9 Hu8H9 3.1, 5.1 | RASQSISDYLH SEQ ID NO.: 33 RASQSISDYLY SEQ ID NO.: 34 | YASQSIS SEQ ID NO.: 35 YASQSIS SEQ ID NO.: 36 | QNGHSFPLT SEQ ID NO.: 37 QNGHSFPLT SEQ ID NO.: 38 |
| Chothia | | | |
| m8h9, ch8H9 Hu8H9 3.1, 5.1 | SQSISDY SEQ ID NO.: 39 SQSISDY SEQ ID NO.: 40 | YAS SEQ ID NO.: 41 YAS SEQ ID NO.: 42 | GHSFPL SEQ ID NO.: 43 GHSFPL SEQ ID NO.: 44 |
| Honegger | | | |
| m8h9, ch8H9 Hu8H9 3.1, 5.1 | ASQSISDY SEQ ID NO.: 45 ASQSISDY SEQ ID NO.: 46 | YASQSISGIPSR SEQ ID NO.: 47 YASQSISGIPAR SEQ ID NO.: 48 | GHSFPL SEQ ID NO.: 49 GHSFPL SEQ ID NO.: 50 |
| IMGT | | | |
| m8h9, ch8H9 Hu8H9 3.1, 5.1 | QSISDY SEQ ID NO.: 51 QSISDY SEQ ID NO.: 52 | YAS SEQ ID NO.: 53 YAS SEQ ID NO.: 54 | QNGHSFPLT SEQ ID NO.: 55 QNGHSFPLT SEQ ID NO.: 56 |

|  | CDRH1 | CDRH2 | CDRH3 |
|---|---|---|---|
| Kabat | | | |
| m8h9, ch8H9 Hu8H9 3.1, 5.1 | NYDIN SEQ ID NO.: 57 NYDIN SEQ ID NO.: 58 | WIFPGDGSTQYNEK FKG SEQ ID NO.: 59 WIFPGDDSTQYNEK FKG SEQ ID NO.: 60 | QTTATWFAY SEQ ID NO.: 61 QTTGTWFAY SEQ ID NO.: 62 |
| Chothia | | | |
| m8h9, ch8H9 Hu8H9 3.1, 5.1 | GYTFTNY SEQ ID NO.: 63 GYTFTNY SEQ ID NO.: 64 | PGDG SEQ ID NO.: 65 PGDD SEQ ID NO.: 66 | TTATWFA SEQ ID NO.: 67 TTGTWFA SEQ ID NO.: 68 |
| Honegger | | | |
| m8h9, ch8H9 Hu8H9 3.1, 5.1 | ASGYTFTNYD SEQ ID NO.: 69 TSGYTFTNYD SEQ ID NO.: 70 | IFPGDGSTQYNEKF KGKA SEQ ID NO.: 71 IFPGDDSTQYNEKF KGRV SEQ ID NO.: 72 | QTTATWFA SEQ ID NO.: 73 QTTGTWFA SEQ ID NO.: 74 |
| IMGT | | | |
| m8h9, ch8H9 Hu8H9 3.1, 5.1 | GYTFTNYD SEQ ID NO.: 75 GYTFTNYD SEQ ID NO.: 76 | IFPGDGST SEQ ID NO.: 77 IFPGDDST SEQ ID NO.: 78 | ARQTTATWFAY SEQ ID NO.: 79 ARQTTGTWFAY SEQ ID NO.: 80 |

SEQ ID NO.: 81 is
TCAGTTTTGGCCCAGGCGGCC

SEQ ID NO.: 82 is
ACCACTAGTTGGGCCGGCCTG

SEQ ID NO.: 83 is
CTTCGCTGTTTTTCAATATTTTCTGTTATTGCTTCAGTTTTGGCCCA
GGCGGCC

SEQ ID NO.: 84 is
GAGCCGCCACCCTCAGAACCGCCACCCTCAGAGCCACCACTAGTTGG
GCCGGCCTG

SEQ ID NO.: 85 is
FVSIRDFG

SEQ ID NO.: 86 is
IQDF

DEFINITIONS

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

Administration: As used herein, the term "administration" refers to the administration of a composition to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal. In some embodiments, administration may involve intermittent dosing. In some embodiments, administration may involve continuous dosing (e.g., perfusion) for at least a selected period of time.

Affinity: As is known in the art, "affinity" is a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Agent: The term "agent" as used herein may refer to a compound or entity of any chemical class including, for example, polypeptides, nucleic acids, saccharides, lipids, small molecules, metals, or combinations thereof. As will be clear from context, in some embodiments, an agent can be or comprise a cell or organism, or a fraction, extract, or component thereof. In some embodiments, an agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention include small molecules, antibodies, antibody fragments, aptamers, nucleic acids (e.g., siRNAs, shRNAs, DNA/RNA hybrids, antisense oligonucleotides, ribozymes), peptides, peptide mimetics, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety.

Amino acid: As used herein, term "amino acid," in its broadest sense, refers to any compound and/or substance that can be incorporated into a polypeptide chain. In some embodiments, an amino acid has the general structure $H_2N—C(H)(R)—COOH$. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Animal: As used herein, the term "animal" refers to any member of the animal kingdom. In some embodiments, "animal" refers to humans, at any stage of development. In some embodiments, "animal" refers to non-human animals, at any stage of development. In some embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

Antagonist: As used herein, the term "antagonist" refers to an agent that i) inhibits, decreases or reduces the effects of another agent; and/or ii) inhibits, decreases, reduces, or delays one or more biological events. Antagonists may be or include agents of any chemical class including, for example, small molecules, polypeptides, nucleic acids, carbohydrates, lipids, metals, and/or any other entity that shows the relevant inhibitory activity. An antagonist may be direct (in which case it exerts its influence directly upon its target) or indirect (in which case it exerts its influence by other than binding to its target; e.g., by interacting with a regulator of the target, for example so that level or activity of the target is altered).

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen-binding site located at the tip of the Y structure. Amino acid sequence comparisons among antibody polypeptide chains have defined two light chain ($\kappa$ and $\lambda$) classes, several heavy chain (e.g., $\mu$, $\gamma$, $\alpha$, $\epsilon$, $\delta$) classes, and certain heavy chain subclasses ($\alpha$1, $\alpha$2, $\gamma$1, $\gamma$2, $\gamma$3, and $\gamma$4). Antibody classes (IgA [including IgA1, IgA2], IgD, IgE, IgG [including IgG1, IgG2, IgG3, IgG4], IgM) are defined based on the class of the utilized heavy chain sequences. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc., as is known in the art. Moreover, the term "antibody" as used herein, will be understood to refer to in appropriate embodiments (unless otherwise stated or clear from context) to any of the art-known or developed constructs or formats for capturing antibody structural and functional features in alternative presentation. For example, in some embodiments, the term can refer to bi- or other multi-specific (e.g., zybodies, etc.) antibodies, Small Modular ImmunoPharmaceuticals ("SMIPs™"), single chain antibodies (scAbs), cameloid antibodies, and/or antibody fragments. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc.]), or other pendant group (e.g., poly-ethylene glycol, etc.).

Antibody agent: As used herein, the term "antibody agent" refers to an agent that specifically binds to a particular antigen. In some embodiments, the term encompasses any polypeptide with immunoglobulin structural elements sufficient to confer specific binding. Suitable antibody agents include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, and antibody fragments. As used herein, the term "antibody agent" also includes intact monoclonal antibodies, polyclonal antibodies, single domain antibodies (e.g., shark single domain antibodies (e.g., IgNAR or fragments thereof)), multispecific antibodies (e.g. bi-specific antibodies) formed from at least two intact antibodies, and antibody fragments so long as they exhibit the desired biological activity. In some embodiments, the term encompasses stapled peptides. In some embodiments, the term encompasses one or more antibody-like binding peptidomimetics. In some embodiments, the term encompasses one or more antibody-like binding scaffold proteins. In come embodiments, the term encompasses monobodies or adnectins. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain. The term antibody agent includes chimeric antigen receptors.

Antibody fragment: As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and multi specific antibodies formed from antibody fragments. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. In many embodiments, an antibody fragment contains sufficient sequence of the parent antibody of which it is a fragment that it binds to the same antigen as does the parent antibody; in some embodiments, a fragment binds to the antigen with a comparable affinity to that of the parent antibody and/or competes with the parent antibody for binding to the antigen. Examples of antigen binding fragments of an antibody include, but are not limited to, Fab fragment, Fab' fragment, F(ab')2 fragment, scFv fragment, Fv fragment, dsFv diabody, dAb fragment, Fd' fragment, Fd fragment, and an isolated complementarity determining region (CDR) region. An antigen-binding fragment of an antibody may be produced by any means. For example, an antigen-binding fragment of an antibody may be enzymatically or chemically produced by fragmentation of an intact antibody and/or it may be recombinantly produced from a gene encoding the partial antibody sequence. Alternatively or additionally, antigen-binding fragment of an antibody may be wholly or partially synthetically produced. An antigen-binding fragment of an antibody may optionally comprise a single chain antibody fragment. Alternatively or additionally, an antigen-binding fragment of an antibody may comprise multiple chains that are linked together, for example, by disulfide linkages. An antigen-binding fragment of an antibody may optionally comprise a multi-molecular complex. A functional antibody fragment typically comprises at least about 50 amino acids and more typically comprises at least about 200 amino acids.

Antibody polypeptide: As used herein, the terms "antibody polypeptide" or "antibody", or "antigen-binding fragment thereof", which may be used interchangeably, refer to polypeptide(s) capable of binding to an epitope. In some embodiments, an antibody polypeptide is a full-length antibody, and in some embodiments, is less than full length but includes at least one binding site (comprising at least one, and preferably at least two sequences with structure of antibody "variable regions"). In some embodiments, the term "antibody polypeptide" encompasses any protein having a binding domain, which is homologous or largely homologous to an immunoglobulin-binding domain. In particular embodiments, "antibody polypeptides" encompasses polypeptides having a binding domain that shows at least 99% identity with an immunoglobulin-binding domain. In some embodiments, "antibody polypeptide" is any protein having a binding domain that shows at least 70%, 80%, 85%, 90%, or 95% identity with an immunoglobulin-binding domain, for example a reference immunoglobulin-binding domain. An included "antibody polypeptide" may have an amino acid sequence identical to that of an antibody that is found in a natural source. Antibody polypeptides in accordance with the present invention may be prepared by any available means including, for example, isolation from a natural source or antibody library, recombinant production in or with a host system, chemical synthesis, etc., or combinations thereof. An antibody polypeptide may be monoclonal or polyclonal. An antibody polypeptide may be a member of any immunoglobulin class, including any of the human classes: IgG, IgM, IgA, IgD, and IgE. In certain embodiments, an antibody may be a member of the IgG immunoglobulin class. As used herein, the terms "antibody polypeptide" or "characteristic portion of an antibody" are used interchangeably and refer to any derivative of an antibody that possesses the ability to bind to an epitope of interest. In certain embodiments, the "antibody polypeptide" is an antibody fragment that retains at least a significant portion of the full-length antibody's specific binding ability. Examples of antibody fragments include, but are not limited to, Fab, Fab', F(ab')2, scFv, Fv, dsFv diabody, and Fd fragments. Alternatively or additionally, an antibody fragment may comprise multiple chains that are linked together, for example, by disulfide linkages. In some embodiments, an antibody polypeptide may be a human antibody. In some embodiments, the antibody polypeptides may be a humanized. Humanized antibody polypeptides include may be chimeric immunoglobulins, immunoglobulin chains or antibody polypeptides (such as Fv, Fab, Fab', F(ab')2 or other antigen-binding subsequences of antibodies) that contain minimal sequence derived from non-human immunoglobulin. In general, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity.

Antigen: An "antigen" is a molecule or entity that i) elicits an immune response; and/or (ii) is specifically bound by a T cell receptor (e.g., when presented by an MHC molecule) or an antibody (e.g., produced by a B cell), for example when exposed or administered to an organism. In some embodiments, an antigen elicits a humoral response (e.g., including production of antigen-specific antibodies) in an organism; alternatively or additionally, in some embodiments, an antigen elicits a cellular response (e.g., involving T-cells whose receptors specifically interact with the antigen) in an organism. It will be appreciated by those skilled in the art that a particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In general, an antigen may be or include any chemical entity such as, for example, a small molecule, a nucleic acid, a polypeptide, a carbohydrate, a lipid, a polymer [in some embodiments other than a biologic polymer (e.g., other than a nucleic acid or amino acid polymer)] etc. In some embodiments, an antigen is or comprises a polypeptide. In some embodiments, an antigen is or comprises a glycan. Those of ordinary skill in the art will appreciate that, in general, an antigen may be provided or utilized in isolated or pure form, or alternatively may be provided in crude form (e.g., together with other materials, for example in an extract such as a cellular extract or other relatively crude preparation of an antigen-containing source). In some embodiments, an antigen is or comprises a recombinant antigen. In some embodiments, an antigen is or comprises a polypeptide or portion thereof. In some embodiments, an antigen is associated with (e.g., expressed by) an infectious agent. In some embodiments, an antigen is associated with cancer (e.g., with tumor cells and/or metastases).

Antigen-binding fragment: The term "antigen-binding fragment", as used herein, refers to one or more fragments of an antibody that retain the ability to bind to an antigen. It has been shown that the antigen-binding function of an antibody can be performed by fragments of an intact antibody. Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; (vi) an isolated complementarity determining region (CDR), e.g., VH CDR3 comprising or not additional sequence (linker, framework region(s) etc.) and (vii) a combination of two to six isolated CDRs comprising or not additional sequence (linker, framework region(s) etc.). Furthermore, although the two domains of the Fv fragment, VL and VH, are coded for by separate genes, they can be joined, using recombinant methods, by a synthetic linker that enables them to be made as a single polypeptide chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85:5879-5883). Such single chain antibodies are also intended to be encompassed within the term "antigen-binding fragment" of an antibody. Furthermore, the antigen-binding fragments include binding-domain immunoglobulin fusion proteins comprising (i) a binding domain polypeptide (such as a heavy chain variable region, a light chain variable region, or a heavy chain variable region fused to a light chain variable region via a linker peptide) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The hinge region may be modified by replacing one or more cysteine residues with serine residues so as to prevent dimerization. Such binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies. Furthermore, the antigen-binding fragments include divalent (or bivalent) single-chain variable fragments (di-scFvs, bi-scFvs) or, alternatively, so-called diabodies that can be engineered by standard molecular biological means.

Antigen presenting cell: The phrase "antigen presenting cell" or "APC," as used herein, has its art understood meaning referring to cells which process and present antigens to T-cells. cells. Exemplary antigen cells include dendritic cells, macrophages and certain activated epithelial cells.

Antigenic Identity: as used herein, the term "antigenic identity" (AI) refers to the percentage fraction of amino acids in a polypeptide of interest, or portion thereof [e.g., in an HA polypeptide, or in an epitope (e.g., an immunodominant epitope) thereof], that are shared with a relevant reference polypeptide (e.g., a parent HA polypeptide that may, for example, be a pandemic HA), or portion thereof. The AI value resulting from comparison of any two polypeptides or sequences can be a number between 0 and 100, with a value of 100 indicating the two polypeptides, or portions thereof, are identical in sequence.

Approximately: As used herein, the terms "approximately" and "about" are each intended to encompass normal statistical variation as would be understood by those of ordinary skill in the art as appropriate to the relevant context. In certain embodiments, the terms "approximately" or "about" each refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of a stated value, unless otherwise stated or otherwise evident from the context (e.g., where such number would exceed 100% of a possible value).

Associated with: Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility of the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biologically active: As used herein, the phrase "biologically active" refers to a substance that has activity in a biological system (e.g., in a cell (e.g., isolated, in culture, in a tissue, in an organism), in a cell culture, in a tissue, in an organism, etc.). For instance, a substance that, when administered to an organism, has a biological effect on that organism, is considered to be biologically active. It will be appreciated by those skilled in the art that often only a portion or fragment of a biologically active substance is required (e.g., is necessary and sufficient) for the activity to be present; in such circumstances, that portion or fragment is considered to be a "biologically active" portion or fragment.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Binding agent: In general, the term "binding agent" is used herein to refer to any entity that binds to a target of interest as described herein. In many embodiments, a binding agent of interest is one that binds specifically with its target in that it discriminates its target from other potential binding partners in a particular interaction context. In general, a binding agent may be or comprise an entity of any chemical class (e.g., polymer, non-polymer, small molecule, polypeptide, carbohydrate, lipid, nucleic acid, etc.). In some embodiments, a binding agent is a single chemical entity. In some embodiments, a binding agent is a complex of two or more discrete chemical entities associated with one another under relevant conditions by non-covalent interactions. For example, those skilled in the art will appreciate that in some embodiments, a binding agent may comprise a "generic" binding moiety (e.g., one of biotin/avidin/streptavidin and/or a class-specific antibody) and a "specific" binding moiety (e.g., an antibody or aptamers with a particular molecular target) that is linked to the partner of the generic biding moiety. In some embodiments, such an approach can permit modular assembly of multiple binding agents through linkage of different specific binding moieties with the same generic binding moiety partner. In some embodiments, binding agents are or comprise polypeptides (including, e.g., antibodies or antibody fragments). In some embodiments, binding agents are or comprise small molecules. In some embodiments, binding agents are or comprise nucleic acids. In some embodiments, binding agents are aptamers. In some embodiments, binding agents are polymers; in some embodiments, binding agents are not polymers. In some embodiments, binding agents are non-polymeric in that they lack polymeric moieties. In some embodiments, binding agents are or comprise carbohydrates. In some embodiments, binding agents are or comprise lectins. In some embodiments, binding agents are or comprise peptidomimetics. In some embodiments, binding agents are or comprise scaffold proteins. In some embodiments, binding agents are or comprise mimeotopes. In some embodiments, binding agents are or comprise stapled peptides. In certain embodiments, binding agents are or comprise nucleic acids, such as DNA or RNA.

Characteristic portion: As used herein, the term "characteristic portion" is used, in the broadest sense, to refer to a portion of a substance whose presence (or absence) correlates with presence (or absence) of a particular feature, attribute, or activity of the substance. In some embodiments, a characteristic portion of a substance is a portion that is found in the substance and in related substances that share the particular feature, attribute or activity, but not in those that do not share the particular feature, attribute or activity. In certain embodiments, a characteristic portion shares at least one functional characteristic with the intact substance. For example, in some embodiments, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance. In some embodiments, a characteristic portion may be biologically active.

Characteristic sequence: A "characteristic sequence" is a sequence that is found in all members of a family of polypeptides or nucleic acids, and therefore can be used by those of ordinary skill in the art to define members of the family.

Characteristic sequence element: As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of the polymer. In some embodiments, presence (or absence) of a characteristic sequence element defines a particular polymer as a member (or not a member) of a particular family or group of such polymers. A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of contiguous monomers spaced apart by one or more spacer regions whose length may or may not vary across polymers that share the sequence element.

Chimeric antigen receptors/adoptive cell therapy: Antibody agents of the present invention, including ingle chain variable fragments (scFv), may be used for the preparation of chimeric antigen receptors, the preparation and use of which is generally known in the art. A chimeric antigen receptor (CAR) typically is an artificially constructed hybrid protein or polypeptide containing an antigen binding domain of a scFv, or other antibody agent, linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Chimeric antigen receptors may be used for therapeutic treatment, including for example for adoptive cell therapy. Adoptive cell therapy is a therapeutic approach which typically includes isolation and ex vivo expansion and/or manipulation of immune cells, often T cells, and subsequent administration of these cells to patients, for example for the treatment of cancer. Administered cells may be autologous or allogeneic. Cells may be manipulated to express chimeric antigen receptors in any one of the known ways, including, for example, by using RNA and DNA transfection, both of which technologies are known in the art.

Combination therapy: The term "combination therapy", as used herein, refers to those situations in which two or more different pharmaceutical or therapeutic agents are administered in overlapping or sequential regimens so that the subject is simultaneously or sequentially exposed to both agents. By "in combination with," it is not intended to imply that the agents must be administered at the same time and/or formulated for delivery together, although these methods of delivery are within the scope of the invention. Compositions of the invention can be administered concurrently with, prior to, or subsequent to, one or more other desired therapeutics or medical procedures. In will be appreciated that therapeutically active agents utilized in combination may be administered together in a single composition or administered separately in different compositions. In general, each agent will be administered at a dose and/or on a time schedule determined for that agent.

Comparable: The term "comparable", as used herein, refers to two or more agents, entities, situations, sets of conditions, etc. that may not be identical to one another but that are sufficiently similar to permit comparison there between so that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Corresponding to: As used herein, the term "corresponding to" is often used to designate a structural element or moiety in an agent of interest that shares a position (e.g., in three-dimensional space or relative to another element or moiety) with one present in an appropriate reference agent. For example, in some embodiments, the term is used to refer to position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the 190th residue in the first polymer but rather corresponds to the residue found at the 190th position in the reference polymer; those of ordinary skill in the art readily appreciate how to identify "corresponding" amino acids, including through use of one or more commercially-available algorithms specifically designed for polymer sequence comparisons.

Derivative: As used herein, the term "derivative" refers to a structural analogue of a reference substance. That is, a "derivative" is a substance that shows significant structural similarity with the reference substance, for example sharing a core or consensus structure, but also differs in certain discrete ways. In some embodiments, a derivative is a substance that can be generated from the reference substance by chemical manipulation. In some embodiments, a derivative is a substance that can be generated through performance of a synthetic process substantially similar to (e.g., sharing a plurality of steps with) one that generates the reference substance.

Detection entity/agent: The term "detection entity" or "detection agent" as used herein refers to any element, molecule, functional group, compound, fragment or moiety that is detectable. In some embodiments, a detection entity is provided or utilized alone. In some embodiments, a detection entity is provided and/or utilized in association with (e.g., joined to) another agent. Examples of detection entities include, but are not limited to: various ligands, radionuclides (e.g., 3H, 14C, 18F, 19F, 32P, 35S, 1351, 1251, 1231, 64Cu, 187Re, 111In, 90Y, 99mTc, 177Lu, 89Zr etc.), fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

Determine: Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Dosage form: As used herein, the term "dosage form" refers to a physically discrete unit of an active agent (e.g., a therapeutic or diagnostic agent) for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

Engineered: In general, the term "engineered" refers to the aspect of having been manipulated by the hand of man. For example, a polynucleotide is considered to be "engineered" when two or more sequences, that are not linked together in that order in nature, are manipulated by the hand of man to be directly linked to one another in the engineered polynucleotide. For example, in some embodiments of the present invention, an engineered polynucleotide comprises a regulatory sequence that is found in nature in operative association with a first coding sequence but not in operative association with a second coding sequence, is linked by the hand of man so that it is operatively associated with the second coding sequence. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity.

Epitope: As used herein, the term "epitope" has its meaning as understood in the art. It will be appreciated by those of ordinary skill in the art that an epitope, also known as antigenic determinant, is a molecular region of an antigen that is recognized by the immune system, specifically by antibodies, B cells, or T cells. It will be further appreciated that epitopes can be composed of sugars, lipids, or amino acids. The epitopes of protein antigens are divided into two categories, conformational epitopes and linear epitopes, based on their structure and interaction with the paratope (part of an antibody that recognizes the epitope). A conformational epitope is composed of discontinuous sections of the antigen's amino acid sequence and these epitopes interact with the paratope based on the 3-D surface features and shape or tertiary structure of the antigen. Linear epitopes interact with the paratope based on their primary structure and a linear epitope is formed by a continuous sequence of amino acids from the antigen.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Functional: As used herein, a "functional" biological molecule is a biological molecule in a form in which it exhibits a property and/or activity by which it is characterized. A biological molecule may have two functions (i.e., bifunctional) or many functions (i.e., multifunctional).

Fragment: A "fragment" of a material or entity as described herein has a structure that includes a discrete portion of the whole, but lacks one or more moieties found in the whole. In some embodiments, a fragment consists of such a discrete portion. In some embodiments, a fragment consists of or comprises a characteristic structural element or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer. The whole material or entity may in some embodiments be referred to as the "parent" of the whole.

Gene: As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as tRNAs, RNAi-inducing agents, etc. For the purpose of clarity we note that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a protein-coding nucleic acid.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

High affinity binding: The term "high affinity binding", as used herein refers to a high degree of tightness with which a particular ligand binds to its partner. Affinities can be measured by any available method, including those known in the art. In some embodiments, binding is considered to be high affinity if the Kd is about 500 pM or less (e.g., below about 400 pM, about 300 pM, about 200 pM, about 100 pM, about 90 pM, about 80 pM, about 70 pM, about 60 pM, about 50 pM, about 40 pM, about 30 pM, about 20 pM, about 10 pM, about 5 pM, about 4 pM, about 3 pM, about 2 pM, etc.) in binding assays. In some embodiments, binding is considered to be high affinity if the affinity is stronger (e.g., the Kd is lower) for a polypeptide of interest than for a selected reference polypeptide. In some embodiments, binding is considered to be high affinity if the ratio of the Kd for a polypeptide of interest to the Kd for a selected reference polypeptide is 1:1 or less (e.g., 0.9:1, 0.8:1, 0.7:1, 0.6:1, 0.5:1. 0.4:1, 0.3:1, 0.2:1, 0.1:1, 0.05:1, 0.01:1, or less). In some embodiments, binding is considered to be high affinity if the Kd for a polypeptide of interest is about 100% or less (e.g., about 99%, about 98%, about 97%, about 96%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1% or less) of the Kd for a selected reference polypeptide.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution. Typical amino acid categorizations are summarized below:

| | | | | | |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences. Representative algorithms and computer programs useful in determining the percent homology between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent homology between two nucleotide sequences can, alternatively, be determined for example using the GAP program in the GCG software package using an NWSgapdna.CMP matrix.

Human: In some embodiments, a human is an embryo, a fetus, an infant, a child, a teenager, an adult, or a senior citizen.

Hydrophilic: As used herein, the term "hydrophilic" and/or "polar" refers to a tendency to mix with, or dissolve easily in, water.

Hydrophobic: As used herein, the term "hydrophobic" and/or "non-polar", refers to a tendency to repel, not combine with, or an inability to dissolve easily in, water.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Isolated: As used herein, the term "isolated" refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. In some embodiments, isolation involves or requires disruption of covalent bonds (e.g., to isolate a polypeptide domain from a longer polypeptide and/or to isolate a nucleotide sequence element from a longer oligonucleotide or nucleic acid).

Marker: A marker, as used herein, refers to an entity or moiety whose presence or level is a characteristic of a particular state or event. In some embodiments, presence or level of a particular marker may be characteristic of presence or stage of a disease, disorder, or condition. To give but one example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present invention a useful marker need not distinguish tumors of a particular subclass with 100% accuracy.

Mutant: As used herein, the term "mutant" refers to an entity that shows significant structural identity with a reference entity but differs structurally from the reference entity in the presence or level of one or more chemical moieties as compared with the reference entity. In many embodiments, a mutant also differs functionally from its reference entity. In general, whether a particular entity is properly considered to be a "mutant" of a reference entity is based on its degree of structural identity with the reference entity. As will be appreciated by those skilled in the art, any biological or chemical reference entity has certain characteristic structural elements. A mutant, by definition, is a distinct chemical entity that shares one or more such characteristic structural elements. To give but a few examples, a small molecule may have a characteristic core structural element (e.g., a macrocycle core) and/or one or more characteristic pendent moieties so that a mutant of the small molecule is one that shares the core structural element and the characteristic pendent moieties but differs in other pendent moieties and/or in types of bonds present (single vs. double, E vs. Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a mutant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a mutant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a mutant polypeptide does not share at least one characteristic sequence element with a reference polypeptide. In some embodiments, the reference polypeptide has one or more biological activities. In some embodiments, a mutant polypeptide shares one or more of the biological activities of the reference polypeptide. In some embodiments, a mutant polypeptide lacks one or more of the biological activities of the reference polypeptide. In some embodiments, a mutant polypeptide shows a reduced level of one or more biological activities as compared with the reference polypeptide.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2′-fluororibose, ribose, 2′-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long.

Patient: As used herein, the term "patient" or "subject" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). As those skilled in the art will appreciate, in some embodiments, an animal may be a domestic animal (e.g., a farm animal, a companion animal, etc.) In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, such cancer or tumor is or comprises a cancer of the prostate, or tumor in the prostate. In some embodiments, the disorder or condition is metastatic cancer.

Peptide: The term "peptide" refers to two or more amino acids joined to each other by peptide bonds or modified peptide bonds. In particular embodiments, "peptide" refers to a polypeptide having a length of less than about 100 amino acids, less than about 50 amino acids, less than 20 amino acids, or less than 10 amino acids.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: The term "pharmaceutically acceptable" as used herein, refers to agents that, within the scope of sound medical judgment, are suitable for use in contact with tissues of human beings and/or animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Polypeptide: The term "polypeptide", as used herein, generally has its art-recognized meaning of a polymer of at least three amino acids, linked to one another by peptide bonds. In some embodiments, the term is used to refer to specific functional classes of polypeptides. For each such class, the present specification provides several examples of amino acid sequences of known exemplary polypeptides within the class; in some embodiments, such known polypeptides are reference polypeptides for the class. In such embodiments, the term "polypeptide" refers to any member of the class that shows significant sequence homology or identity with a relevant reference polypeptide. In many embodiments, such member also shares significant activity with the reference polypeptide. Alternatively or additionally, in many embodiments, such member also shares a particular characteristic sequence element with the reference polypeptide (and/or with other polypeptides within the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (i.e., a conserved region that may in some embodiments may be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide. In some embodiments, a polypeptide may comprise natural amino acids, non-natural amino acids, or both. In some embodiments, a polypeptide may comprise only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups, e.g., modifying or attached to one or more amino acid side chains, and/or at the polypeptide's N-terminus, the polypeptide's C-terminus, or both. In some embodiments, a polypeptide may be cyclic. In some embodiments, a polypeptide is not cyclic. In some embodiments, a polypeptide is linear.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Pure: As used herein, an agent or entity is "pure" if it is substantially free of other components. For example, a preparation that contains more than about 90% of a particular agent or entity is typically considered to be a pure preparation. In some embodiments, an agent or entity is at least 91%, at least 92%, at least 93%, at least 94%, at least 95%, at least 96%, at least 97%, at least 98%, or at least 99% pure.

Reference: The term "reference" is often used herein to describe a standard or control agent, individual, population, sample, sequence or value against which an agent, individual, population, sample, sequence or value of interest is compared. In some embodiments, a reference agent, individual, population, sample, sequence or value is tested and/or determined substantially simultaneously with the testing or determination of the agent, individual, population, sample, sequence or value of interest. In some embodiments, a reference agent, individual, population, sample, sequence or value is a historical reference, optionally embodied in a tangible medium. Typically, as would be understood by those skilled in the art, a reference agent, individual, population, sample, sequence or value is determined or characterized under conditions comparable to those utilized to determine or characterize the agent, individual, population, sample, sequence or value of interest.

Response: As used herein, a response to treatment may refer to any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. It may refer to a subject's response or to a tumor's response. Tumor or subject response may be measured according to a wide variety of criteria, including clinical criteria and objective criteria. Techniques for assessing response include, but are not limited to, clinical examination, positron emission tomography, chest X-ray CT scan, MRI, ultrasound, endoscopy, laparoscopy, presence or level of tumor markers in a sample obtained from a subject, cytology, and/or histology. Many of these techniques attempt to determine the size of a tumor or otherwise determine the total tumor burden. Methods and guidelines for assessing response to treatment are discussed in Therasse et. al., "New guidelines to evaluate the response to treatment in solid tumors", European Organization for Research and Treatment of Cancer, National Cancer Institute of the United States, National Cancer Institute of Canada, J. Natl. Cancer Inst., 2000, 92(3):205-216. The exact response criteria can be selected in any appropriate manner, provided that when comparing groups of tumors and/or patients, the groups to be compared are assessed based on the same or comparable criteria for determining response rate. One of ordinary skill in the art will be able to select appropriate criteria.

Specific binding: As used herein, the terms "specific binding" or "specific for" or "specific to" refer to an interaction (typically non-covalent) between a target entity (e.g., a target protein or polypeptide) and a binding agent (e.g., an antibody, such as a provided antibody). As will be understood by those of ordinary skill, an interaction is considered to be "specific" if it is favored in the presence of alternative interactions. In many embodiments, an interaction is typically dependent upon the presence of a particular structural feature of the target molecule such as an antigenic determinant or epitope recognized by the binding molecule. For example, if an antibody is specific for epitope A, the presence of a polypeptide containing epitope A or the presence of free unlabeled A in a reaction containing both free labeled A and the antibody thereto, will reduce the amount of labeled A that binds to the antibody. It is to be understood that specificity need not be absolute. For example, it is well known in the art that numerous antibodies cross-react with other epitopes in addition to those present in the target molecule. Such cross-reactivity may be acceptable depending upon the application for which the antibody is to be used. In particular embodiments, an antibody specific for receptor tyrosine kinases has less than 10% cross-reactivity with receptor tyrosine kinase bound to protease inhibitors (e.g., ACT). One of ordinary skill in the art will be able to select antibodies having a sufficient degree of specificity to perform appropriately in any given application (e.g., for detection of a target molecule, for therapeutic purposes, etc.). Specificity may be evaluated in the context of additional factors such as the affinity of the binding molecule for the target molecule versus the affinity of the binding molecule for other targets (e.g., competitors). If a binding molecule exhibits a high affinity for a target molecule that it is desired to detect and low affinity for non-target molecules, the antibody will likely be an acceptable reagent for immunodiagnostic purposes. Once the specificity of a binding molecule is established in one or more contexts, it may be employed in other, preferably similar, contexts without necessarily re-evaluating its specificity.

Specificity: As is known in the art, "specificity" is a measure of the ability of a particular ligand to distinguish its binding partner from other potential binding partners.

Subject: By "subject" is meant a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. A subject can be a patient, which refers to a human presenting to a medical provider for diagnosis or treatment of a disease. In some embodiments, a subject is an individual to whom therapy is administered.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial sequence homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized below:

| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |

-continued

| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul, et al., "Gapped BLAST and PSI-BLAST: a new generation of protein database search programs", Nucleic Acids Res. 25:3389-3402, 1997; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are homologous over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul et al., Nucleic Acids Res. 25:3389-3402, 1997; Baxevanis et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial structural similarity: As used herein, the term "substantial structural similarity" refers to presence of shared structural features such as presence and/or identity of particular amino acids at particular positions (see definitions of "shared sequence homology" and "shared sequence identity"). In some embodiments the term "substantial structural similarity" refers to presence and/or identity of structural elements (for example: loops, sheets, helices, H-bond donors, H-bond acceptors, glycosylation patterns, salt bridges, and disulfide bonds). In some other embodiments, the term "substantial structural similarity" refers to three-dimensional arrangement and/or orientation of atoms or moieties relative to one another (for example: distance and/or angles between or among them between an agent of interest and a reference agent).

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutic regimen: A "therapeutic regimen", as that term is used herein, refers to a dosing regimen whose administration across a relevant population is correlated with a desired or beneficial therapeutic outcome.

Therapeutically effective amount: As used herein, the term "therapeutically effective amount" means an amount that is sufficient, when administered to a subject suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

Treatment: As used herein, the term "treatment" (also "treat" or "treating"), in its broadest sense, refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be administered to a subject who does not exhibit signs of the relevant disease, disorder and/or condition and/or of a subject who exhibits only early signs of the disease, disorder, and/or condition. Alternatively or additionally, in some embodiments, treatment may be administered to a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Treatment by in vivo expression of antibodies: Lymphoid and non-lymphoid cells (e.g., myoblasts, mesenchymal stem cells) can be genetically engineered ex vivo or in vivo to secrete full-length IgG (Compte et al., 2013 Biomatter 3; Noel et al., 1997 Hum Gene Ther 8: 1219-1229. IgG gene therapy using recombinant adenovirus carrying the DNA sequences could achieve high serum IgG levels, but durability was limited by virus immunogenicity (Noel et al., 2002 Hum Gene Ther 13:1483-1493; Jooss & Chirmule, 2004 Gene Ther 10:955-963). Adeno-associated viruses (rAAV), and especially selective serotypes are less immunogenic (Xiao et al., 2012 Therapeutic Delivery 3:835-856), and are proven durable vectors for human gene therapy (Nathwani et al., 2011, N. Engl. J. Med. 365:2357-2365; Patel et al., 2014 International Journal of Hematology 99:372-376). Preclinical proofs of concept have been reported for full length IgG antibodies specific for VEGFR-2 (DC101) (Fang et al., 2005 Nat. Biotechnol. 23:584-590), VEGF (Watanabe et al., 2009 Hum. Gene Ther. 20:598-610), HER-2 (Ho et al., 2009 Cancer Gene Ther. 16:184-194; Wang et al., 2010 Cancer Gene Ther. 17, 559-570), Met (Vigna et al., 2008 Cancer Res. 68:9176-9183), and HIV (Balazs et al., 2012 Nature 481:81-84). Similar successes have been described for single chain Fv fragment (scFv) against angiogenesis-associated laminin (Arafat et al., 2002 Gene Ther 9:256-262; Sanz et al., 2001 Cancer Immunol. Immunother. 50:557-565; Sanz et al., 2003 EMBO J. 22:1508-1517; Sanz et al., 2002 Gene Ther. 9:1049-1053) and its trivalent and hexavalent forms (Sanchez-Arevalo et al., 2006 Int. J. Cancer 119:455-462), or scFv against VEGF (Afanasieva et al., 2003 Gene Ther. 10:1850-1859) and its bivalent derivatives (minibody and scFv-Fc), or scFv anti-HER2 immunotoxin (Liu et al., 2009 Cancer Gene Ther. 16:861-872), or CEAxCD3 bispecific diabodies (Blanco et al, 2007 J. Immunol. 171:1070-1077; Compte et al., 2007 Cancer Gene Ther. 14:380-388).

Variant: As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs. double, E vs. Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

Vector: As used herein, "vector" refers to a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

Wild type: As used herein, the term "wild type" has its art-understood meaning that refers to an entity having a structure and/or activity as found in nature in a "normal" (as contrasted with mutant, diseased, altered, etc.) state or context. Those of ordinary skill in the art will appreciate that wild type genes and polypeptides often exist in multiple different forms (e.g., alleles).

DETAILED DESCRIPTION OF CERTAIN EMBODIMENTS

Relieving Immune Suppression

The removal of negative regulatory pathways that inhibit immune cells is rapidly gaining importance in cancer treatment. One of the earliest successful examples of such a therapeutic approach was embodied in the Food and Drug Administration's (FDA's) March 2001 approval of ipilimumab for the treatment of melanoma. Ipilimumab is a monoclonal antibody (MAb) that targets CTLA-4, a key negative regulator found on activated T cells. CTLA-4 binds to members of the B7 family of accessory molecules that are expressed by dendritic cells (DCs) and other antigen presenting cells (APCs). Binding of CTLA-4 to these accessory molecules effectively inhibits further T cell activation and expansion, thereby blocking the progress of an immune response involving such cells (Mellman et al., 2011Nature 480:480-489). By targeting CTLA-4, ipilimumab releases this inhibition, permitting activation and expansion of T cells, including specifically those that destroy cancer cells.

Other approaches that have been pursued to treat cancer by removing immune inhibition include targeting the Programmed Death-1 (PD-1) T cell co-receptor and its ligands B7-H1/PD-L1 and B7-DC/PD-L2, which are part of a pathway that maintains an immunosuppressive tumor microenvironment (Topalian et al., 2012 Curr. Opin. Immunol. 24:207-212). In particular, Phase I/II clinical trials using anti-PD-1 (Topalian et al., 2012 N. Engl. J. Med. 366:2443-2454) or anti-PD-L1 (Brahmer et al., 2012 N. Engl. J. Med. 366:2455-2465) antibodies have demonstrated tumor regression or stabilization in melanoma, non-small cell lung cancer, renal cell carcinoma and ovarian cancer.

Still other approaches have been designed to remove immune inhibition directed by natural killer (NK) cells. For example, human killer-cell Ig-like receptors (KIRs) are glycoproteins that are expressed on surfaces of NK cells and bind to major histocompatibility complex (MHC)/human leukocyte antigen (HLA) class I subtypes on potential target cells. This binding interaction inhibits the NK cells' cytotoxicity. Monoclonal antibodies that target KIRs have been shown in clinical trials to block such inhibition, relieving the suppression of NK activity. (Romagne et al, 2009, Blood 114:2667-2677).

Similarly, leukocyte Ig-like receptors (LIRs, also known as Ig-like transcripts, ILTs), are also expressed on surfaces of NK cells (as well as some T and B lymphocytes and certain macrophages, mast cells, and dendritic cells) and also bind to MHC/HLA class I subtypes, resulting in inhibition of activity of LIR-expressing effector cells. Some studies have reported success in stimulating effector cell cytotoxicity by blocking interactions between LIRs and MHC/GLA class I molecules (Godal et al., 2010, Biol. Blood Marrow Transplant 16:612-621).

Still further, a variety of approaches have been pursued that seek to undo tumor-associated immune suppression by targeting tumor-associated antigens. For example, blocking MAbs (e.g., anti-CD47) have been studied and found to be effective in stimulating macrophages to phagocytose tumor cells in leukemia/lymphoma and in solid tumor models, both in vitro and in vivo (Zhao et al., 2011, Proc. Natl. Acad. Sci. U.S.A. 108:18342-18247; Majeti et al., 2009, Cell 138:286-299; Chao et al., 2011, Cancer Res. 71:1374-1384; Chao et al., 2010, Sci. Transl. Med. 2:63ra94; Chao et al., 2010, Cell 142:699-713; Willingham et al., 2012, Proc. Natl. Acad. Sci. U.S.A. 109:6662-6667).

Other tumor antigen targets of particular interest include the ganglioside GD2, which is highly expressed on neuroectoderm-derived tumors and sarcomas, but has restricted expression on normal cells. GD2-targeting has been shown to promote NK cell activation through antibody-dependent cell-mediated cytotoxicity (ADCC) (Tarek et al., 2012, J. Clin. Invest. 122:3260-3270).

Human B7H3 (also known as CD276) is a member of the B7/CD28 immunoglobulin superfamily, which provides crucial costimulatory signals that regulate T cell function in the context of tumor surveillance as well as infectious and autoimmune diseases (Wilcox et al., 2012, Eur. J. Haematol. 88:465-475).

B7H3 is widely expressed on many solid tumor types, including in prostate cancer (Roth et al., 2007, Cancer Res. 67:7893-900; Zang et al., 2007, Proc. Natl. Acad. Sci. U.S.A. 104:19458-19463) renal cell carcinoma, urothelial cell carcinoma (Crispen et al. 2008, Clin. Cancer Res. 14:5150-5157; Boorjian et al., 2008, Clin. Cancer Res. 14:4800-4808), ovarian cancer (Zang et al., 2010, Mod. Pathol. 23:1104-1112), glioblastoma (Lemke et al., 2012, Clin. Cancer Res. 18:105-117), osteosarcoma (Wang et al., 2013, PLoS One 8:c70689), neuroblastoma (Gregorio et al., 2008, Histopathology 53:73-80), diffuse intrinsic pontine glioma (DIPG) (Zhou et al., 2013, J. Neurooncol. 111:257-264), mesothelioma (Calabro et al., 2011, J. Cell Physiol. 226:2595-600) and pancreatic cancer (Yamato et al., 2009, Br. J. Cancer 101:1709-1716).

B7H3 was initially identified as a type I transmembrane protein which, similar to all other B7 family members, has an extracellular region containing only one V-like and one C-like Ig domain (this form of B7H3 was termed 2Ig-B7H3) (Chapoval et al., 2001, Nat. Immunol. 2:269-274). Subsequently, a second form of human B7H3 (huB7H3) was identified (termed 4Ig-B7H3) that contains a duplication of the V-like and the C-like Ig domain in tandem (Steinberger et al., 2004, J. Immunol. 172:2352-2359; Sun et al., 2002, J. Immunol. 168:6294-6297).

B7H3 is considered to be inhibitory for both NK cells and T-cells. The idea of an inhibitory role of B7H3 is supported by reports indicating that both the 2Ig and 4Ig forms of human B7H3 can inhibit T cell proliferation and cytokine production (Steinberger et al., 2004, J. Immunol. 172:2352-2359; Sun et al. 2002 J. Immunol. 168:6294-6297). Studies in B7H3-deficient mice suggested that B7H3 preferentially down-regulates TH1– (as opposed to TH2–) mediated immune responses (Suh et al., 2003, Nat. Immunol. 4:899-906). And other investigations showed that the 4Ig-B7H3 form can inhibit NK-mediated lysis of neuroblastoma cells by interacting with a putative inhibitory receptor on the surface of NK cells (Castriconi et al., 2004, Proc. Natl. Acad. Sci. U.S.A. 101:12640-12645). In more recent studies involving patients with prostate cancer, the level of B7H3 expression on tumor tissue at the time of surgery was strongly correlated with the extent as to which the tumor had metastasized, with an increased risk of clinical cancer recurrence and with cancer-specific death (Roth et al., 2007, Cancer Res. 67:7893-7900; Zang et al., 2007, Proc. Natl. Acad. Sci. U.S.A. 104:19458-19463). Similarly, a high level of B7H3 expression on tumor tissue correlated with poor patient survival in clear cell renal cell carcinoma, urothelial cell carcinoma (Crispen et al., 2008, Clin. Cancer Res. 14:5150-5157; Boorjian et al., 2008, Clin. Cancer Res. 14:4800-4808), ovarian cancer (Zang et al., 2010, Mod. Pathol. 23:1104-1112), glioblastoma (Lemke et al., 2012, Clin. Cancer Res. 18:105-117) osteosarcoma (Wang et al., 2013, PLoS One 8:e70689), pancreatic cancer (Yamato et al., 2009, Br. J. Cancer 101:1709-1716) and neuroblastoma (Gregorio et al., 2008, Histopathology 53:73-80).

Based on crystal structure data for murine B7H3 (muB7H3), it was proposed that B7H3 inhibits T cell proliferation, at least in part, through the FG loop of its IgV domain (Vigdorovich et al., 2013, Structure 21:707-717).

On the other hand, B7H3 might also have T-cell stimulatory properties, depending on the receptors with which it interacts (Hofmeyer et al., 2008, Proc. Natl. Acad. Sci. U.S.A. 105:10277-10278). For example, a few earlier reports indicated that human 2Ig-B7H3 promotes T cell activation and IFN-γ production by binding to a putative receptor on activated T cells (Chapoval et al., 2001, Nat. Immunol. 2:269-274). Moreover, studies using certain murine tumor models provided data suggesting that the immune system's antitumor response is enhanced by B7H3 expression (Sun et al., 2003, Gene Ther. 10:1728-1734). And studies in humans suggested that the presence of B7H3 is correlated with increased survival in gastric (Wu et al., 2006, World J. Gastroenterol. 12:457-459) and pancreatic cancer (Loos et al., 2009, BMC Cancer 9:463).

A murine antibody, known as m8H9, that binds to B7H3 has been shown to target brain tumors, childhood sarcomas, and neuroblastomas, and to a lesser extent adenocarcinomas (Modak et al., 2001, Cancer Res. 61:4048-4054; Xu et al., 2009, Cancer Res. 69:6275-6281). Among primary brain tumors, 15 of 17 tested glioblastomas, 3 of 4 tested mixed gliomas, 4 of 11 tested oligodendrogliomas, 6 of 8 tested astrocytomas, 2 of 2 tested meningiomas, 3 of 3 tested schwannomas, 2 of 2 tested medulloblastomas, 1 of 1 tested neurofibroma, 1 of 2 tested neuronoglial tumors, 2 of 3 tested ependymomas, and 1 of 1 tested pineoblastoma showed binding by 8H9. Among sarcomas, 21 of 21 tested Ewing's/primitive neuroectodermal tumors, 28 of 29 tested rhabdomyosarcomas, 28 of 29 tested osteosarcomas, 35 of 37 tested desmoplastic small round cell tumors, 2 of 3 tested synovial sarcomas, 4 of 4 tested leiomyosarcomas, 1 of 1 malignant fibrous histiocytoma, and 2 of 2 tested undifferentiated sarcomas tested positive for 8H9 binding. Eighty-seven of 90 tested neuroblastomas, 12 of 16 tested melanomas, 3 of 4 tested hepatoblastomas, 7 of 8 tested Wilms' tumors, 3 of 3 tested rhabdoid tumors, and 12 of 27 tested adenocarcinomas also tested positive. In contrast, m8H9 did not bind to normal human tissues including bone marrow, colon, stomach, heart, lung, muscle, thyroid, testes, pancreas, and human brain (frontal lobe, cerebellum, pons, and spinal cord) (Modak et al., 2001 Cancer Res 61:4048-4054).

8H9 Antibody Agents

As noted above, 8H9 antibodies specifically bind to B7H3. Unlike other anti-B7H3 antibodies tested, only 8H9 can be used to bind the FG-loop of B7H3, and to block the immune-inhibitory function of B7H3.

Immuno-histochemical studies have demonstrated that m8H9 is broadly reactive with human solid tumors, including embryonal tumors and carcinomas (Modak et al., 2001, Cancer Res. 61:4048-4054). m8H9 has shown favorable tumor uptake for both sarcoma and brain tumors in xenograft models (Modak et al., 2005, Cancer Biother. Radiopharm. 20:534-546; Luther et al., 2008, Neurosurgery 63:1166-1174; discussion 1174), and when the antibody is conjugated to cobra-venom factor, it induces efficient complement mediated tumor lysis (Juhl et al., 1997, Immunobiology 197:444-459). Moreover, the single chain Fv (scFv) form of m8H9 was shown to be capable of targeting a potent immunotoxin to sarcomas and gliomas in a pre-clinical model system (Onda et al., 2004, Cancer Res. 64:1419-1424; Luther et al., 2010, Mol. Cancer Ther. 9:1039-1046).

As part of a chimeric antigen receptor (CAR), the scFv form of m8H9 is capable of directing NK cells to kill B7H3(+) positive tumor cells (Cheung et al., 2003, Hybrid Hybridomics 22:209-218). Moreover, certain early phase human clinical trials have shown that radioimmunotherapy with $^{131}$I-labeled 8H9 prolongs survival of high-risk patients with metastatic central nervous system (CNS) cancer (Kramer et al., 2007, American Association for Cancer Research LB-4 (Presentation); Kramer et al., 2008, Presentation at the ISPNO 2008).

Several Phase 1 clinical trials are currently ongoing for m8H9-based radioimmunotherapy of leptomeningeal metastases (NCT00089245) (Kramer et al., 2010 J Neurooncol 97:409-418) and diffuse intrinsic pontine glioma (DIPG) (NCT01502917) (Zhou et al., 2013, J. Neurooncol. 111:257-264). According to the inventors' knowledge, the only other anti-B7H3 antibody subject to a clinical trial is MGA271, a humanized IgG1 MAb (NCT01391143) (Loo et al., 2012, Clin. Cancer. Res. 18:3834-3845, 2012).

A radiolabeled m8H9 antibody is currently in clinical trials for treatment of desmoplastic small round cell tumors and other solid tumors involving the peritoneum (NCI Protocol ID 09-090 NCT01099644).

Mouse

Murine 8H9 (m8H9) is an IgG1 monoclonal antibody (MAb) that targets B7H3.

Humanized and Affinity Matured

While m8H9 is promising as therapeutic agent for the treatment of cancer in humans, it is of murine origin. The use of human antibodies is preferred in this context, among other things because it reduces the likelihood of immune reactions against the administered antibody.

The invention provides certain humanized antibody sequences, and also certain affinity-matured antibody sequences, found in antibodies that bind to B7H3, and particularly to its FG-loop. For example, particularly exemplified herein are antibody agents (e.g., full-length antibodies, fragments thereof, single chain antibodies, bi-specific antibodies, or other antibody agent formats as described herein or otherwise known in the art) that include polypeptides containing sequence elements as described herein.

In particular, the present invention provides an antibody agent that binds specifically to protein 2Ig-B7H3 and including an immunoglobulin light chain as set forth in a SEQ ID NO. selected from the group consisting of SEQ ID NO.: 1, 2, 3, 4, 5, 6, 7 and 8 (set forth below), or a relevant epitope-binding portion thereof, and/or including an immunoglobulin heavy chain as set forth in a SEQ ID NO. selected from the group consisting of SEQ ID NO.: 9, 10, 11, 12, 13, 14, 15 and 16 (set forth below), or a relevant epitope-binding portion thereof.

```
SEQ ID NO.: 1 (ch8H9 Light chain)
DIVMTQSPATLSVTPGDRVSLSCRASQSISDYLHWYQQKSHESPRLL

IKYASQSISGIPSRFSGSGSGSDFTLSINSVEPEDVGVYYCQNGHSF

PLTFGAGTKLELKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

SEQ ID NO.: 2 (hu8H9 L1 Light chain)
EIVMTQSPATLSVSPGERVTLSCRASQSISDYLHWYQQKPGQAPRLL

IKYASQSISGIPARFSGSGSGTEFTLTISSVQPEDVGVYYCQNGHSF

PLTFGQGTKLEIKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

SEQ ID NO.: 3 (hu8H9 L2 Light chain)
EIVMTQSPATLSVSPGERVTLSCRASQSISDYLHWYQQKSHESPRLL

IKYASQSISGIPARFSGSGSGTEFTLTINSVEPEDVGVYYCQNGHSF

PLTFGQGTKLEIKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

SEQ ID NO.: 4 (hu8H9 L3 Light chain)
EIVMTQSPATLSVSPGERVSLSCRASQSISDYLHWYQQKSHESPRLL

IKYASQSISGIPARFSGSGSGSEFTLTINSVEPEDVGVYYCQNGHSF

PLTFGQGTKLELKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

SEQ ID NO.: 5 (hu8H9 3.1 Light chain)
EIVMTQSPATLSVSPGERVTLSCRASQSISDYLYWYQQKSHESPRLL

IKYASQSISGIPARFSGSGSGSEFTLTINSVEPEDVGVYYCQNGHSF

PLTFGQGTKLELKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

SEQ ID NO.: 6 (hu8H9 4.1 Light chain)
EIVMTQSPATLSVSPGERVTLSCRASQSISDYLHWYQQKSHQAPRLL

IKYASQSISGIPARFSGSGSGSEFTLTISSLQPEDFGVYYCQNGHSF

PLTFGQGTKLELKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC
```

SEQ ID NO.: 7 (hu8H9 5.1 Light chain)
EIVMTQSPATLSVSPGERVTLSCRASQSISDYLYWYQQKSHQAPRLL

IKYASQSISGIPARFSGSGSGSEFTLTISSLQPEDFGVYYCQNGHSF

PLTFGQGTKLELKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

SEQ ID NO.: 8 (ch8H9 6.1 Light chain; ch8H9 + 6 affinity maturation mutations)
DIVMTQSPATLSVTPGDRVTLSCRASQSISDYLYWYQQKSHESPRLL

IKYASQSISGIPSRFSGSGSGSDFTLSINSVEPEDVGVYYCQNGHSF

PLTFGAGTKLELKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

SEQ ID NO.: 9 (ch8H9 Heavy chain)
QVQLQQSGAELVKPGASVKLSCKASGYTFTNYDINWVRQRPEQGLEW

IGWIFPGDGSTQYNEKFKGKATLTTDTSSSTAYMQLSRLTSEDSAVY

FCARQTTATWFAYWGQGTLVTVSSASTKGPSVFPLAPSSKSTSGGTA

ALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPEL

LGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPGK

SEQ ID NO.: 10 (hu8H9 H1 Heavy chain)
QVQLVQSGAEVKKPGASVKLSCKASGYTFTNYDINWVRQAPGQGLEW

IGWIFPGDGSTQYNEKFKGKATLTTDTSTSTAYMELSSLRSEDTAVY

FCARQTTATWFAYWGQGTLVTVSSASTKGPSVFPLAPSSKSTSGGTA

ALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPEL

LGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPGK

SEQ ID NO.: 11 (hu8H9 H2 Heavy chain)
QVQLVQSGAEVVKPGASVKLSCKASGYTFTNYDINWVRQAPGQGLEW

IGWIFPGDGSTQYNEKFKGKATLTTDTSTSTAYMELSRLTSEDTAVY

FCARQTTATWFAYWGQGTLVTVSSASTKGPSVFPLAPSSKSTSGGTA

ALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPEL

LGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPGK

SEQ ID NO.: 12 (hu8H9 H3 Heavy chain)
QVQLVQSGAEVVKPGASVKLSCKASGYTFTNYDINWVRQRPEQGLEW

IGWIFPGDGSTQYNEKFKGKATLTTDTSTSTAYMELSSLRSEDTAVY

FCARQTTATWFAYWGQGTLVTVSSASTKGPSVFPLAPSSKSTSGGTA

ALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPEL

LGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPGK

SEQ ID NO.: 13 (hu8H9 3.1 Heavy chain)
QVQLVQSGAEVVKPGASVKLSCKTSGYTFTNYDINWVRQRPGQGLEW

IGWIFPGDDSTQYNEKFKGKATLTTDTSTSTAYMELSSLRSEDTAVY

FCARQTTGTWFAYWGQGTLVTVSSASTKGPSVFPLAPSSKSTSGGTA

ALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPEL

LGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPGK

SEQ ID NO.: 14 (hu8H9 4.1 Heavy chain)
QVQLVQSGAEVVKPGASVKVSCKASGYTFTNYDINWVRQRPEQGLEW

IGWIFPGDGSTQYNEKFKGRVTMTTDTSTSTVYMELSSLRSEDTAVY

FCARQTTATWFAYWGQGTLVTVSSASTKGPSVFPLAPSSKSTSGGTA

ALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPEL

LGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPGK

SEQ ID NO.: 15 (hu8H9 5.1 Heavy chain)
QVQLVQSGAEVVKPGASVKVSCKTSGYTFTNYDINWVRQRPGQGLEW

IGWIFPGDDSTQYNEKFKGRVTMTTDTSTSTVYMELSSLRSEDTAVY

FCARQTTGTWFAYWGQGTLVTVSSASTKGPSVFPLAPSSKSTSGGTA

ALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPEL

LGGPSVFLFPPKPKDTLMISRTPEVTCVVVDVSHEDPEVKFNWYVDG

```
-continued
VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPGK

SEQ ID NO.: 16 (ch8H9 6.1 Heavy chain; ch8H9 +
6 affinity maturation mutations)
QVQLQQSGAELVKPGASVKLSCKTSGYTFTNYDINWVRQRPGQGLEW

IGWIFPGDDSTQYNEKFKGKATLTTDTSSSTAYMQLSRLTSEDSAVY

FCARQTTGTWFAYWGQGTLVTVSAASTKGPSVFPLAPSSKSTSGGTA

ALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPEL

LGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPGK
```

In some embodiments, a provided antibody agent is or comprises an antibody that is a member of an antibody class selected from the group consisting of IgG, IgM, IgA, IgD, IgE, or a fragment thereof.

Provided antibody agents, including antibodies and/or characteristic portions thereof, or nucleic acids encoding them, may be produced by any available means. Technologies for generating antibodies (e.g., monoclonal antibodies and/or polyclonal antibodies) are well known in the art. It will be appreciated that a wide range of animal species can be used for the production of antisera, including rabbit, mouse, rat, hamster, guinea pig or goat. The choice of animal may be decided upon the ease of manipulation, costs or the desired amount of sera, as would be known to one of skill in the art. It will be appreciated that antibody agents can also be produced transgenically through the generation of a mammal or plant that is transgenic for the immunoglobulin heavy and light chain sequences of interest. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957 (incorporated herein by reference in their entirety).

Provided antibody agents (including antibodies and/or characteristic portions) may be produced, for example, by utilizing a host cell system engineered to express an inventive antibody-encoding nucleic acid. Alternatively or additionally, provided antibody agents may be partially or fully prepared by chemical synthesis (e.g., using an automated peptide synthesizer).

Technologies of making and using polyclonal and monoclonal antibodies are described, e.g., in Harlow et al., Using Antibodies: A Laboratory Manual: Portable Protocol I. Cold Spring Harbor Laboratory (Dec. 1, 1998). Technologies for making modified antibody agents, such as, antibodies and antibody fragments (e.g., chimeric antibodies, reshaped antibodies, humanized antibodies, or fragments thereof, e.g., Fab', Fab, F(ab')₂ fragments); or biosynthetic antibodies (e.g., single chain antibodies, single domain antibodies (DABs), Fv, single chain Fv (scFv), and the like), are known in the art and can be found, e.g., in Zola, Monoclonal Antibodies: Preparation and Use of Monoclonal Antibodies and Engineered Antibody Derivatives, Springer Verlag (Dec. 15, 2000; 1st edition).

Exemplary sources for antibody agent preparations suitable for the invention include, but are not limited to, conditioned culture medium derived from culturing a recombinant cell line that expresses a protein of interest, or from a cell extract of, e.g., antibody-producing cells, bacteria, fungal cells, insect cells, transgenic plants or plant cells, transgenic animals or animal cells, or serum of animals, ascites fluid, hybridoma or myeloma supernatants. Suitable bacterial cells include, but are not limited to, *Escherichia coli* cells. Examples of suitable *E. coli* strains include: HB101, DH5α, GM2929, JM109, KW251, NM538, NM539, and any *E. coli* strain that fails to cleave foreign DNA. Suitable fungal host cells that can be used include, but are not limited to, *Saccharomyces cerevisiae, Pichia pastoris* and *Aspergillus* cells. Suitable insect cells include, but are not limited to, S2 Schneider cells, D. Me1-2 cells, SF9, SF21, High-5™, Mimic™-SF9, MG1 and KC1 cells. Suitable exemplary recombinant cell lines include, but are not limited to, BALB/c mouse myeloma line, human retinoblasts (PER.C6), monkey kidney cells, human embryonic kidney line (293), baby hamster kidney cells (BHK), Chinese hamster ovary cells (CHO), mouse sertoli cells, African green monkey kidney cells (VERO-76), human cervical carcinoma cells (HeLa), canine kidney cells, buffalo rat liver cells, human lung cells, human liver cells, mouse mammary tumor cells, TRI cells, MRC 5 cells, FS4 cells, and human hepatoma line (Hep G2).

Antibody agents of interest can be expressed using any appropriate vector. A variety of vectors (e.g., viral vectors) is known in the art; cells into which such vectors have been introduced (or progeny of such cells) can be cultured as known in the art (e.g., using continuous or fed-batch culture systems). In some embodiments, cells may be genetically engineered; technologies for genetically engineering cells to express engineered polypeptides (e.g., antibody agent polypeptides, as described herein) are well known in the art. See e.g. Ausabel et al., eds. (1990), Current Protocols in Molecular Biology (Wiley, New York).

In some embodiments, provided antibody agents may be purified, if desired, using filtration, centrifugation and/or a variety of chromatographic technologies such as HPLC or affinity chromatography. In some embodiments, fragments of provided antibody agents are obtained by methods that include digestion with enzymes, such as pepsin or papain, and/or by cleavage of disulfide bonds by chemical reduction.

In general, as described herein, provided antibody agents can be or include, e.g., a polyclonal antibody; a monoclonal antibody or antigen binding fragment thereof; a modified antibody such as a chimeric antibody, reshaped antibody, humanized antibody, or fragment thereof (e.g., Fab', Fab, F(ab')₂); or a biosynthetic antibody, e.g., a single chain antibody, single domain antibody (DAB), Fv, single chain Fv (scFv), or the like.

It will be appreciated that provided antibody agents may be engineered, produced, and/or purified in such a way as to improve characteristics and/or activity of the antibody agents. For example, improved characteristics of provided antibody agents include, but are not limited to, increased stability, improved binding affinity and/or avidity, increased binding specificity, increased production, decreased aggregation, decreased nonspecific binding, among others.

Specific Exemplary Embodiments—Combinations of Light and Heavy Chains

In some embodiments of the present invention, the antibody agent includes an immunoglobulin light chain as set forth in SEQ ID NO.: 1 and/or an immunoglobulin heavy chain as set forth in SEQ ID NO.: 9. In some embodiments of the present invention, an antibody agent is an antibody including an immunoglobulin light chain as set forth in SEQ ID NO.: 1 and/or an immunoglobulin heavy chain as set forth in SEQ ID NO.: 9.

In some embodiments of the present invention, the antibody agent includes an immunoglobulin light chain as set forth in SEQ ID NO.: 2 and/or an immunoglobulin heavy chain as set forth in SEQ ID NO.: 10. In some embodiments of the present invention, an antibody agent is an antibody including an immunoglobulin light chain as set forth in SEQ ID NO.: 2 and/or an immunoglobulin heavy chain as set forth in SEQ ID NO.: 10.

In some embodiments of the present invention, the antibody agent includes an immunoglobulin light chain as set forth in SEQ ID NO.: 3 and/or an immunoglobulin heavy chain as set forth in SEQ ID NO.: 11. In some embodiments of the present invention, an antibody agent is an antibody including an immunoglobulin light chain as set forth in SEQ ID NO.: 3 and/or an immunoglobulin heavy chain as set forth in SEQ ID NO.: 11.

In some embodiments of the present invention, the antibody agent includes an immunoglobulin light chain as set forth in SEQ ID NO.: 4 and/or an immunoglobulin heavy chain as set forth in SEQ ID NO.: 12. In some embodiments of the present invention, an antibody agent is an antibody including an immunoglobulin light chain as set forth in SEQ ID NO.: 4 and/or an immunoglobulin heavy chain as set forth in SEQ ID NO.: 12.

In some embodiments of the present invention, the antibody agent includes an immunoglobulin light chain as set forth in SEQ ID NO.: 2 and/or an immunoglobulin heavy chain as set forth in SEQ ID NO.: 11. In some embodiments of the present invention an antibody agent is an antibody including an immunoglobulin light chain as set forth in SEQ ID NO.: 2 and/or an immunoglobulin heavy chain as set forth in SEQ ID NO.: 11.

In some embodiments of the present invention, the antibody agent includes an immunoglobulin light chain as set forth in SEQ ID NO.: 3 and/or an immunoglobulin heavy chain as set forth in SEQ ID NO.: 10. In some embodiments of the present invention, an antibody agent is an antibody including an immunoglobulin light chain as set forth in SEQ ID NO.: 3 and/or an immunoglobulin heavy chain as set forth in SEQ ID NO.: 10.

In some embodiments of the present invention, the antibody agent includes an immunoglobulin light chain as set forth in SEQ ID NO.: 5 and/or an immunoglobulin heavy chain as set forth in SEQ ID NO.: 13. In some embodiments of the present invention, an antibody agent is an antibody including an immunoglobulin light chain as set forth in SEQ ID NO.: 5 and/or an immunoglobulin heavy chain as set forth in SEQ ID NO.: 13.

In some embodiments of the present invention, the antibody agent includes an immunoglobulin light chain as set forth in SEQ ID NO.: 6 and/or an immunoglobulin heavy chain as set forth in SEQ ID NO.: 14. In some embodiments of the present invention, an antibody agent is an antibody including an immunoglobulin light chain as set forth in SEQ ID NO.: 6 and/or an immunoglobulin heavy chain as set forth in SEQ ID NO.: 14.

In some embodiments of the present invention, the antibody agent includes an immunoglobulin light chain as set forth in SEQ ID NO.: 7 and/or an immunoglobulin heavy chain as set forth in SEQ ID NO.: 15. In some embodiments of the present invention, an antibody agent is an antibody including an immunoglobulin light chain as set forth in SEQ ID NO.: 7 and/or an immunoglobulin heavy chain as set forth in SEQ ID NO.: 15.

In some embodiments of the present invention, the antibody agent includes an immunoglobulin light chain as set forth in SEQ ID NO.: 8 and/or an immunoglobulin heavy chain as set forth in SEQ ID NO.: 16. In some embodiments of the present invention, an antibody agent is an antibody including an immunoglobulin light chain as set forth in SEQ ID NO.: 8 and/or an immunoglobulin heavy chain as set forth in SEQ ID NO.: 16.

The present invention contemplates, among other things, below listed antibodies including immunoglobulin light chains as set forth in the indicated SEQ ID NOs., or epitope-binding portions thereof, and immunoglobulin heavy chains as set forth in the indicated SEQ ID NOs., or epitope-binding portions thereof.

TABLE 1

| Antibody No. | Light Chain | Heavy Chain |
| --- | --- | --- |
| 1 | SEQ ID NO.: 1 | SEQ ID NO.: 9 |
| 2 | SEQ ID NO.: 1 | SEQ ID NO.: 10 |
| 3 | SEQ ID NO.: 1 | SEQ ID NO.: 11 |
| 4 | SEQ ID NO.: 1 | SEQ ID NO.: 12 |
| 5 | SEQ ID NO.: 1 | SEQ ID NO.: 13 |
| 6 | SEQ ID NO.: 1 | SEQ ID NO.: 14 |
| 7 | SEQ ID NO.: 1 | SEQ ID NO.: 15 |
| 8 | SEQ ID NO.: 1 | SEQ ID NO.: 16 |
| 9 | SEQ ID NO.: 2 | SEQ ID NO.: 9 |
| 10 | SEQ ID NO.: 2 | SEQ ID NO.: 10 |
| 11 | SEQ ID NO.: 2 | SEQ ID NO.: 11 |
| 12 | SEQ ID NO.: 2 | SEQ ID NO.: 12 |
| 13 | SEQ ID NO.: 2 | SEQ ID NO.: 13 |
| 14 | SEQ ID NO.: 2 | SEQ ID NO.: 14 |
| 15 | SEQ ID NO.: 2 | SEQ ID NO.: 15 |
| 16 | SEQ ID NO.: 2 | SEQ ID NO.: 16 |
| 17 | SEQ ID NO.: 3 | SEQ ID NO.: 9 |
| 18 | SEQ ID NO.: 3 | SEQ ID NO.: 10 |
| 19 | SEQ ID NO.: 3 | SEQ ID NO.: 11 |
| 20 | SEQ ID NO.: 3 | SEQ ID NO.: 12 |
| 21 | SEQ ID NO.: 3 | SEQ ID NO.: 13 |
| 22 | SEQ ID NO.: 3 | SEQ ID NO.: 14 |
| 23 | SEQ ID NO.: 3 | SEQ ID NO.: 15 |
| 24 | SEQ ID NO.: 3 | SEQ ID NO.: 16 |
| 25 | SEQ ID NO.: 4 | SEQ ID NO.: 9 |
| 26 | SEQ ID NO.: 4 | SEQ ID NO.: 10 |
| 27 | SEQ ID NO.: 4 | SEQ ID NO.: 11 |
| 28 | SEQ ID NO.: 4 | SEQ ID NO.: 12 |
| 29 | SEQ ID NO.: 4 | SEQ ID NO.: 13 |
| 30 | SEQ ID NO.: 4 | SEQ ID NO.: 14 |
| 31 | SEQ ID NO.: 4 | SEQ ID NO.: 15 |
| 32 | SEQ ID NO.: 4 | SEQ ID NO.: 16 |
| 33 | SEQ ID NO.: 5 | SEQ ID NO.: 9 |
| 34 | SEQ ID NO.: 5 | SEQ ID NO.: 10 |
| 35 | SEQ ID NO.: 5 | SEQ ID NO.: 11 |
| 36 | SEQ ID NO.: 5 | SEQ ID NO.: 12 |
| 37 | SEQ ID NO.: 5 | SEQ ID NO.: 13 |
| 38 | SEQ ID NO.: 5 | SEQ ID NO.: 14 |
| 39 | SEQ ID NO.: 5 | SEQ ID NO.: 15 |
| 40 | SEQ ID NO.: 5 | SEQ ID NO.: 16 |
| 41 | SEQ ID NO.: 6 | SEQ ID NO.: 9 |
| 42 | SEQ ID NO.: 6 | SEQ ID NO.: 10 |
| 43 | SEQ ID NO.: 6 | SEQ ID NO.: 11 |
| 44 | SEQ ID NO.: 6 | SEQ ID NO.: 12 |
| 45 | SEQ ID NO.: 6 | SEQ ID NO.: 13 |
| 46 | SEQ ID NO.: 6 | SEQ ID NO.: 14 |
| 47 | SEQ ID NO.: 6 | SEQ ID NO.: 15 |
| 48 | SEQ ID NO.: 6 | SEQ ID NO.: 16 |
| 49 | SEQ ID NO.: 7 | SEQ ID NO.: 9 |

TABLE 1-continued

| Antibody No. | Light Chain | Heavy Chain |
| --- | --- | --- |
| 50 | SEQ ID NO.: 7 | SEQ ID NO.: 10 |
| 51 | SEQ ID NO.: 7 | SEQ ID NO.: 11 |
| 52 | SEQ ID NO.: 7 | SEQ ID NO.: 12 |
| 53 | SEQ ID NO.: 7 | SEQ ID NO.: 13 |
| 54 | SEQ ID NO.: 7 | SEQ ID NO.: 14 |
| 55 | SEQ ID NO.: 7 | SEQ ID NO.: 15 |
| 56 | SEQ ID NO.: 7 | SEQ ID NO.: 16 |
| 57 | SEQ ID NO.: 8 | SEQ ID NO.: 9 |
| 58 | SEQ ID NO.: 8 | SEQ ID NO.: 10 |
| 59 | SEQ ID NO.: 8 | SEQ ID NO.: 11 |
| 60 | SEQ ID NO.: 8 | SEQ ID NO.: 12 |
| 61 | SEQ ID NO.: 8 | SEQ ID NO.: 13 |
| 62 | SEQ ID NO.: 8 | SEQ ID NO.: 14 |
| 63 | SEQ ID NO.: 8 | SEQ ID NO.: 15 |
| 64 | SEQ ID NO.: 8 | SEQ ID NO.: 16 |

Specific Exemplary Embodiments—Specific Amino Acid Residues

In some embodiments of the present invention, an antibody agent includes an immunoglobulin light chain including a threonine residue at position 20 and a tyrosine residue at position 34, and/or an immunoglobulin heavy chain including a threonine residue at position 24, a glycine residue at position 42, an aspartic acid residue at position 56, and a glycine residue at position 102.

In some embodiments of the present invention, an antibody agent carries a homologous amino acid substitution with respect to the threonine at light chain position 20, the tyrosine at light chain position 34, the threonine at heavy chain position 24, the glycine at heavy chain position 42, the aspartic acid at heavy chain position 56, and the glycine at heavy chain position 102.

In some embodiments of the present invention, the antibody agent includes an immunoglobulin light chain as set forth in a SEQ ID NO. selected from the group consisting of SEQ ID NO.: 1, 2, 3, 4, 5, 6, 7 and 8, including a threonine residue at position 20 and a tyrosine residue at position 34, and/or includes an immunoglobulin heavy chain as set forth in a SEQ ID NO. selected from the group consisting of SEQ ID NO.: 9, 10, 11, 12, 13, 14, 15 and 16, including a threonine residue at position 24, a glycine residue at position 42, an aspartic acid residue at position 56, and a glycine residue at position 102.

In some embodiments of the present invention, the antibody agent is murine 8H9 antibody, wherein an immunoglobulin light chain includes a threonine residue at position 20 and a tyrosine residue at position 34, and wherein an immunoglobulin heavy chains includes a threonine residue at position 24, a glycine residue at position 42, an aspartic acid residue at position 56, and a glycine residue at position 102.

Among other things, the present disclosure demonstrates that presence of these amino acid residues in an 8H9 antibody agent increases the antibody agent's binding affinity to B7H3 relative to that observed with m8H9. That is, introduction of these residues into m8H9 improves its binding affinity to B7H3, and particularly to the FG loop of its V-domain.

Those skilled in the art are aware of a variety of technologies, well-established in the art, for accomplishing such introduction, or for otherwise preparing, providing, or manufacturing polypeptides containing such sequences. Exemplary technologies useful in this regard are provided, for instance, in Green & Sambrook, Molecular Cloning: A Laboratory Manual, Cold Spring Harbor Laboratory Press 2012.

Specific Exemplary Embodiments—Specific Affinities

The present disclosure provides the first demonstration that antibody agents, including 8H9 antibody agents, that target the FG-loop of B7H3, can be used to block the immune-inhibitory function of B7H3.

The present invention provides antibody agents specifically binding to the epitope set forth in SEQ ID NO.: 32 (set forth below) located in the FG loop in the V-domain of protein 2Ig-B7H3 and in the V1 and V2 domains of protein 4Ig-B7H3, and antibody agents specifically binding to the same epitope with a dissociation constant ($K_D$) of less than 2 nM. As disclosed in the Examples herein, the described humanized and affinity matured 8H9 antibody and binding fragments thereof have these characteristics. In some embodiments, these antibody agents are not m8H9.

The IRDF epitope is conserved among species and found, for example, in humans, dogs, chimpanzees, orangutans, gibbons, macaques, marmosets, pigs, horses, pandas, and elephants. The present invention provides antibody agents specifically binding to the epitope set forth in SEQ ID NO.: 32 that is present in human and non-human animals, including dogs, chimpanzees, orangutans, gibbons, macaques, marmosets, pigs, horses, pandas, and elephants.

SEQ ID NO.: 32 is IRDF

In certain embodiments of the present invention, the antibody agents bind to the FG loop in the V-domain of protein 2Ig-B7H3 and in the V1 and V2 domains of protein 4Ig-B7H3 with a $K_D$ (nM) of less than 100 nM, less than 80 nM, less than 50 nM, less than 30 nM, less than 10 nM, less than 5 nM and less than 2 nM.

In some embodiments of the present invention, the antibody agents suppress the inhibitory effect of B7H3 on T cell proliferation and function.

In some embodiments of the present invention, the antibody agents suppress the inhibitory effect of B7H3 on T cell proliferation and function and/or enhance T-cell mediated cytotoxicity.

In some embodiments of the present invention, an antibody agent as described herein suppresses an inhibitory effect of B7H3 on NK cell activity and/or function.

In some embodiments of the present invention, an antibody agent as described herein suppresses an inhibitory effect of B7H3 on NK cell activity and/or function and/or enhance NK cell activity and/or function.

Assays to determine such effects are widely known in the art. Some exemplary, but not limiting, assays are provided in the Examples herein.

In some embodiments, antibody agents comprise and/or are antibodies, antibody fragments and/or scFvs.

Specific Exemplary Embodiments—Specific CDRs

As is generally known in the art, human and murine antibodies are usually made of two light chains and two heavy chains, each comprising variable regions and constant regions. The light chain variable region usually comprises 3 CDRs (complementary determining regions), identified herein as CDRL1, CDRL2 and CDRL3, flanked by framework regions. The heavy chain variable region usually comprises 3 CDRs, identified herein as CDRH1, CDRH2 and CDRH3, flanked by framework regions (see, e.g., William E. Paul, Fundamental Immunology (7th ed.), Lippincott Williams & Wilkins 2013).

In some embodiments of the invention, an antibody agent that binds specifically to protein 2Ig-B7H3 or 4Ig-B7H3 includes an immunoglobulin light chain including a CDRL1 set forth in a SEQ ID NO. selected from the group consisting of SEQ ID NO.: 33, 34, 39, 40, 45, 46, 51 and 52 (set forth below), or a relevant epitope-binding portion thereof. In some embodiments, the antibody agent is an antibody, scFv, and/or a relevant epitope-binding portion thereof.

In some embodiments of the invention, an antibody agent that binds specifically to protein 2Ig-B7H3 or 4Ig-B7H3 includes an immunoglobulin light chain including a CDRL2 set forth in a SEQ ID NO. selected from the group consisting of SEQ ID NO.: 35, 36, 41, 42, 47, 48, 53 and 54 (set forth below), or a relevant epitope-binding portion thereof. In some embodiments, the antibody agent is an antibody, scFv, and/or a relevant epitope-binding portion thereof.

In some embodiments of the invention, an antibody agent that binds specifically to protein 2Ig-B7H3 or 4Ig-B7H3 includes an immunoglobulin light chain including a CDRL3 set forth in a SEQ ID NO. selected from the group consisting of SEQ ID NO.: 37, 38, 43, 44, 49, 50, 55 and 56 (set forth below), or a relevant epitope-binding portion thereof. In some embodiments, the antibody agent is an antibody, scFv, and/or a relevant epitope-binding portion thereof.

In some embodiments of the invention, an antibody agent that binds specifically to protein 2Ig-B7H3 or 4Ig-B7H3 includes an immunoglobulin heavy chain including a CDRH1 set forth in a SEQ ID NO. selected from the group consisting of SEQ ID NO.: 57, 58, 63, 64, 69, 70, 75 and 76 (set forth below), or a relevant epitope-binding portion thereof. In some embodiments, the antibody agent is an antibody, scFv, and/or a relevant epitope-binding portion thereof.

In some embodiments of the invention, an antibody agent that binds specifically to protein 2Ig-B7H3 or 4Ig-B7H3 includes an immunoglobulin heavy chain including a CDRH2 set forth in a SEQ ID NO. selected from the group consisting of SEQ ID NO.: 59, 60, 65, 66, 71, 72, 77 and 78 (set forth below), or a relevant epitope-binding portion thereof. In some embodiments, the antibody agent is an antibody, scFv, and/or a relevant epitope-binding portion thereof.

In some embodiments of the invention, an antibody agent that binds specifically to protein 2Ig-B7H3 or 4Ig-B7H3 includes an immunoglobulin heavy chain including a CDRH3 set forth in a SEQ ID NO. selected from the group consisting of SEQ ID NO.: 61, 62, 67, 68, 73, 74, 79 and 80 (set forth below), or a relevant epitope-binding portion thereof. In some embodiments, the antibody agent is an antibody, scFv, and/or a relevant epitope-binding portion thereof.

The present invention contemplates antibody agents including CDRs set forth below in any possible combination. By example, which is not meant to be limiting, the invention includes antibody agents including a CDRL1, CDRL2, CDRL3, CDRH1, CDRH2 and CDRH3 that are SEQ ID NO.: 34, SEQ ID NO.: 36, SEQ ID NO.: 38, SEQ ID NO.: 58, SEQ ID NO.: 60 and SEQ ID NO.: 62, respectively.

The manufacture of antibodies having desired CDRs and/or framework regions is generally known in the art and described in, for example, Strohl & Strohl, Therapeutic Antibody Engineering, Woodhead Publishing Limited 2012.

|  | CDRL1 | CDRL2 | CDRL3 |
|---|---|---|---|
|  | Kabat | | |
| m8h9, | RASQSISDYLH | YASQSIS | QNGHSFPLT |
| ch8H9 | SEQ ID NO.: 33 | SEQ ID NO.: 35 | SEQ ID NO.: 37 |
| Hu8H9 | RASQSISDYLY | YASQSIS | QNGHSFPLT |
| 3.1, 5.1 | SEQ ID NO.: 34 | SEQ ID NO.: 36 | SEQ ID NO.: 38 |
|  | Chothia | | |
| m8h9, | SQSISDY | YAS | GHSFPL |
| ch8H9 | SEQ ID NO.: 39 | SEQ ID NO.: 41 | SEQ ID NO.: 43 |
| Hu8H9 | SQSISDY | YAS | GHSFPL |
| 3.1, 5.1 | SEQ ID NO.: 40 | SEQ ID NO.: 42 | SEQ ID NO.: 44 |
|  | Honegger | | |
| m8h9, | ASQSISDY | YASQSISGIPSR | GHSFPL |
| ch8H9 | SEQ ID NO.: 45 | SEQ ID NO.: 47 | SEQ ID NO.: 49 |
| Hu8H9 | ASQSISDY | YASQSISGIPAR | GHSFPL |
| 3.1, 5.1 | SEQ ID NO.: 46 | SEQ ID NO.: 48 | SEQ ID NO.: 50 |
|  | IMGT | | |
| m8h9, | QSISDY | YAS | QNGHSFPLT |
| ch8H9 | SEQ ID NO.: 51 | SEQ ID NO.: 53 | SEQ ID NO.: 55 |
| Hu8H9 | QSISDY | YAS | QNGHSFPLT |
| 3.1, 5.1 | SEQ ID NO.: 52 | SEQ ID NO.: 54 | SEQ ID NO.: 56 |

|  | CDRH1 | CDRH2 | CDRH3 |
|---|---|---|---|
|  | Kabat | | |
| m8h9, | NYDIN | WIFPGDGSTQYNEK FKG | QTTATWFAY |
| ch8H9 | SEQ ID NO.: 57 | SEQ ID NO.: 59 | SEQ ID NO.: 61 |
| Hu8H9 | NYDIN | WIFPGDDSTQYNEK FKG | QTTGTWFAY |
| 3.1, 5.1 | SEQ ID NO.: 58 | SEQ ID NO.: 60 | SEQ ID NO.: 62 |
|  | Chothia | | |
| m8h9, | GYTFTNY | PGDG | TTATWFA |
| ch8H9 | SEQ ID NO.: 63 | SEQ ID NO.: 65 | SEQ ID NO.: 67 |
| Hu8H9 | GYTFTNY | PGDD | TTGTWFA |
| 3.1, 5.1 | SEQ ID NO.: 64 | SEQ ID NO.: 66 | SEQ ID NO.: 68 |
|  | Honegger | | |
| m8h9, | ASGYTFTNYD | IFPGDGSTQYNEKF KGKA | QTTATWFA |
| ch8H9 | SEQ ID NO.: 69 | SEQ ID NO.: 71 | SEQ ID NO.: 73 |
| Hu8H9 | TSGYTFTNYD | IFPGDDSTQYNEKF KGRV | QTTGTWFA |
| 3.1, 5.1 | SEQ ID NO.: 70 | SEQ ID NO.: 72 | SEQ ID NO.: 74 |
|  | IMGT | | |
| m8h9, | GYTFTNYD | IFPGDGST | ARQTTATWFAY |
| ch8H9 | SEQ ID NO.: 75 | SEQ ID NO.: 77 | SEQ ID NO.: 79 |
| Hu8H9 | GYTFTNYD | IFPGDDST | ARQTTGTWFAY |
| 3.1, 5.1 | SEQ ID NO.: 76 | SEQ ID NO.: 78 | SEQ ID NO.: 80 |

Antibody Agent Formats

Those skilled in the art, reading the present disclosure, will appreciate that provided antibody sequences, or epitope-binding portions thereof, may usefully be incorporated into any of a variety of immunoglobulin-based or other polypeptide formats; embodiments of the invention therefore include a variety of polypeptides and polypeptide formats including sequence elements, or epitope-binding portions thereof, as described herein. Included within such provided polypeptides and polypeptide formats are those that bind specifically to B7H3, and particularly to its FG-loop. In some particular embodiments, provided polypeptides and/or polypeptide formats compete with m8H9 for binding to B7H3, e.g., to its FG-loop.

Single-Chain Fv (scFv)

Single-chain Fvs (scFvs) are widely known and used in the art. A single-chain Fv is a fusion protein of the variable regions of the heavy (VH) and light chains (VL) of immunoglobulins, often connected by a short linker peptide (see, e.g., see, e.g., Benny K. C. Lo (ed.), Antibody Engineering—Methods and Protocols, Humana Press 2004, and references cited therein).

The present invention also provides single-chain Fvs (scFvs) binding specifically to protein B7H3 and including a polypeptide as set forth in a SEQ ID NO. selected from the group consisting of SEQ ID NO.: 17, 18, 19, 20, 21, 22, 23, 24, 25, 26 and 27 (set forth below). Polypeptides as set forth in SEQ ID NOs.: 17, 18, 19, 20, 21, 22, 23, 24, 25, 26 and 27 are further described in the Examples herein.

In some embodiments of the present invention, an scFv polypeptide is conjugated to a therapeutic agent or detection agent, or comprises a threonine at position 24, a glycine at position 42, an aspartic acid residue at position 56, a glycine residue at position 102, a threonine residue at position 153 and a tyrosine residue at position 167. The 6 specific amino acid residues at these 6 specific positions are further described in the Examples.

In some embodiments of the present invention, these amino acid residues are substituted with a homologous amino acid (i.e., those with similar characteristics).

As is known to the skilled artisan, generation of scFvs and their modification in accordance with the present invention is routine in the art (see, e.g., Benny K. C. Lo (ed.), Antibody Engineering—Methods and Protocols, Humana Press 2004, and references cited therein).

In some embodiments of the present invention, an scFv polypeptide is fused to a second polypeptide.

In some embodiments of the present invention, an scFv polypeptide as set forth in a SEQ ID NO. selected from the group consisting of SEQ ID NO.: 17, 18, 19, 20, 21, 22, 23, 24, 25, 26 and 27 is fused to a second polypeptide as set forth in SEQ ID NO.: 28 or SEQ ID NO.: 29 (set forth below) to create a bispecific tandem scFv. SEQ ID NO.: 28 includes a peptide linker sequence and a peptide sequence of a scFv binding huOkt3 (anti-CD3), which is part of the T cell receptor complex. Similarly, SEQ ID NO.: 29 includes a peptide linker sequence and a peptide sequence of an anti-DOTA C825 scFv antibody fragment.

The utility of bispecific tandem scFvs is widely known and accepted in the art and similar to the utility of bispecific antibodies, which is described elsewhere herein. As is known to the skilled artisan, generation of scFvs and their modification, including but not limited to the manufacture of bispecific tandem scFvs, in accordance with the present invention is routine in the art (see, e.g., Benny K. C. Lo (ed.), Antibody Engineering—Methods and Protocols, Humana Press 2004, and references cited therein).

In some embodiments, an scFv including the polypeptide as set forth in a SEQ ID NO. selected from the group consisting of SEQ ID NO.: 17, 18, 19, 20, 21, 22, 23, 24, 25, 26 and 27 is fused with its C-terminus to the N-terminus of a polypeptide as set forth in SEQ ID NO.: 28 or SEQ ID NO.: 29. In some embodiments, an scFv including the polypeptide a set forth in a SEQ ID NO. selected from the group consisting of SEQ ID NO.: 17, 18, 19, 20, 21, 22, 23, 24, 25, 26 and 27 is fused with its N-terminus to the C-terminus of a polypeptide as set forth in SEQ ID NO.: 28 or SEQ ID NO.: 29.

SEQ ID NO.: 17 (hu8H9 H3L3 scFv) is
QVQLVQSGAEVVKPGASVKLSCKASGYTFTNYDINWVRQRPEQGLEW

IGWIFPGDGSTQYNEKFKGKATLTTDTSTSTAYMELSSLRSEDTAVY

FCARQTTATWFAYWGQGTLVTVSSGGGGSGGGGSGGGGSEIVMTQSP

ATLSVSPGERVSLSCRASQSISDYLHWYQQKSHESPRLLIKYASQSI

SGIPARFSGSGSGSEFTLTINSVEPEDVGVYYCQNGHSFPLTFGQGT

KLELKR

SEQ ID NO.: 18 (hu8H9 clone S3.3 scFv) is
QVQLVQSGAEVVKPGASVKLSCKTSGYTFTNYDINWVRQRPGQGLEW

IGWIFPGDGSTQYNEKFKGKATLTTDTSTSTAYMELSSLRSEDTAVY

FCARQTTATWFAYWGQGTLVTVSSGGGGSGGGGSGGGGSEIVMTQSP

ATLSVSPGERVTLSCRASQSISDYLYWYQQKSHESPRLLIKYASQSI

SGIPARFSGSGSGSEFTLTINSVEPEDVGVYYCQNGHSFPLTFGQGT

KLELKR

SEQ ID NO.: 19 (hu8H9 clone S7.2 scFv) is
QVQLVQSGAEVVKPGASCKLSCKTSGYTFTNYDINWVRQRPGQGLEW

IGWIFPGDGSTQYNEKFKGKATLTTDTSTSTAYMELSSLRSEDTAVY

FCARQTTATWFAYWGQGTLVTVSSGGGGSGGGGSGGVGSEIVMTQSP

ATLSVSPGERVTLSCRASQSIGDYLYWYQQKSHESPRLLIKYASQSI

SGIPARFSGSGSGSEFTLTINSVEPEDVGVYYCQNGHSFPLTFGQGT

KLELKR

SEQ ID NO.: 20 (hu8H9 clone S7.17 scFv) is
QVQLVQSGAEVVKPGASVKLSCKTSGYTFTNYDINWVRQRPGQGLEW

VGWIFPGDGSTQYNEKFKGKATLTTDTSTSTAYMELSSLRSEDTAVY

FCARQTTSTWFAYWGQGTLVTVSSGGGGSGGGGSGGGGSEIVMTQSP

ATLSVSPGERVTLSCRASQPISDYLYWYQQKSHESPRLLIKYASQSI

SGIPARFSGSGSGSEFTLTINSVEPEDVGVYYCQNGYSFPLTFGQGT

KLELKR

SEQ ID NO.: 21 (hu8H9 clone S7.22 scFv) is
QVQLVQSGAEVVKPGASVKLSCKTSGYTFTNYDINWVRQRPGQGLEW

IGWIFPGDDSTQYNEKFKGKATLTTDTSTSTAYMELSSLRPEDTAVY

FCARQTTGTWFAYWGQGTLVTVSSGGGGSGGGGSGGGGSEIVMTQSP

ATLSVSPGERVTLSCRASQSISDYLYWYQQKSHESPRLLIKYASQSI

PGIPARFSGSGSGSEFTLTINSVEPEDVGVYYCQNGHSFPLTFGQGT

KLELKR

SEQ ID NO.: 22 (hu8H9 clone S7.28 scFv) is
QVQLVQSGAEVVKPGASVKLSCKTSGYTFTNYDINWVRQRPGQGLEW

IGWIFPGDGSTQYNEKFKGKATLTTDTSTSTAYMELSSLGSEDTAVY

FCTRQTTATWFAYWGQGTLVTVSSGGGGSGGGGSGGGGSEIVMTQSP

ATLSVSPGERVTLSCRASQSIGDYLYWYQQKSHESPRLLIKYASQSI

SGIPARFSGSGSGSEFTLTINSVEPEDVGVYYCQNGHSFPLTFGQGT

KLELKR

SEQ ID NO.: 23 (hu8H9 clone S7.29 scFv) is
QVQLVQSGAEVVKPGASVKLSCKTSGYTFTNYDINWVRQRPGQGLEW
IGWIFPGDGSTQYNEKFKGKATLTTDTSTSTAYLELSSLGSEDTAVY
FCARQTTGTWFAYWGQGTLVTVSSGGGGSGGGGSGGGGSEIVMTQSP
ATLSVSPGERVTLSCRASQSISDYLYWYQQKSHESPRLLIKYASQSI
SGIPARFSGSGSGSEFTLTINSVEPEDVGVYYCQNGHSFPLTFGQGT
KLELKR SEQ ID NO.: 24 (hu8H9 3.1 scFv) is
QVQLVQSGAEVVKPGASVKLSCKTSGYTFTNYDINWVRQRPGQGLEW
IGWIFPGDDSTQYNEKFKGKATLTTDTSTSTAYMELSSLRSEDTAVY
FCARQTTGTWFAYWGQGTLVTVSSGGGGSGGGGSGGGGSEIVMTQSP
ATLSVSPGERVTLSCRASQSISDYLYWYQQKSHESPRLLIKYASQSI
SGIPARFSGSGSGSEFTLTINSVEPEDVGVYYCQNGHSFPLTFGQGT
KLELKR SEQ ID NO.: 25 (hu8H9 4.1 scFv) is
QVQLVQSGAEVVKPGASVKVSCKASGYTFTNYDINWVRQRPEQGLEW
IGWIFPGDGSTQYNEKFKGRVTMTTDTSTSTVYMELSSLRSEDTAVY
FCARQTTATWFAYWGQGTLVTVSSGGGGSGGGGSGGGGSEIVMTQSP
ATLSVSPGERVTLSCRASQSISDYLHWYQQKSHQAPRLLIKYASQSI
SGIPARFSGSGSGSEFTLTISSLQPEDFGVYYCQNGHSFPLTFGQGT
KLELKR SEQ ID NO.: 26 (hu8H9 5.1 scFv) is
QVQLVQSGAEVVKPGASVKVSCKTSGYTFTNYDINWVRQRPGQGLEW
IGWIFPGDDSTQYNEKFKGRVTMTTDTSTSTVYMELSSLRSEDTAVY
FCARQTTGTWFAYWGQGTLVTVSSGGGGSGGGGSGGGGSEIVMTQSP
ATLSVSPGERVTLSCRASQSISDYLYWYQQKSHQAPRLLIKYASQSI
SGIPARFSGSGSGSEFTLTISSLQPEDFGVYYCQNGHSFPLTFGQGT
KLELKR SEQ ID NO.: 27 (ch8H9 6.1 scFv) is
QVQLQQSGAELVKPGASVKLSCKTSGYTFTNYDINWVRQRPGQGLEW
IGWIFPGDDSTQYNEKFKGKATLTTDTSSSTAYMQLSRLTSEDSAVY
FCARQTTGTWFAYWGQGTLVTVSAGGGGSGGGGSGGGGSDIVMTQSP
ATLSVTPGDRVTLSCRASQSISDYLYWYQQKSHESPRLLIKYASQSI
SGIPSRFSGSGSGSDFTLSINSVEPEDVGVYYCQNGHSFPLTFGAGT
KLELKR SEQ ID NO.: 28 (linker huOKT3 (anti-CD3) scFv) is
GGGGSGGGGSGGGGSQVQLVQSGGGVVQPGRSLRLSCKASGYTFTRY
TMHWVRQAPGKGLEWIGYINPSRGYTNYNQKFKDRFTISRDNSKNTA
FLQMDSLRPEDTGVYFCARYYDDHYCLDYWGQGTPVTVSSGGGGSGG
GGSGGGGSDIQMTQSPSSLSASVGDRVTITCSASSSVSYMNWYQQTP
GKAPKRWIYDTSKLASGVPSRFSGSGSGTDYTFTISSLQPEDIATYY
CQQWSSNPFTFGQGTKLQITR SEQ ID NO.: 29 (linker C825 (anti-DOTA) scFv) is
GGGGSGGGGSGGGGSHVKLQESGPGLVQPSQSLSLTCTVSGFSLTDY
GVHWVRQSPGKGLEWLGVIWSGGGTAYNTALISRLNIYRDNSKNQVF
LEMNSLQAEDTAMYYCARRGSYPYNYFDAWGCGTTVTVSSGGGGSGG
GGSGGGGSQAVVIQESALTTPPGETVTLTCGSSTGAVTASNYANWVQ
EKPDHCFTGLIGGHNNRPPGVPARFSGSLIGDKAALTIAGTQTEDEA
IYFCALWYSDHWVIGGGTRLTVLG Bispecific Antibodies Bispecific antibodies are widely known and used in the art. Bispecific antibodies are artificial proteins that include fragments from two or more different antibodies and consequently bind to two or more different types of antigens.

In some embodiments of the present invention, bispecific antibodies include two different heavy and two different light chains.

In some embodiments of the present invention, a bispecific antibody agent, for example a bispecific antibody, has two specificities, one of which binds B7H3 and the other one of which binds CD3 on T cells or DOTA.

In some embodiments of the present invention, an immunoglobulin light chain described herein is fused to a polypeptide as set forth in SEQ ID NO.: 30 or SEQ ID NO.: 31 (set forth below). SEQ ID NO.: 30 includes a peptide linker sequence and a peptide sequence of an scFv binding huOKT3 (anti-CD3), which is part of the T cell receptor complex. Similarly, SEQ ID NO.: 31 includes a peptide linker sequence and a peptide sequence of an anti-DOTA C825 scFv antibody fragment. Resulting light chain-scFv fusion proteins are then combined with any of the heavy chains described herein.

SEQ ID NO.: 30 (linker huOKT3 (anti-CD3) scFv)
GGGGSGGGGSGGGGSQVQLVQSGGGVVQPGRSLRLSCKASGYTFTRY
TMHWVRQAPGKGLEWIGYINPSRGYTNYNQKFKDRFTISRDNSKNTA
FLQMDSLRPEDTGVYFCARYYDDHYCLDYWGQGTPVTVSSGGGGSGG
GGSGGGGSDIQMTQSPSSLSASVGDRVTITCSASSSVSYMNWYQQTP
GKAPKRWIYDTSKLASGVPSRFSGSGSGTDYTFTISSLQPEDIATYY
CQQWSSNPFTFGQGTKLQITR SEQ ID NO.: 31 (linker C825 (anti-DOTA) scFv)
GGGGSGGGGSGGGGSHVKLQESGPGLVQPSQSLSLTCTVSGFSLTDY
GVHWVRQSPGKGLEWLGVIWSGGGTAYNTALISRLNIYRDNSKNQVF
LEMNSLQAEDTAMYYCARRGSYPYNYFDAWGCGTTVTVSSGGGGSGG
GGSGGGGSQAVVIQESALTTPPGETVTLTCGSSTGAVTASNYANWVQ
EKPDHCFTGLIGGHNNRPPGVPARFSGSLIGDKAALTIAGTQTEDEA
IYFCALWYSDHWVIGGGTRLTVLG The fusion of immunoglobulin light chains with SEQ ID NO.: 30 or SEQ ID NO.: 31, and the subsequent pairing with an immunoglobulin heavy chain creates bispecific antibodies binding to different types of antigens. It is understood that the generation of antibody fusion proteins is standard in the art and routinely done using widely known and used molecular biological techniques. Bispecific antibodies may be used, for example, to tether tumor cells and immune cells to each other (one of the bound antigens is located on the tumor cell and the other antigen is located on the immune cell).

Conjugates

In some embodiments, an antibody agent as described herein is associated with a payload entity. In some embodiments, a payload entity is or comprises a therapeutic agent; in some embodiments, a payload entity is or comprises a detection agent.

Therapeutic Agents

Therapeutic agents can be or comprise any class of chemical entity including, for example, but not limited to, proteins, carbohydrates, lipids, nucleic acids, small organic molecules, non-biological polymers, metals, ions, radioisotopes, etc. In some embodiments, therapeutic agents for use in accordance with the present invention may have a biological activity relevant to the treatment of one or more symptoms or causes of cancer. In some embodiments, therapeutic agents for use in accordance with the present invention may have a biological activity relevant to modulation of the immune system and/or enhancement of T-cell mediated cytotoxicity and/or suppression of the inhibitory effect of B7H3 on T cell proliferation and function. In some embodiments, therapeutic agents for use in accordance with the present invention have one or more other activities.

In some embodiments of the present invention, the conjugated therapeutic agent is a radioisotope, a drug conjugate, a nanoparticle, an immune-toxin, or any other therapeutic payload.

Detection Agents

A detection agent comprises any moiety that may be detected using an assay, for example due to its specific functional properties and/or chemical characteristics. Non-limiting examples of such agents include enzymes, radiolabels, haptens, fluorescent labels, phosphorescent molecules, chemiluminescent molecules, chromophores, luminescent molecules, photoaffinity molecules, colored particles or ligands, such as biotin.

Many detection agents are known in the art, as are systems for their attachment to antibodies (see, for e.g., U.S. Pat. Nos. 5,021,236; 4,938,948; and 4,472,509, each incorporated herein by reference). Examples of such detection agents include paramagnetic ions, radioactive isotopes, fluorochromes, NMR-detectable substances, X-ray imaging agents, among others. For example, in some embodiments, a paramagnetic ion is one or more of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), erbium (III), lanthanum (III), gold (III), lead (II), and/or bismuth (III).

The radioactive isotope may be one or more of actinium-225, astatine-211, bismuth-212, carbon-14, chromium-51, chlorine-36, cobalt-57, cobalt-58, copper-67, Europium-152, gallium-67, hydrogen-3, iodine-123, iodine-124, iodine-125, iodine-131, indium-111, iron-59, lead-212, lutetium-177, phosphorus-32, radium-223, radium-224, rhenium-186, rhenium-188, selenium-75, sulphur-35, technicium-99m, thorium-227, yttrium-90, and zirconium-89. Radioactively labeled antibody agents may be produced according to well-known technologies in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Provided antibody agents may be labeled with technetium-99m by ligand exchange process, for example, by reducing pertechnate with stannous solution, chelating the reduced technetium onto a Sephadex column and applying the antibody to this column. In some embodiments, provided antibody agents are labeled using direct labeling techniques, e.g., by incubating pertechnate, a reducing agent such as $SNC1_2$, a buffer solution such as sodium-potassium phthalate solution, and the antibody. Intermediary functional groups which are often used to bind radioisotopes which exist as metallic ions to antibody are diethylenetriaminepentaacetic acid (DTPA), or ethylene diaminetetracetic acid (EDTA), or 1,4,7,10-tetraazacyclododecane-1,4,7,10-tetraacetic acid (DOTA), or p-aminobenzyl-DOTA (DOTA-Bn). Radioactive isotopes may be detected by, for example, dosimetry.

A fluorescent label may be or may comprise one or more of Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red, among others.

In some embodiments of the present invention, the conjugated detection agent is a diagnostic or imaging agent.

Preparing Conjugates

Several technologies are known in the art for the attachment or conjugation of an antibody agent to a therapeutic or detection agent. Some attachment technologies involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Provided antibody agents may also be reacted with an enzyme in the presence of a coupling agent such as glutaraldehyde or periodate. Conjugates with fluorescein markers, for example, are prepared in the presence of these coupling agents or by reaction with an isothiocyanate.

Identification and/or Characterization of Useful Anti-B7H3 Antibody Agents

The present disclosure provides the first demonstration that antibody agents, including 8H9 antibody agents, that target the FG-loop of B7H3, can be used to block the immune-inhibitory function of B7H3. The present disclosure therefore demonstrates the desirability of identifying and/or characterizing antibody agents with such activity. The present disclosure also provides a variety of systems for performing such identifying and/or characterizing. In some embodiments, for example, binding is directly assessed. In some embodiments, effect on T cell proliferation, activation and/or function is assessed. In some embodiments, immune modulation is assessed. In some embodiments, immune checkpoint inhibition and/or blockade is assessed. In some embodiments, tumor cell death, tumor cell targeting and/or effector cell killing is assessed. In some embodiments, competition with an 8H9 antibody agent as described herein is assessed. In some embodiments, therapeutic efficacy as compared to an 8H9 antibody agent as described herein is assessed.

Compositions

The present invention also provides a pharmaceutical composition including an antibody agent, scFv, or humanized antibody or antigen-binding fragment thereof and a pharmaceutically acceptable carrier.

Pharmaceutical compositions provided herein may be provided in a sterile injectable form (e.g., a form that is suitable for subcutaneous injection or intravenous infusion). For example, in some embodiments, pharmaceutical compositions are provided in a liquid dosage form that is suitable for injection. In some embodiments, pharmaceutical compositions are provided as powders (e.g. lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

The pharmaceutical compositions contemplated as part of the present invention are not limited to pharmaceutical compositions that are injectable, but include all types of pharmaceutical compositions commonly known and used in the art.

In some embodiments, provided pharmaceutical compositions comprise one or more pharmaceutically acceptable excipients. In some embodiments, pharmaceutical compositions comprise one or more preservatives. In some embodiments, pharmaceutical compositions comprise no preservative. Excipients as used herein may be or comprise solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, Md., 2006) discloses a variety of excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, pharmaceutical compositions are provided in a form that can be refrigerated and/or frozen. In some embodiments, pharmaceutical compositions are provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer).

Liquid dosage forms and/or reconstituted solutions may comprise particulate matter and/or discoloration prior to administration. In some embodiments, a solution should not be used if discolored or cloudy and/or if particulate matter remains after filtration.

Formulations of the pharmaceutical compositions described herein may be prepared by any method known or hereafter developed in the art of pharmacology. In some embodiments, such preparatory methods include the step of bringing active ingredient into association with one or more excipients and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to a dose, which would be administered to a subject and/or a convenient fraction of such a dose such as, for example, one-half or one-third of such a dose.

Relative amounts of active ingredient, pharmaceutically acceptable excipient, and/or any additional ingredients in a pharmaceutical composition in accordance with the invention may vary, depending upon the identity, size, and/or condition of the subject treated and/or depending upon the route by which the composition is to be administered. By way of example, the composition may comprise between 0.1% and 100% (w/w) active ingredient.

Uses

Treating Cancer & Relieving Immunosuppression

The present invention also provides methods of treating cancer by administering to a patient in need thereof a therapeutically effective amount of an antibody agent, scFv, or humanized antibody or antigen-binding fragment of thereof. Whether the administration of an antibody agent treats cancer can be determined by known methodologies, including those described in the Examples herein.

The present invention also provides methods of modulating the immune system and/or enhancing T-cell mediated cytotoxicity and/or suppressing the inhibitory effect of B7H3 on T cell proliferation and function in a subject by administering to a patient in need thereof a therapeutically effective amount of an antibody agent, scFv, or humanized antibody or antigen-binding fragment of thereof. Whether the administration of an antibody agent modulates the immune system and/or enhances T-cell mediated cytotoxicity can be determined by known methodologies, including those described in the Examples herein.

In some embodiments, the present invention provides methods of modulating the immune system and/or enhancing NK cell mediated functions and/or suppressing the inhibitory effect of B7H3 on NK cell activity and/or function in a subject, for example by administering to a patient in need thereof a therapeutically effective amount of an antibody agent, scFv, or humanized antibody or antigen-binding fragment thereof. Whether the administration of an antibody agent modulates the immune system and/or enhances NK cell activity and/or function can be determined by known methodologies, including those described herein.

In some embodiments, the exact amount administered may vary from subject to subject, depending on one or more factors as is well known in the medical arts. Such factors may include, for example, one or more of species, age, general condition of the subject, severity of the infection, particular composition, its mode of administration, its mode of activity, the disorder being treated and the severity of the disorder; the activity of the specific antibody agent employed; the specific pharmaceutical composition administered; the half-life of the composition after administration; the age, body weight, general health, sex, and diet of the subject; the time of administration, route of administration, and rate of excretion of the specific compound employed; the duration of the treatment; drugs used in combination or coincidental with the specific compound employed and the like. Pharmaceutical compositions may be formulated in dosage unit form for ease of administration and uniformity of dosage. It will be understood, however, that the total daily usage of the compositions of the present invention will be decided by the attending physician within the scope of sound medical judgment.

In some embodiments, the exact amount administered may be an amount of an antibody agent as described herein to effectively achieve one or more modulating effects described herein, which, at least in some embodiments, includes modulating B7H3 suppression, inhibition or blockade of T and/or NK cell activity and/or function.

Antibody agents in accordance with the present invention and pharmaceutical compositions thereof in accordance with the present invention may be administered according to any appropriate route and regimen. In some embodiments, a route or regimen is one that has been correlated with a positive therapeutic benefit. In some embodiments, a route or regimen is one that has been approved by the FDA and/or EP.

Pharmaceutical compositions of the present invention may be administered by any route, as will be appreciated by those skilled in the art. In some embodiments, pharmaceutical compositions of the present invention are administered by oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical (e.g., by powders, ointments, creams, gels, lotions, and/or drops), mucosal, intranasal, buccal, enteral, vitreal, sublingual; by intratracheal instillation, bronchial instillation, and/or inhalation; as an oral spray, nasal spray, and/or aerosol, and/or through a portal vein catheter.

In some embodiments, antibody agents in accordance with the present invention and/or pharmaceutical compositions thereof may be administered intravenously, for example, by intravenous infusion. In specific embodiments, antibody agents in accordance with the present invention and/or pharmaceutical compositions thereof may be administered by intramuscular injection. In specific embodiments, antibody agents in accordance with the present invention and/or pharmaceutical compositions thereof may be administered by subcutaneous injection. In specific embodiments, antibody agents in accordance with the present invention and/or pharmaceutical compositions thereof may be administered via portal vein catheter. However, the invention encompasses the delivery of antibody agents in accordance with the present invention and/or pharmaceutical compositions thereof by any appropriate route taking into consideration likely advances in the sciences of drug delivery.

In some embodiments, antibody agents in accordance with the present invention and/or pharmaceutical compositions thereof in accordance with the invention may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg of subject body weight per day to obtain the desired therapeutic effect. The desired dosage may be delivered more than three times per day, three times per day, two times per day, once per day, every other day, every third day, every week, every two weeks, every three weeks, every four weeks, every two months, every six months, or every twelve months. In certain embodiments, the desired dosage may be delivered using multiple administrations (e.g., two, three, four, five, six, seven, eight, nine, ten, eleven, twelve, thirteen, fourteen, or more administrations).

Combination Therapy

It will be appreciated by the person having ordinary skill in the art that antibody agents in accordance with the present invention and/or pharmaceutical compositions thereof can be employed in combination therapies.

The particular combination of therapies (e.g., therapeutics or procedures) to employ in a combination regimen will take into account compatibility of the desired therapeutics and/or procedures and the desired therapeutic effect to be achieved. It will also be appreciated that pharmaceutical compositions of the present invention can be employed in combination therapies (e.g., combination antibody therapies), that is, the pharmaceutical compositions can be administered concurrently with, prior to, or subsequent to, one or more other desired therapeutic procedures.

Therapeutically effective amounts of antibody agents in accordance with the invention may be combined with, in a provided pharmaceutical composition, at least one other active ingredient. In some embodiments, another active ingredient is an anti-cancer agent, monoclonal antibody, polyclonal antibody, RNA polymerase inhibitors, protease inhibitors, helicase inhibitors, immunomodulators, antisense compounds, short interfering RNAs, short hairpin RNAs, micro RNAs, RNA aptamers, ribozymes, and combinations thereof. The particular combination of therapies to employ in a combination regimen will generally take into account compatibility of the desired therapeutics and/or procedures and the desired therapeutic effect to be achieved. It will also be appreciated that the therapies employed may achieve a desired effect for the same disorder, or they may achieve different effects.

It will be appreciated that the therapies employed may achieve a desired effect for the same purpose, or they may achieve different effects (e.g., control of any adverse effects). The invention encompasses the delivery of pharmaceutical compositions in combination with agents that may improve their bioavailability, reduce and/or modify their metabolism, inhibit their excretion, and/or modify their distribution within the body.

In some embodiments, agents utilized in combination will be utilized at levels that do not exceed the levels at which they are utilized individually. In some embodiments, the levels utilized in combination will be lower than those utilized individually.

In some embodiments, combination therapy may involve administrations of a plurality of antibody agents directed to a single epitope (e.g. a single conformational epitope). In some embodiments, combination therapy can comprise a plurality of antibody agents that recognize distinct epitopes, for example to simultaneously interfere with multiple mechanisms in the process tumorigenesis.

It will be appreciated by one of skill in the art that any permutation or combination of antibody agents in accordance with the present invention can be combined with any other antibody agent to formulate compositions and/or combination therapy regimens comprising a plurality of different antibody agents.

Nucleic Acids

In certain embodiments, the present invention provides nucleic acids (which includes DNA and RNA, for example) that encode an antibody agent described herein. In some embodiments, the invention provides nucleic acids that are complementary to nucleic acids that encode an antibody agent described herein.

In some embodiments, the invention provides nucleic acid molecules that hybridize to nucleic acids encoding an antibody agent. Such nucleic acids can be used, for example, as primers or as probes. To give but a few examples, such nucleic acids can be used as primers in polymerase chain reaction (PCR), as probes for hybridization (including in situ hybridization), and/or as primers for reverse transcription-PCR (RT-PCR).

In certain embodiments, nucleic acids can be DNA or RNA, and can be single stranded or double-stranded. In some embodiments, nucleic acids may include one or more non-natural nucleotides. In some embodiments, nucleic acids include only natural nucleotides.

The generation and manipulation of nucleic acids encoding antibody agents, and in particular antibodies and epitope-binding fragments thereof, is known in the art and described in, for example but not limited to, Green & Sambrook, Molecular Cloning: A Laboratory Manual, Cold Spring Harbor Laboratory Press 2012.

The nucleic acids described herein can be cloned into any one of the many expression vectors and systems known in the art, and then transfected into cells of choice to express the nucleic acids in tissue culture, using technologies widely known in the art. Non-limiting examples of cells within the scope of the invention in this regard are immune cells generally, and T cells and other antigen presenting cells more in particular. See, e.g., Green & Sambrook, Molecular Cloning: A Laboratory Manual, Cold Spring Harbor Laboratory Press 2012.

The following examples further illustrate the invention, but should not be construed to limit the scope of the invention in any way.

All patent and non-patent references cited herein are incorporated herein by reference in their entirety.

EXAMPLES

Results
Crystallization of ch8H9

The crystal structure of ch8H9 Fab fragment was determined by molecular replacement using PDB entry (3D85) and refined to 2.5 Å resolution. Collection and refinement statistics are set forth in Table 2 (statistics for the highest-resolution shell are shown in parentheses). The final model was deposited in the Protein Data Bank (access code 5CMA).

The ch8H9 Fab structure has immunoglobulin fold domains common to all Fab structures, and the six CDR loops (H1, H2, H3, L1, L2 and L3) that form the antigen recognition site had well defined electron densities (see FIG. 1). The electrostatic surface potential of the antigen-binding site was calculated using DelPhi (FIG. 1C; Rocchia, W. et al., 2002, J. Comput. Chem. 23:128-137). The center of the binding site has a large area of positively charged surface area dominated by the L3 and H3 loops. Two pockets of negatively charged surface area (at the H2 and L1 loop regions) flank the central region, indicating that the antigen recognized by 8H9 has a mixed surface charge distribution.

TABLE 2

| | |
|---|---|
| Wavelength (Å) | 0.9795 |
| Resolution range (Å) | 29-2.495 (2.584-2.495) |
| Space group | C 2 2 2$_1$ |
| Unit cell (Å) | 64.576, 207.422, 85.491 |
| Unit Cell (°) | 90, 90, 90 |
| Unique reflections | 20043 (1957) |
| Completeness (%) | 98.03 (97.12) |
| Mean I/sigma(I) | 10.18 (2.30) |
| Wilson B-factor | 55.01 |
| R-work | 0.2080 (0.3037) |
| R-free | 0.2606 (0.3421) |
| Number of non-hydrogen atoms | 3303 |

TABLE 2-continued

| | |
|---|---|
| macromolecules | 3254 |
| water | 49 |
| Protein residues | 426 |
| RMS (bonds) | 0.003 |
| RMS (angles) | 0.87 |
| Ramachandran favored (%) | 94.0 |
| Ramachandran allowed (%) | 4.6 |
| Ramachandran outliers (%) | 1.4 |
| Average B-factor | 69.70 |
| macromolecules | 69.90 |
| solvent | 58.50 |

Humanization of m8H9

The CDRs of the heavy and light chains of m8H9 were grafted onto IgG1 frameworks based on their homology to human germline sequences IGHV1-46 for the heavy chain and IGKV-7 for the light chain. Two versions, H1 and H2, of the humanized heavy chain were generated, with H1 containing more human template sequences. Two versions, L1 (SEQ ID NO.: 2) and L2 (SEQ ID NO.: 3), of the humanized light chain were also generated, with L1 containing more human template sequences. Four versions of the humanized 8H9 IgG1 antibody were then cloned, expressed, and purified (H1L1 [SEQ ID NO.: 10, SEQ ID NO.: 2], H1L2 [SEQ ID NO.: 10, SEQ ID NO.: 3], H2L1 [SEQ ID NO.: 11, SEQ ID NO.: 2], and H2L2 [SEQ ID NO.: 11, SEQ ID NO.: 3]), along with a chimeric (ch) 8H9 IgG1.

Figure 3:
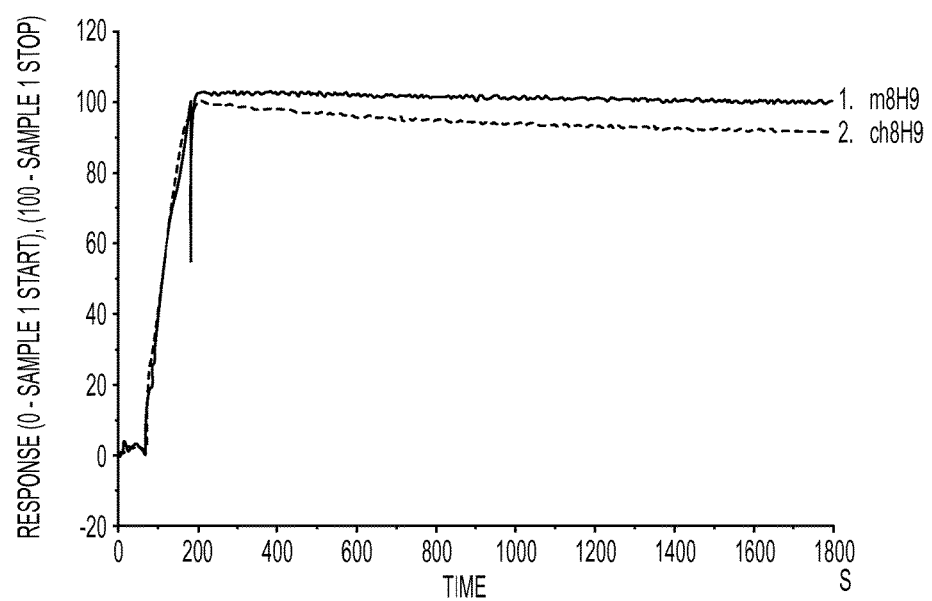
FIG. 3 shows the kinetics of the binding of murine 8H9 (m8H9) and mouse/human chimeric 8H9 (ch8H9) IgG antibodies to 2Ig-B7H3-Fc as determined by surface plasmon resonance.

FIG. 3 and Table 3 below show the binding properties of m8H9 and ch8H9 against B7H3 as determined by surface plasmon resonance. Both antibodies had very similar binding kinetics (0.28 nM $K_D$ and 0.74 nM, respectively).

Figure 4:
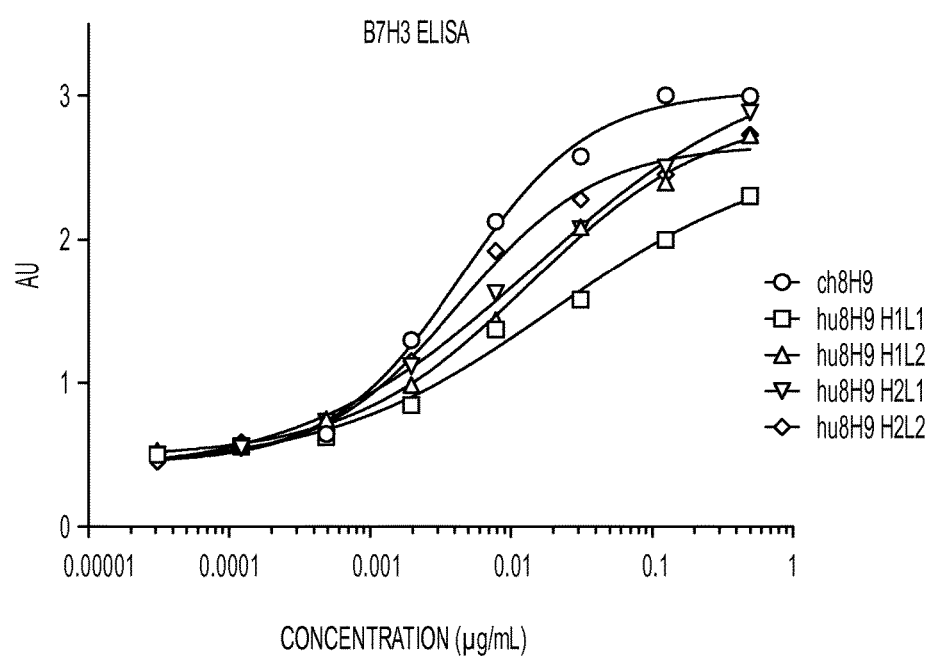
FIG. 4 shows the results of an ELISA in which a variety of concentrations of ch8H9 and of the humanized 8H9 IgG variants H1L1, H1L2, H2L1 and H2L2 were bound to 4Ig-B7H3.

FIG. 4 and Table 4 below show the binding properties of the four humanized 8H9 (hu8H9) IgG1s. Variant H1L1 (SEQ ID NO.: 10, SEQ ID NO.: 2), which contained the most human content, bound to B7H3 more weakly (112 nM $K_D$) than the three other variants, which, however, also displayed only suboptimal binding capacity (34.8-38.6 nM $K_D$.

TABLE 3

Kinetics of the binding of m8H9 and ch8H9 to 2Ig-B7H3-mFc as determined by surface plasmon resonance

| Construct | $K_{on}$ (S$^{-1}$M$^{-1}$) | $K_{off}$ (S$^{-1}$) | $K_D$ (nM) |
|---|---|---|---|
| m8H9 | 3.674 × 10$^4$ | 1.033 × 10$^{-5}$ | 0.28 |
| ch8H9 | 4.738 × 10$^4$ | 3.506 × 10$^{-5}$ | 0.74 |

TABLE 4

Kinetics of the binding of hu8H9 variants to 4Ig-B7H3 as determined by surface plasmon resonance

| | 4Ig-B7H3 | | |
|---|---|---|---|
| Antibody | $k_{on}$ | $k_{off}$ | $K_D$ (nM) |
| hu8H9-H1L1 IgG1 | 2.61 × 10$^4$ | 1.86 × 10$^{-3}$ | 111.8 |
| hu8H9-H1L2 IgG1 | 3.64 × 10$^4$ | 1.27 × 10$^{-3}$ | 34.8 |
| hu8H9-H2L1 IgG1 | 4.08 × 10$^4$ | 1.35 × 10$^{-3}$ | 34.8 |
| hu8H9-H2L2 IgG1 | 4.40 × 10$^4$ | 1.66 × 10$^{-3}$ | 38.6 |

To improve the binding of hu8H9 to B7H3, a structural model of m8H9 was generated and simulated using CHARMm force fields. In silico mutagenesis was performed to analyze the effects of every single possible humanizing mutation. Table 5 below shows the 6 mutations (Light chain: S20T, S69T, L106I; Heavy chain: V12K, R40A, E42G) in the framework region that would lead to destabilization of the inherent structure of m8H9. The reverse of these 6 mutations (Light chain: T20S, T69S, I106L; Heavy chain: K12V, A40R, G42E) were introduced into hu8H9 H1L2 to create hu8H9 H3L3 (SEQ ID NO.: 12, SEQ ID NO.: 4). The mutations were made based on in silico energy calculations, which is a non-standard method of antibody humanization and optimization. The standard method of antibody humanization involves CDR grafting and making back mutations based on sequence homology and proximity to CDR residues. Constructs H1L1, H1L2, H2L1, and H2L2 were made by standard CDR grafting methods.

TABLE 5

In silico mutational analysis of m8H9 homology model used to design hu8H9 H3L3

| Mouse residue | Mutation | Weighted mutation energy (kcal/mol) | Effect |
| --- | --- | --- | --- |
| LC: Ser20 | Thr | +1.181 | Destabilizing |
| LC: Ser69 | Thr | +0.759 | Destabilizing |
| LC: Leu106 | Ile | +2.078 | Destabilizing |
| HC: Val12 | Lys | +5.563 | Destabilizing |
| HC: Arg40 | Ala | +1.170 | Destabilizing |
| HC: Glu42 | Gly | +0.695 | Destabilizing |

Subsequent to the design of hu8H9 H3L3 (SEQ ID NO.: 12, SEQ ID NO.: 4) based on homology modeling, the crystal structure of the ch8H9 Fab fragment was resolved at 2.5 Å. In an effort to increase the human content of hu8H9 H3L3, the crystal structure of the ch8H9 Fab fragment was simulated with CHARMm force fields and in silico mutagenesis was performed to analyze the effects of every single possible humanizing mutation once again. Table 6 and Table 7, both below, show 7 mutations in the light chain (S20T, E42Q, S43A, N76S, V78L, E79Q, V83F) and 5 mutations in the heavy chain (L20V, K67R, A68V, L70M, and A79V) that were predicted to stabilize the 8H9 structure. These 12 humanizing mutations were incorporated into hu8H9 H3L3 to generate hu8H9 4.1 (SEQ ID NO.: 14, SEQ ID NO.: 6). These mutations were made based on in silico energy calculations, which is a non-standard method of antibody humanization and optimization.

TABLE 6

In silico mutational analysis of ch8H9 crystal structure used to design hu8H9 4.1 light chain

| Sequence in ch8H9 and H3L3 LC | Sequence of human template | Location | mutation energy (kcal/mol) |
| --- | --- | --- | --- |
| S20 | T | surface | −0.5 |
| E42 | Q | surface | −1.1 |
| S43 | A | $V_H/V_L$ | −4.5 |
| N76 | S | surface | −4.5 |
| V78 | L | internal | −2.8 |
| E79 | Q | surface | −3.8 |
| V83 | F | surface | −2.5 |

TABLE 7

In silico mutational analysis of ch8H9 crystal structure used to design hu8H9 4.1 heavy chain

| Sequence in ch8H9 and H3L3 HC | Sequence of human template | Mutation energy (kcal/mol) |
| --- | --- | --- |
| L20 | V | −0.1 |
| K67 | R | −2.8 |

TABLE 7-continued

In silico mutational analysis of ch8H9 crystal structure used to design hu8H9 4.1 heavy chain

| Sequence in ch8H9 and H3L3 HC | Sequence of human template | Mutation energy (kcal/mol) |
| --- | --- | --- |
| A68 | V | −1.2 |
| L70 | M | −1.0 |
| A79 | V | −1.7 |

Affinity Maturation by Yeast Display

Figure 5:
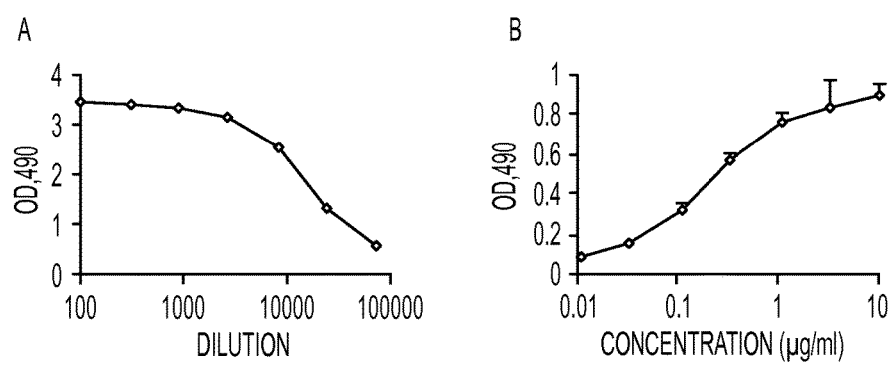
FIG. 5 shows ELISA-detection of biotinylated B7H3-mFc antigen by serially diluted HRP-streptavidin (A) or ch8H9 IgG (B).

A biotinylated B7H3 construct was used to assist in the selection of particularly desirable affinity-matured humanized 8H9 antibodies. For this approach, 4Ig-B7H3 fused to mouse Fc was expressed in DG44 CHO cells. For biotinylation, NHS-activated biotin was used to react efficiently with primary amino groups (–NH2) in the side chain of lysine (K) residues and the N-terminus of the polypeptides. Excess non-reacted biotin was removed by size exclusion using ultrafilter columns. Successful biotinylation of the B7H3-mFc antigen was validated by staining with HRP conjugated streptavidin in an ELISA (FIG. 5A). Detection of biotinylated B7H3-Fc by mouse/human chimeric 8H9 IgG confirmed that the biotin moiety did not hamper specific binding by 8H9 antibody to B7H3-Fc (FIG. 5B).

Figure 6:
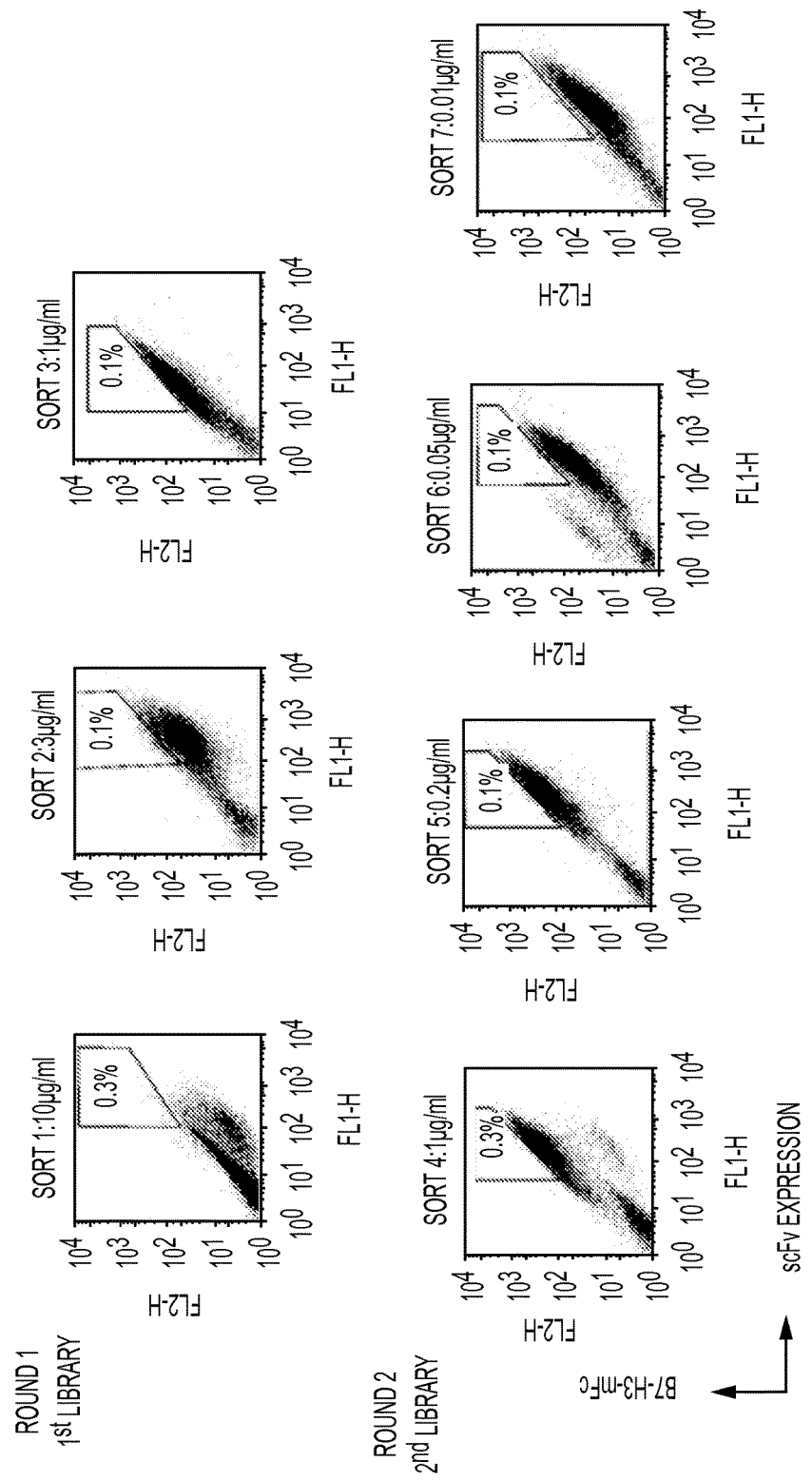
FIG. 6 shows flow cytometric data associated with the affinity maturation of humanized (hu) 8H9 H3L3 scFv.
Figure 7:
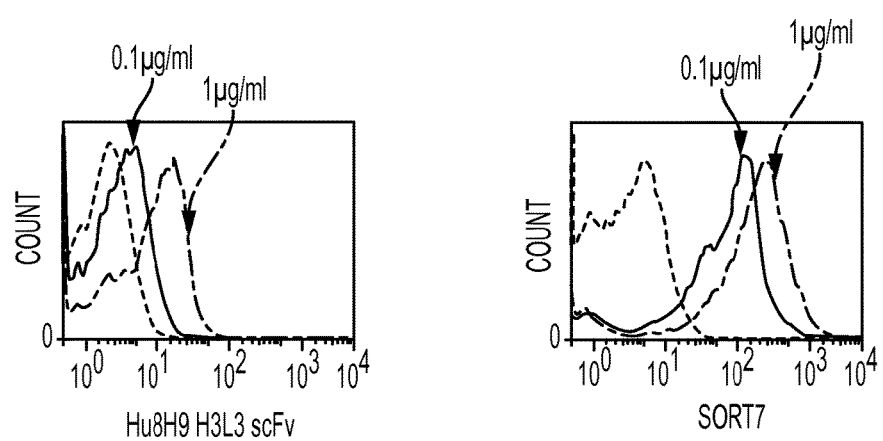
FIG. 7 shows a comparison of yeast cells displaying hu8H9 H3L3 scFv (left) and yeast cells derived from the last/seventh round of cell sorting (right). Yeast cells were stained with 0.1 or 1 µg/ml of B7H3-mFc and then detected by an APC-goat anti-mouse antibody.
Figure 8:
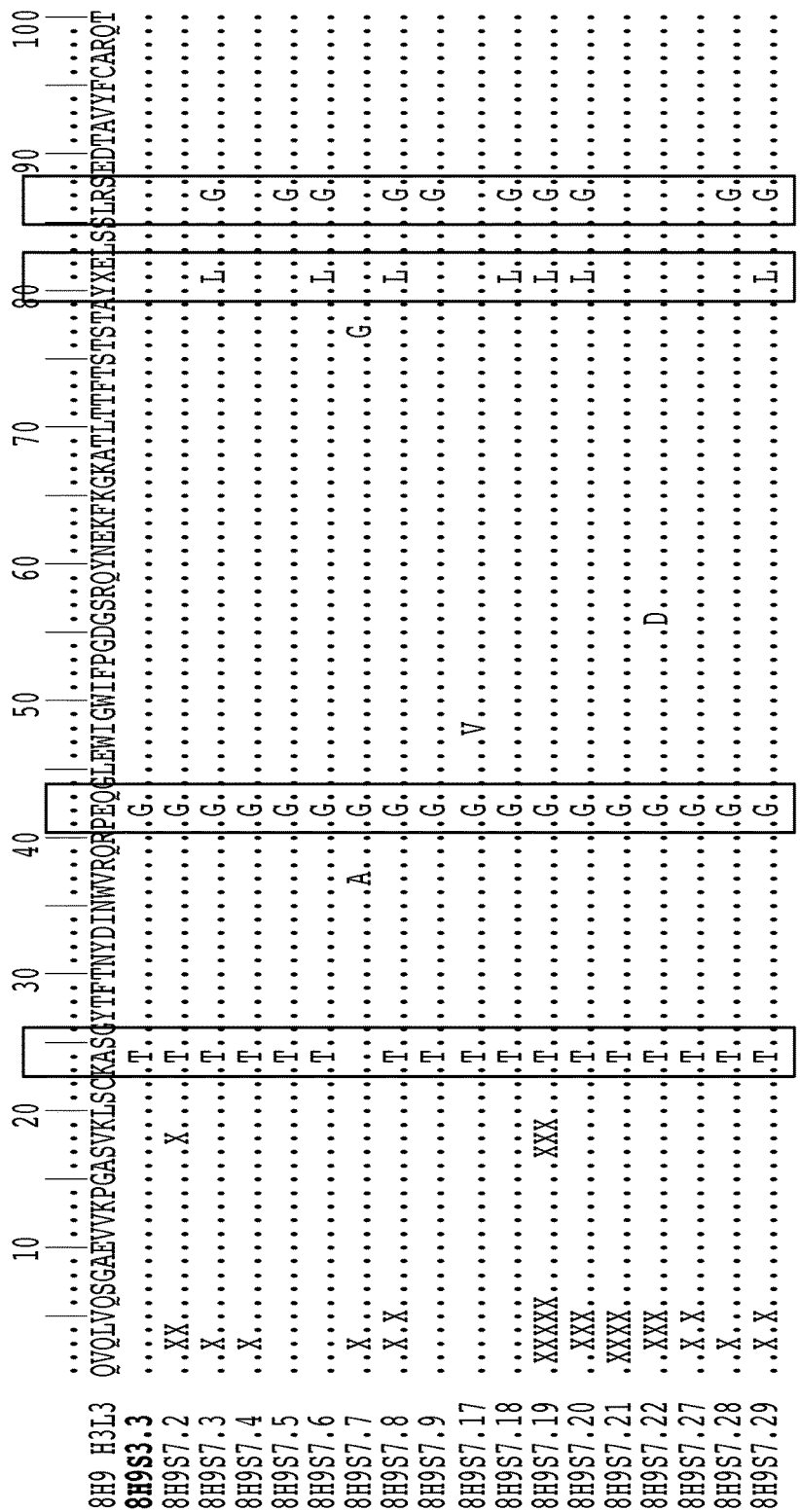
FIG. 8 shows an amino acid sequence alignment for hu8H9 single-chain Fv (scFvs) variants derived from the seventh round of cell sorting as described. Sequence data of strong binders were grouped by cluster analysis. The following five scFv variants were selected repeatedly: S7.2, S7.17, S7.22, S7.28 and S7.29. S3.3 is the scFv derived from the third round of cell sorting. 8H9 H3L3 (SEQ ID NO.:87); 8H9S3.3 (SEQ ID NO.:88); 8H9S7.2 (SEQ ID NO.:89); 8H9S7.3 (SEQ ID NO.:90); 8H9S7.4 (SEQ ID NO.:91); 8H9S7.5 (SEQ ID NO.:92); 8H9S7.6 (SEQ ID NO.:93); 8H9S7.7 (SEQ ID NO.:94); 8H9S7.8 (SEQ ID NO.:95); 8H9S7.9 (SEQ ID NO.:96); 8H9S7.17 (SEQ ID NO.:97); 8H9S7.18 (SEQ ID NO.:98); 8H9S7.19 (SEQ ID NO.:99); 8H9S7.20 (SEQ ID NO.:100); 8H9S7.21 (SEQ ID NO.:101); 8H9S7.22 (SEQ ID NO.:102); 8H9S7.27 (SEQ ID NO.:103); 8H9S7.28 (SEQ ID NO.:104); 8H9S7.29 (SEQ ID NO.:105).
Figure 8:
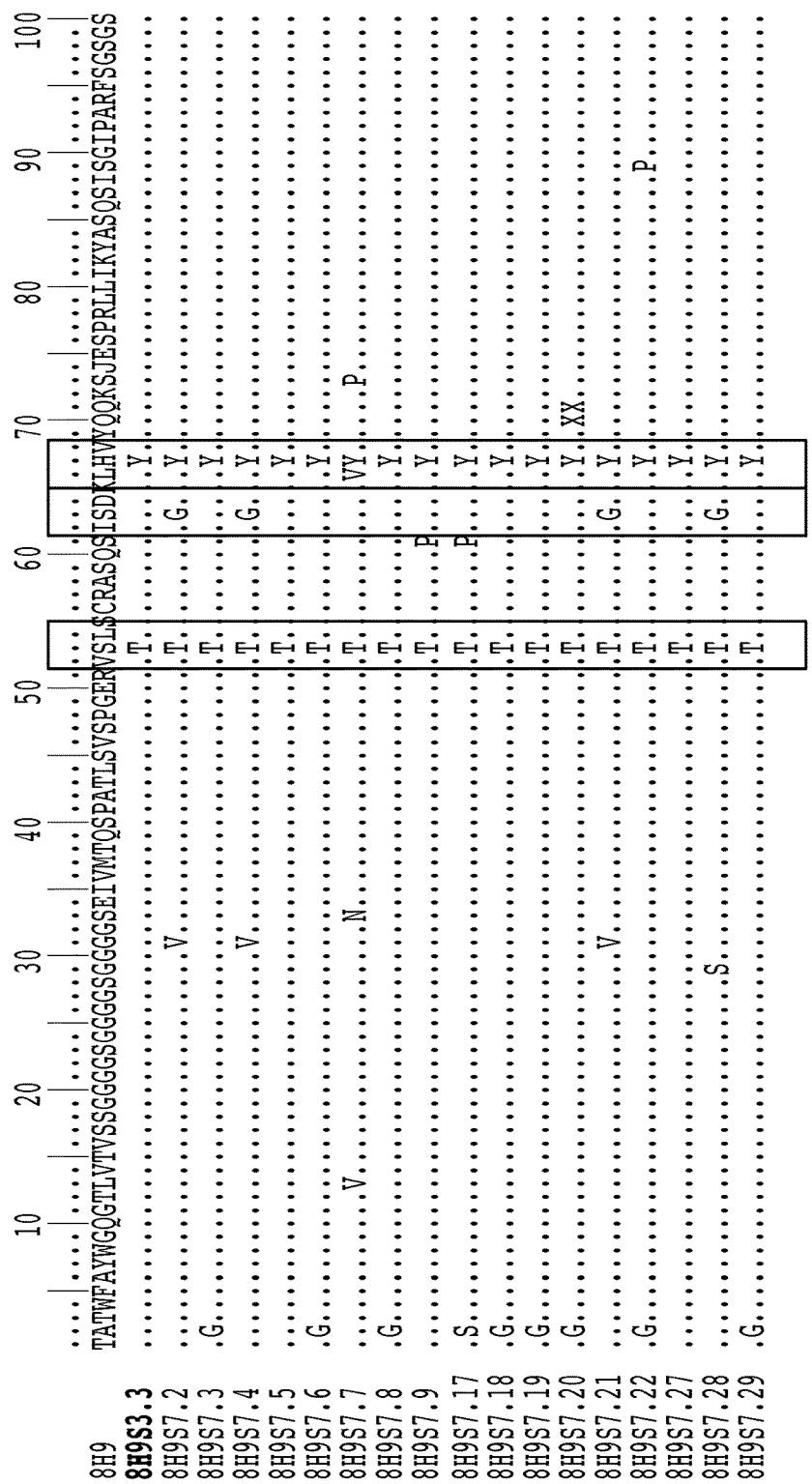

To increase the affinity of humanized hu8H9 H3L3, it was converted to a scFv and randomly mutagenized by error-prone PCR. Previously, we successful used yeast display for further maturation of antibodies because it allows fine discrimination between mutants by flow cytometry. Therefore, the mutant library was displayed on yeast cells by homologous recombination with a vector containing a c-myc tag. A mutant yeast library of relatively large (up to $10^8$) size was generated and subjected first to a pre-selection by using magnetic beads conjugated to biotinylated B7H3-mFc, allowing elimination of yeast cells that did not express antibodies or bound weakly to the antigen. The mutant library was then sorted several times by FACS to select for binding to B7H3 under stringent conditions (FIG. 6). The sorted scFv variants were further mutated by error-prone PCR of the entire gene to yield a new sub-library. The process of sorting and mutagenesis was then cyclically repeated. The clones binding most strongly to B7H3 were obtained from the final round of maturation (FIG. 6). The yeasts derived from the last (the $7^{th}$) round of sorting showed significantly stronger binding than yeast displaying parental hu8H9 H3L3 (SEQ ID NO.: 12, SEQ ID NO.: 4) (FIG. 7), when they were stained with the B7H3-mFc antigen. These results indicated that the enriched yeast mutants had significantly increased binding affinity as compared with the un-mutagenized parent. The highest affinity clones from the final round of maturation were identified. Sequence data of strong binders were grouped by cluster analysis. The following scFv variants were selected repeatedly: S7.2 (SEQ ID NO.: 19), S7.17 (SEQ ID NO.: 20), S7.22 (SEQ ID NO.: 21), S7.28 (SEQ ID NO.: 22) and S7.29 (SEQ ID NO.: 23) (FIG. 8).

Binding Properties of Selected scFv Mutants

Figure 9:
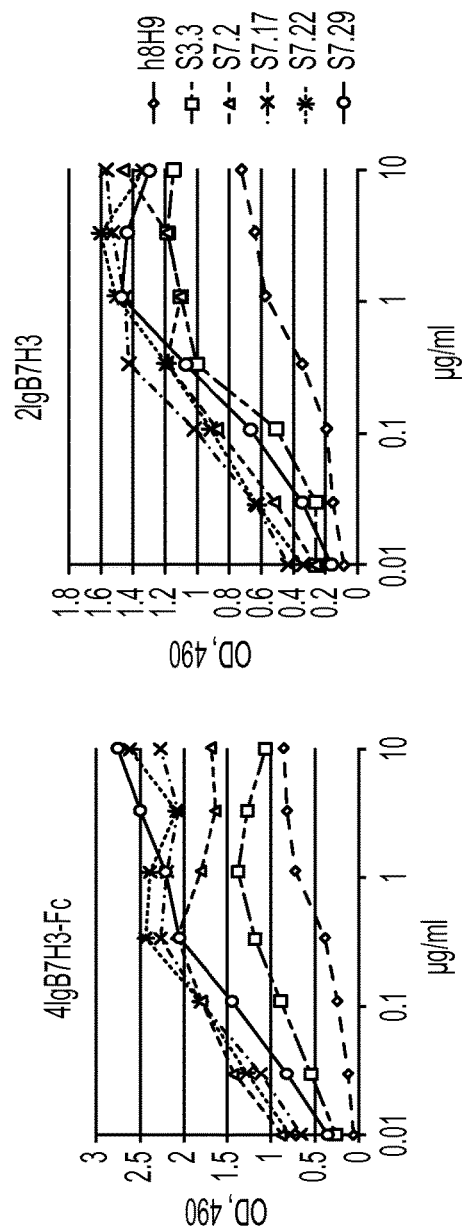
FIG. 9 shows results of ELISA experiments in which hu8H9 scFv variants were bound to 4Ig-B7H3 (left) and 2Ig-B7H3 (right).

In an ELISA, FACS-selected scFv variants exhibited better binding to either the 4Ig or 2Ig forms of B7H3 than that observed with the parental hu8H9 H3L3 or with S3.3 (Sort3) (FIG. 9). The binding of different 8H9 variants to 4Ig-B7H3 antigen-coated onto CMS chips was compared by surface plasmon resonance using Biacore T-100. The obtained $K_D$ values of all selected variants, including hu8H9 H3L3 and S3.3 are listed in Table 8 below.

TABLE 8

Biacore analysis of recombinantly expressed scFv against 4IgB7H3

| scFv construct | $K_{on}(S^{-1}M^{-1})$ | $K_{off}(S^{-1})$ | $K_D$ (nM) |
|---|---|---|---|
| hu8H9 H3L3 | $6.379 \times 10^3$ | $9.185 \times 10^{-4}$ | 144.0 |
| S3.3 | $2.481 \times 10^4$ | $2.443 \times 10^{-4}$ | 9.85 |
| S7.2 | $2.543 \times 10^4$ | $1.432 \times 10^{-4}$ | 5.6 |
| S7.17 | $5.097 \times 10^4$ | $1.134 \times 10^{-4}$ | 2.2 |
| S7.22 | $8.614 \times 10^4$ | $9.989 \times 10^{-5}$ | 1.2 |
| S7.28 | $4.751 \times 10^3$ | $1.318 \times 10^{-3}$ | 277.4 |
| S7.29 | $5.593 \times 10^4$ | $1.519 \times 10^{-4}$ | 2.7 |

The scFv variants from the seventh sort bound to antigen with a dissociation constant ($K_D$) of about 6 nM, 2 nM, 1 nM, 277 nM and 3 nM, compared to the dissociation constants ($K_D$ of 144 nM and 10 nM observed for the parental hu8H9 H3L3 and S3.3, respectively. Among the scFv variants from the seventh sorting, scFv S7.17, S7.22 and S7.29 exhibited the highest binding affinity, achieving a more than 50-fold affinity improvement. scFv S7.22 (SEQ ID NO.: 21) in particular resulted in a more than 100-fold binding improvement compared to the parental hu8H9 H3L3 scFv (SEQ ID NO.: 17).

Immunostaining of Tumor Cells by Affinity Matured scFv Variants

Figure 10:
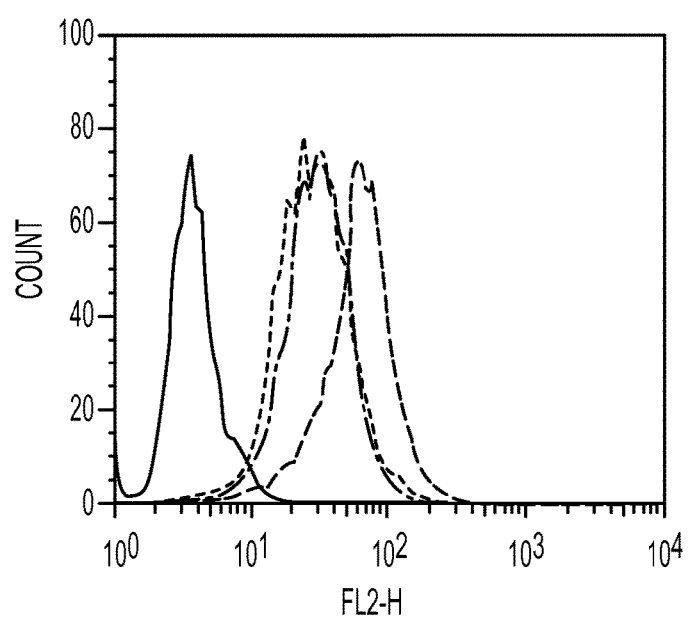
FIG. 10 shows results of experiments in which hu8H9 scFv variants were bound to M14 neuroblastoma cells. Tumor cells were stained with 1 µg/ml of hu8H9 scFv H3L3 (blue), S3.3 (orange), 57.22 (green), or isotype control (red) and an anti-his antibody. Binding was quantitated by flow cytometry.

We compared the binding of the hu8H9 H3L3 (SEQ ID NO.: 17), S3.3 (SEQ ID NO.: 18) and S7.22 (SEQ ID NO.: 21) scFv variants to neuroblastoma M14 cells (FIG. 10). We found that scFv S7.22 showed better binding than scFv variants Hu8H9 and S3.3.

Determination of Key Affinity Enhancing Mutations

Table 9 below lists the six mutations identified from affinity maturation sorted sequences (LC: S20T, LC: H34Y, HC: A24T, HC: E42G, HC: G56D, HC: A102G). Four of the mutations (LC: S20T, LC: H34Y, HC: A24T, HC: E42G) were derived from the third round of sorting (clone S3.3 [SEQ ID NO.: 18]) and subsequently present in most of the clones from the seventh round of sorting.

TABLE 9

Mutations identified from Yeast display affinity maturation

| Mutation | Location |
|---|---|
| LC: S20T | Framework |
| LC: H34Y | CDR L1 |
| HC: A24T | Framework |
| HC: E42G | Framework |
| HC: G56D | CDR H2 |
| HC: A102G | CDR H3 |

The highest affinity clone, S7.22, has two additional mutations (HC: G56D, HC: A102G). Three of the identified mutations are directly in the CDR region (LC: H34Y, HC: G56D, HC: A102G). Two of the mutations (LC: S20T, HC: E42G) are of the same sequence as the human germline template used for humanization.

Affinity Enhanced and Humanized Variants

The six affinity maturation mutations (LC: S20T, LC: H34Y, HC: A24T, HC: E42G, HC: G56D, HC: A102G) were incorporated into the hu8H9 H3L3 sequence (SEQ ID NO.: 12, SEQ ID NO.: 4) to generate hu8H9 3.1 (SEQ ID NO.: 24) scFv and IgG1 variants. The sequence of hu8H9 4.1 (SEQ ID NO.: 25) already contained one of the mutations identified from the affinity maturation (LC: S20T), and the additional five mutations (LC: H34Y, HC: A24T, HC: E42G, HC: G56D, HC: A102G) were incorporated to generate hu8H9 5.1 scFv (SEQ ID NO.: 26) and IgG1 variants.

The binding kinetics of hu8H9 H3L3 (SEQ ID NO.: 17), 3.1 (SEQ ID NO.: 24), 4.1 (SEQ ID NO.: 25), and 5.1 (SEQ ID NO.: 26) scFv variants are presented in Table 10 below.

TABLE 10

Biacore analysis of scFv construct of hu8H9 H3L3, 3.1, 4.1, and 5.1

| scFv construct | $K_{on}(S^{-1}M^{-1})$ | $K_{off}(S^{-1})$ | $K_D$ (nM) |
|---|---|---|---|
| hu8H9 H3L3 | $6.379 \times 10^3$ | $9.185 \times 10^{-4}$ | 144.0 |
| hu8H9 3.1 | $1.035 \times 10^5$ | $9.525 \times 10^{-5}$ | 0.92 |
| hu8H9 4.1 | $1.217 \times 10^4$ | $5.565 \times 10^{-4}$ | 45.7 |
| hu8H9 5.1 | $5.878 \times 10^4$ | $9.841 \times 10^{-5}$ | 1.7 |

As can be seen, the addition of the affinity enhancing mutations resulted in substantially higher binding affinities (0.9 nM $K_D$ for hu8H9 3.1 and 1.7 nM $K_D$ for hu8H9 5.1), by comparison to the binding affinity of non-affinity matured sequences.

Figure 11:
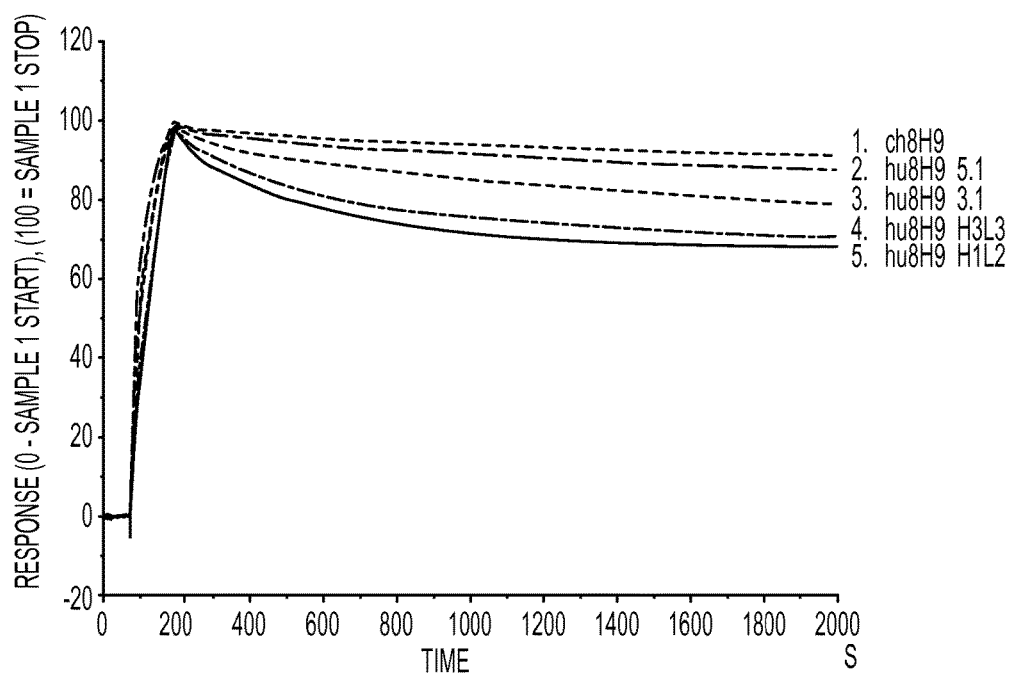
FIG. 11 shows kinetics of binding by IgG antibodies ch8H9 and hu8H9 H1L2, H3L3, 3.1 and 5.1 to 4Ig-B7H3-Fc as determined by surface plasmon resonance.

The kinetics of the binding by IgG1 antibodies ch8H9 (SEQ ID NO.: 9, SEQ ID NO.: 1), H1L2 (SEQ ID NO.: 10, SEQ ID NO.: 3), H3L3 (SEQ ID NO.: 12, SEQ ID NO.: 4), 3.1 (SEQ ID NO.: 13, SEQ ID NO.: 5) and 5.1 (SEQ ID NO.: 15, SEQ ID NO.: 7) to 4Ig-B7H3-Fc are presented in FIG. 11 and Table 11 below.

TABLE 11

Binding kinetics of IgG ch8H9 and hu8H9 H1L2, H3L3, 3.1 and 5.1 to 4Ig-B7H3 as determined by surface plasmon resonance

| Construct | $K_{on}(S^{-1}M^{-1})$ | $K_{off}(S^{-1})$ | $K_D$ (nM) |
|---|---|---|---|
| ch8H9 | $4.481 \times 10^4$ | $5.491 \times 10^{-5}$ | 1.2 |
| hu8H9 H1L2 | $5.596 \times 10^5$ | $2.394 \times 10^{-2}$ | 42.7 |
| hu8H9 H3L3 | $6.827 \times 10^6$ | $4.519 \times 10^{-2}$ | 6.6 |
| hu8H9 3.1 | $5.559 \times 10^4$ | $1.136 \times 10^{-4}$ | 2.0 |
| hu8H9 5.1 | $5.918 \times 10^4$ | $7.081 \times 10^{-5}$ | 1.3 |

Figure 12:
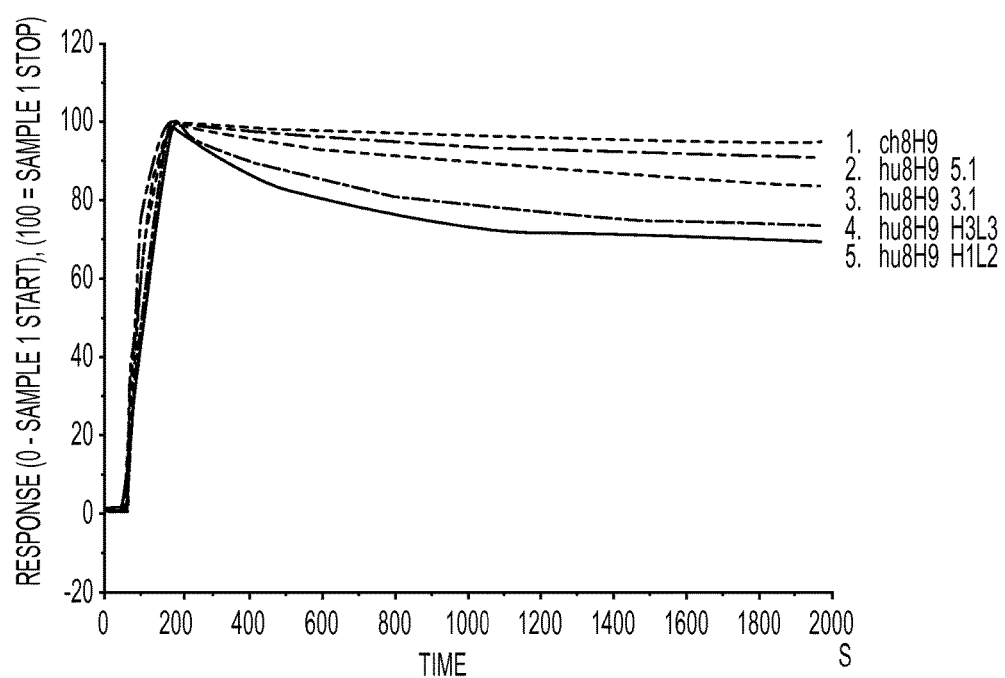
FIG. 12 shows kinetics of the binding by IgG antibodies ch8H9 and hu8H9 H1L2, H3L3, 3.1 and 5.1 to 2Ig-B7H3-mFc as determined by surface plasmon resonance.

The humanized variant H1L2 (SEQ ID NO.: 10, SEQ ID NO.: 3), which was designed by standard CDR grafting technologies, has substantially weaker binding than ch8H9 (SEQ ID NO.: 9, SEQ ID NO.: 1) (42.7 nM $K_D$ for hu8H9 H1L2 and 1.2 nM $K_D$ for ch8H9). As described herein, a novel method of computational modeling based on energy calculations and molecular dynamics simulations was utilized in accordance with the present invention to generate hu8H9 H3L3, resulting in a substantial improvement in affinity (6.6 nM). Incorporation of affinity enhancing mutations resulted in further improvement and resulted in hu8H9 3.1 (SEQ ID NO.: 13, SEQ ID NO.: 5) and 5.1 (SEQ ID NO.: 15, SEQ ID NO.: 7) (2.0 and 1.3 nM $K_D$, respectively), which have binding characteristics comparable to those of ch8H9. Similar enhancements were observed in binding to 2Ig-B7H3-Fc (FIG. 12 and Table 12 below).

TABLE 12

Binding kinetics of IgG ch8H9 and hu8H9 H1L2, H3L3, 3.1 and 5.1 to 2Ig-B7H3 determined by surface plasmon resonance

| Construct | $K_{on}(S^{-1} M^{-1})$ | $K_{off}(S^{-1})$ | $K_D$ (nM) |
|---|---|---|---|
| ch8H9 | $4.957 \times 10^4$ | $3.792 \times 10^{-5}$ | 0.76 |
| hu8H9 H1L2 | $1.698 \times 10^4$ | $1.162 \times 10^{-3}$ | 68.4 |
| hu8H9 H3L3 | $4.667 \times 10^6$ | $3.501 \times 10^{-2}$ | 7.5 |

TABLE 12-continued

Binding kinetics of IgG ch8H9 and hu8H9 H1L2, H3L3, 3.1 and 5.1 to 2Ig-B7H3 determined by surface plasmon resonance

| Construct | $K_{on}(S^{-1} M^{-1})$ | $K_{off}(S^{-1})$ | $K_D$ (nM) |
|---|---|---|---|
| hu8H9 3.1 | $3.871 \times 10^4$ | $2.321 \times 10^{-4}$ | 6.0 |
| hu8H9 5.1 | $6.783 \times 10^4$ | $5.588 \times 10^{-5}$ | 0.82 |

Figure 13:
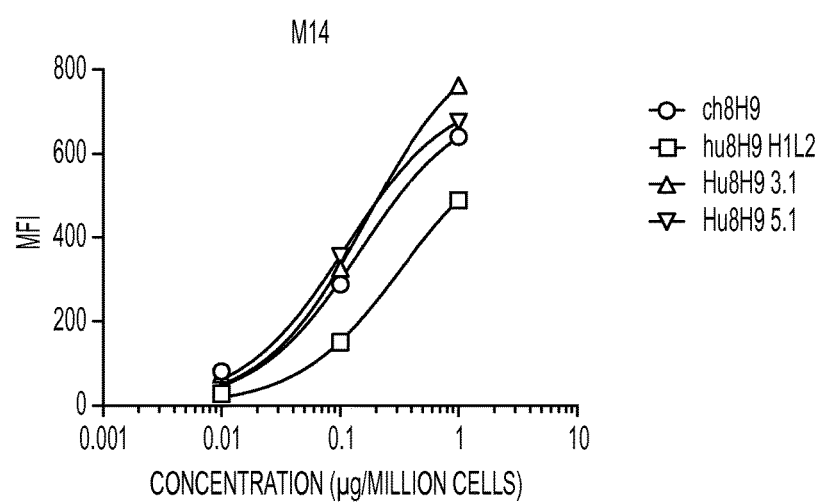
FIG. 13 shows results of experiments in which ch8H9 and hu8H9 IgG variants were bound to M14 neuroblastoma cells. Binding was quantitated by flow cytometry.

Binding of ch8H9 (SEQ ID NO.: 9, SEQ ID NO.: 1) and hu8H9 H1L2 (SEQ ID NO.: 10, SEQ ID NO.: 3), 3.1 (SEQ ID NO.: 13, SEQ ID NO.: 5), and 5.1 (SEQ ID NO.: 15, SEQ ID NO.: 7) to B7H3-positive melanoma M14 tumor cells was tested and the resulting data are presented in FIG. 13. Binding of Hu8H9 3.1 and 5.1 was comparable to the binding of ch8H9, and substantially stronger than that of hu8H9 H1L2.

The binding kinetics for IgG constructs (m8H9, ch8H9, hu8H9 H3L3, and hu8H9 3.1) to both 4Ig-B7-H3 and 2Ig-B7-H3 without Fc fusion were determined (Table 13). Both the m8H9 and ch8H9 antibodies bound to the 2Ig-B7-H3 with higher affinity than 4Ig-B7-H3, indicating that the binding epitope may be more fully exposed in the 2Ig-B7-H3 format. The hu8H9 H3L3 IgG (33 nM $K_D$ for 4Ig-B73H3 and 45 nM $K_D$ for 2Ig-B7-H3) had partial loss of affinity compared to the ch8H9 (7.7 nM $K_D$ for 4Ig-B73H3 and 2.7 nM $K_D$ for 2Ig-B7-H3). The affinity-matured hu8H9 3.1 had a 2.5 to 9-fold enhancement in affinity (13 nM $K_D$ for 4Ig-B73H3 and 5.0 nM $K_D$ for 2Ig-B7-H3) compared to the parental hu8H9 H3L3. Because the hu8H9 3.1 did not have higher affinity that ch8H9, the 6 affinity maturation mutations (LC: S20T, LC: H34Y, HC: A24T, HC: E42G, HC: G56D, HC: A102G) were incorporated into ch8H9 IgG to generate ch8H9 6.1. The binding kinetics of ch8H9 6.1 were 3.7 nM $K_D$ for 4Ig-B73H3 and 0.6 nM $K_D$ for 2Ig-B7-H3, which demonstrated a 2 to 4-fold enhancement in binding relative to ch8H9.

TABLE 13

Binding kinetics for IgG constructs to 4Ig-B7-H3 and 2Ig-B7-H3 without Fc fusion

| | 4Ig-B7-H3 | | | 2Ig-B7-H3 | | |
|---|---|---|---|---|---|---|
| Antibodies | ka (1/Ms) | kd (1/s) | $K_D$ (nM) | ka (1/Ms) | kd (1/s) | $K_D$ (nM) |
| m8H9 | $1.846 \times 10^4$ | $1.650 \times 10^{-4}$ | 8.9 | $2.776 \times 10^4$ | $2.244 \times 10^{-5}$ | 0.81 |
| ch8H9 | $2.834 \times 10^4$ | $2.180 \times 10^{-4}$ | 7.7 | $3.210 \times 10^4$ | $8.729 \times 10^{-5}$ | 2.7 |
| ch8H9 6.1 | $3.349 \times 10^4$ | $1.229 \times 10^{-4}$ | 3.7 | $6.890 \times 10^4$ | $4.254 \times 10^{-5}$ | 0.62 |
| hu8H9 H3L3 | $2.046 \times 10^4$ | $6.770 \times 10^{-4}$ | 33 | $1.347 \times 10^4$ | $6.069 \times 10^{-4}$ | 45 |
| hu8H9 3.1 | $2.342 \times 10^4$ | $2.979 \times 10^{-4}$ | 13 | $3.394 \times 10^4$ | $1.711 \times 10^{-4}$ | 5.0 |

In Vitro Tumor Killing Properties of 8H9 Antibodies

Figure 14:
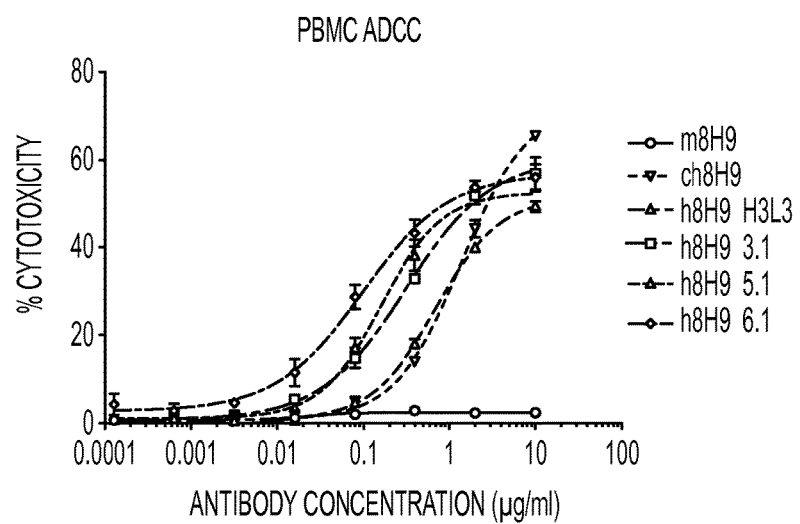
FIG. 14 shows in vitro antibody dependent cell-mediated cytotoxicity (ADCC) of 8H9 antibody constructs against B7-H3(+) neuroblastoma LAN-1 cells, using human PBMC as effector cells. Cytotoxicity was measured by $^{51}$chromium release.

We then tested in vitro tumor killing ADCC properties of five IgG antibody constructs (m8H9, ch8H9, ch8H9 6.1, hu8H9 H3L3, and hu8H9 3.1) using neuroblastoma LAN-1 tumor cells as targets and human PBMC as effector cells. Cytotoxicity was measured by $^{51}$chromium release (FIG. 14 and Table 14). m8H9 had no ADCC function with human PBMC, which is expected for the murine IgG1 isotype. The ch8H9 and hu8H9 H3L3 constructs exhibited potent ADCC (1.4 and 0.7 µg/mL $EC_{50}$, respectively). The ch8H9 6.1 (0.1 µg/mL $EC_{50}$) had a 14-fold improvement in cytotoxicity over ch8H9, and hu8H9 3.1 (0.3 µg/mL $EC_{50}$) had a 2-fold enhancement in killing over hu8H9 H3L3 and a 5-fold enhancement in killing over ch8H9.

TABLE 14

In vitro ADCC assay of anti-B7-H3 IgG constructs

| Antibodies | $EC_{50}$ (µg/ml) | Fold change $EC_{50}$ relative to ch8H9 |
|---|---|---|
| m8H9 | no killing | |
| ch8H9 | 1.40 ± 0.08 | |
| ch8H9 6.1 | 0.10 ± 0.01 | 14-fold |
| hu8H9 H3L3 | 0.70 ± 0.03 | 2-fold |
| hu8H9 3.1 | 0.31 ± 0.03 | 5-fold |
| hu8H9 5.1 | 0.16 ± 0.02 | 9-fold |

In Vivo Targeting of Human Neuroblastoma Xenografts

Figure 15:
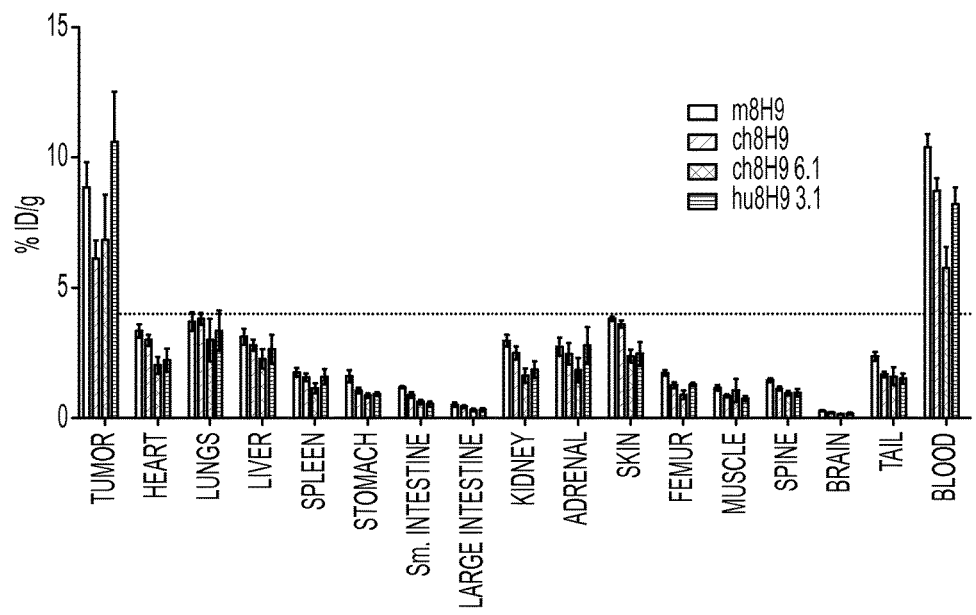
FIG. 15 shows biodistribution of $^{131}$I-labeled 8H9 antibody agents injected into athymic nude mice xenografted with subcutaneous neuroblastoma LAN-1 tumors.

The in vivo biodistribution of 8H9 antibody constructs (hu8H9 3.1 and ch8H9 6.1 compared to m8H9 and ch8H9) was determined using mouse xenografts. Briefly, all antibodies were radiolabeled with $^{131}$I, and their in vitro immunoreactivity against LAN-1 cells was determined (m8H9: 69%, ch8H9:75%, ch8H9 6.1:73%, and hu8H9 3.1:54%). The in vivo biodistributions of each antibody at 48 hours post-injection were analyzed using mice bearing subcutaneous neuroblastoma LAN-1 xenografts (FIG. 15 and Table 15 [Avg: Average]). Tumor uptake as measured by percent injected dose per gram (% ID/gm), was 8.9% for m8H9, 6.1% for ch8H9, 6.8% for ch8H9 6.1 and 10.6% for hu8H9 3.1. Tumor to normal tissue ratios are shown in Table 16 (Avg: Average). All antibodies tested had comparable tumor to non-tumor ratios for most tissues. The highest tumor uptake was observed for hu8H9 3.1, which was statistically higher than ch8H9 (p<0.05) and a higher tumor-to-blood ratio than ch8H9 (1.26 compared to 0.72, p<0.05). A slightly lower tumor uptake was observed for ch8H9 6.1, but comparable tumor-to-blood ratio.

TABLE 15

Biodistribution of $^{131}$I-labelled 8H9 antibodies to LAN-1 xenografts in mice

| | % ID/gm | | | | | | | |
|---|---|---|---|---|---|---|---|---|
| | m8H9 | | ch8H9 | | ch8H9 6.1 | | hu8H9 3.1 | |
| | | | | | N | | | |
| | 5 | | 5 | | 4 | | 4 | |
| Organ | Avg | SEM | Avg | SEM | Avg | SEM | Avg | SEM |
| Tumor | 8.85 | 0.96 | 6.13 | 0.69 | 6.85 | 1.71 | 10.59 | 1.95 |
| Heart | 3.36 | 0.24 | 3.01 | 0.21 | 2.05 | 0.33 | 2.25 | 0.45 |
| Lungs | 3.72 | 0.36 | 3.83 | 0.23 | 3.02 | 0.80 | 3.37 | 0.78 |
| Liver | 3.14 | 0.31 | 2.81 | 0.20 | 2.30 | 0.37 | 2.67 | 0.55 |
| Spleen | 1.78 | 0.17 | 1.60 | 0.15 | 1.18 | 0.18 | 1.61 | 0.30 |

TABLE 15-continued

Biodistribution of $^{131}$I-labelled 8H9
antibodies to LAN-1 xenografts in mice

| | % ID/gm | | | | | | | |
|---|---|---|---|---|---|---|---|---|
| | m8H9 | | ch8H9 | | ch8H9 6.1 N | | hu8H9 3.1 | |
| | 5 | | 5 | | 4 | | 4 | |
| Organ | Avg | SEM | Avg | SEM | Avg | SEM | Avg | SEM |
| Stomach | 1.64 | 0.23 | 1.09 | 0.11 | 0.89 | 0.09 | 0.95 | 0.07 |
| Sm. Intestine | 1.21 | 0.04 | 0.92 | 0.11 | 0.63 | 0.09 | 0.55 | 0.11 |
| Lg. Intestine | 0.52 | 0.08 | 0.45 | 0.05 | 0.32 | 0.05 | 0.33 | 0.06 |
| Kidney | 2.99 | 0.22 | 2.52 | 0.25 | 1.65 | 0.28 | 1.89 | 0.31 |
| Adrenal | 2.76 | 0.36 | 2.49 | 0.41 | 1.86 | 0.46 | 2.82 | 0.68 |
| Skin | 3.83 | 0.08 | 3.62 | 0.14 | 2.39 | 0.24 | 2.50 | 0.45 |
| Femur | 1.76 | 0.10 | 1.28 | 0.11 | 0.90 | 0.18 | 1.32 | 0.06 |
| Muscle | 1.20 | 0.11 | 0.88 | 0.06 | 1.08 | 0.45 | 0.77 | 0.11 |
| Spine | 1.47 | 0.07 | 1.15 | 0.07 | 0.98 | 0.09 | 1.01 | 0.15 |
| Brain | 0.29 | 0.03 | 0.22 | 0.02 | 0.15 | 0.02 | 0.18 | 0.03 |
| Tail | 2.38 | 0.17 | 1.70 | 0.10 | 1.63 | 0.34 | 1.54 | 0.19 |
| Blood | 10.38 | 0.49 | 8.70 | 0.50 | 5.77 | 0.79 | 8.21 | 0.63 |

TABLE 16

Tumor to non-tumor uptake ratios of $^{131}$I-labelled
8H9 antibodies in LAN-1 xenografted mice

| | Tumor to non-tumor ratio | | | | | | | |
|---|---|---|---|---|---|---|---|---|
| | m8H9 | | ch8H9 | | ch8H9 6.1 N | | hu8H9 3.1 | |
| | 5 | | 5 | | 4 | | 4 | |
| Organ | Avg | SEM | Avg | SEM | Avg | SEM | Avg | SEM |
| Tumor | 1.00 | 0.00 | 1.00 | 0.00 | 1.00 | 0.00 | 1.00 | 0.00 |
| Heart | 2.67 | 0.31 | 2.09 | 0.28 | 4.09 | 1.62 | 4.98 | 0.66 |
| Lungs | 2.52 | 0.43 | 1.64 | 0.22 | 2.79 | 0.98 | 3.46 | 0.58 |
| Liver | 2.90 | 0.32 | 2.29 | 0.41 | 3.39 | 1.24 | 4.30 | 0.69 |
| Spleen | 5.18 | 0.74 | 4.03 | 0.67 | 6.96 | 2.75 | 6.67 | 0.54 |
| Stomach | 6.40 | 1.98 | 5.77 | 0.71 | 7.89 | 1.99 | 11.05 | 1.59 |
| Sm. Intestine | 7.29 | 0.63 | 7.11 | 1.05 | 13.03 | 5.04 | 20.50 | 3.13 |
| Lg. Intestine | 22.37 | 8.90 | 14.50 | 2.23 | 22.75 | 6.29 | 32.86 | 3.47 |
| Kidney | 3.02 | 0.38 | 2.64 | 0.54 | 4.53 | 1.49 | 5.64 | 0.47 |
| Adrenal | 3.31 | 0.33 | 2.92 | 0.75 | 3.88 | 0.74 | 3.94 | 0.37 |
| Skin | 2.31 | 0.24 | 1.73 | 0.26 | 2.92 | 0.76 | 4.42 | 0.55 |
| Femur | 5.04 | 0.48 | 5.12 | 1.06 | 7.96 | 1.63 | 7.96 | 1.31 |
| Muscle | 7.46 | 0.58 | 7.00 | 0.72 | 8.27 | 2.93 | 15.17 | 3.74 |
| Spine | 6.04 | 0.61 | 5.49 | 0.82 | 7.01 | 1.67 | 10.54 | 0.87 |
| Brain | 32.65 | 6.03 | 30.60 | 6.62 | 47.54 | 12.77 | 63.35 | 10.18 |
| Tail | 3.80 | 0.49 | 3.67 | 0.47 | 4.74 | 1.35 | 6.77 | 0.59 |
| Blood | 0.85 | 0.06 | 0.72 | 0.10 | 1.32 | 0.46 | 1.26 | 0.16 |

Epitope Determination

Figure 16:
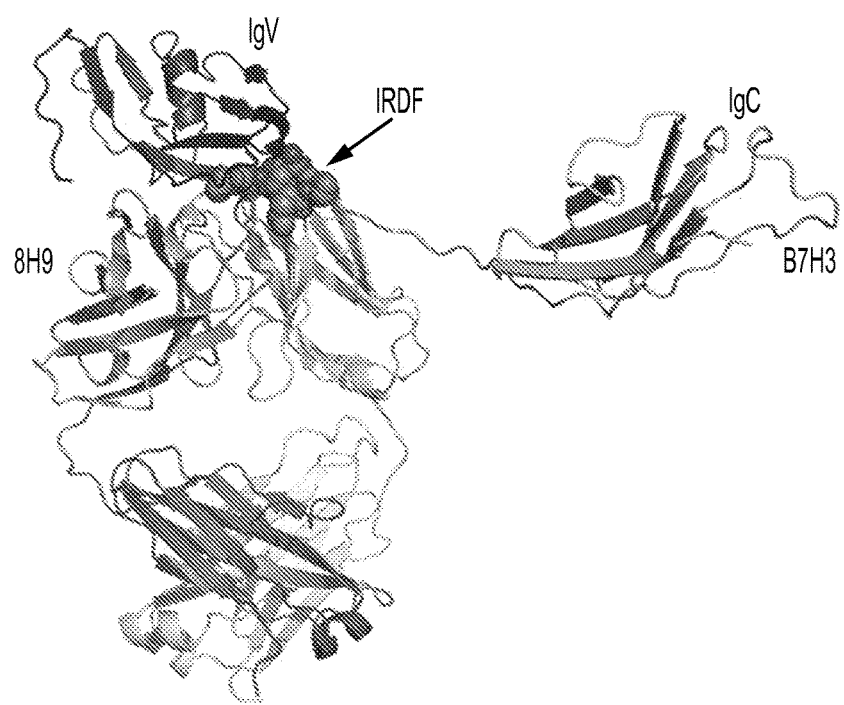
FIG. 16 shows a graphical display of simulated binding between ch8H9 and huB7H3. IRDF (SEQ ID NO.:32) is indicated with an arrow.

Molecular docking technologies were used to predict the precise molecular epitope on B7H3 responsible for the binding of 8H9. Specifically, a homology model of human 2Ig-B7H3 was generated and docking experiments were then performed with the crystal structure of ch8H9 Fab using ZDOCK. FIG. 16 shows the predicted model derived from the docking calculations. The model shows that 8H9 specifically binds the IRDF sequence (residues 126-129, SEQ ID NO:32) of the FG loop in the V-domain of 2Ig-B7H3. In 4Ig-B7H3, this sequence is present twice (residues 126-129 of the V1 domain and residues 344-347 of the V2 domain). The predicted interaction energies for each of the 2Ig-B7H3 interacting residues of the docked complex are shown in Table 17 below. Arg127 and Asp128 have the highest interaction energy (−55.2 and −46.3 kcal/mol respectively).

TABLE 17

Interaction energies calculated from the 8H9:B7H3 docked model

| 2 Ig-B7H3 Residue (SEQ ID NO.: 85) | Interaction Energy (kcal/mol) |
|---|---|
| Phe 123 | −3.59 |
| Val 124 | −11.8 |
| Ser 125 | −14.2 |
| Ile 126 | −10.4 |
| Arg 127 | −55.2 |
| Asp 128 | −46.3 |
| Phe 129 | −1.33 |
| Gly 130 | −3.80 |

Figure 17:
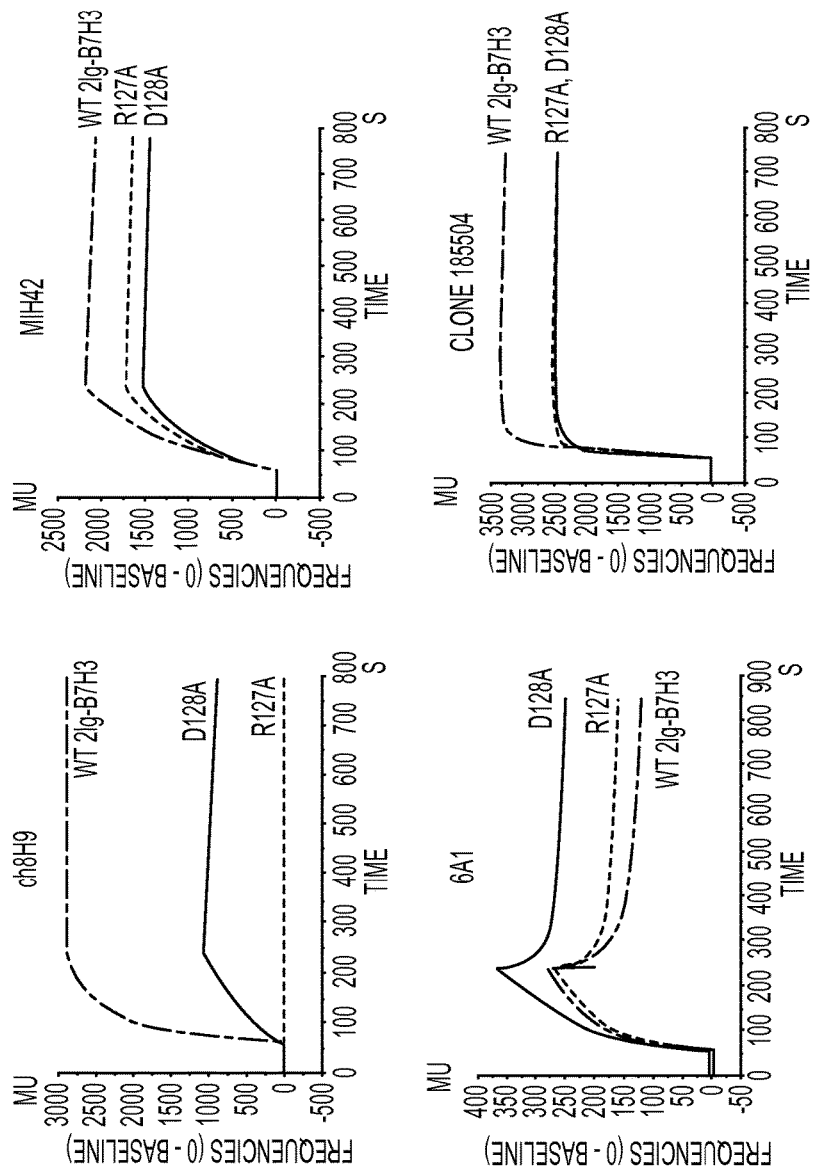
FIG. 17 shows kinetics of binding by IgG anti-B7H3 antibodies ch8H9, MIH42, 6A1 and clone 185504 to wild type 2Ig-B7H3-mFc and 2Ig-B7H3-mFc mutants R127A and D128A, as determined by surface plasmon resonance.
Figure 18:
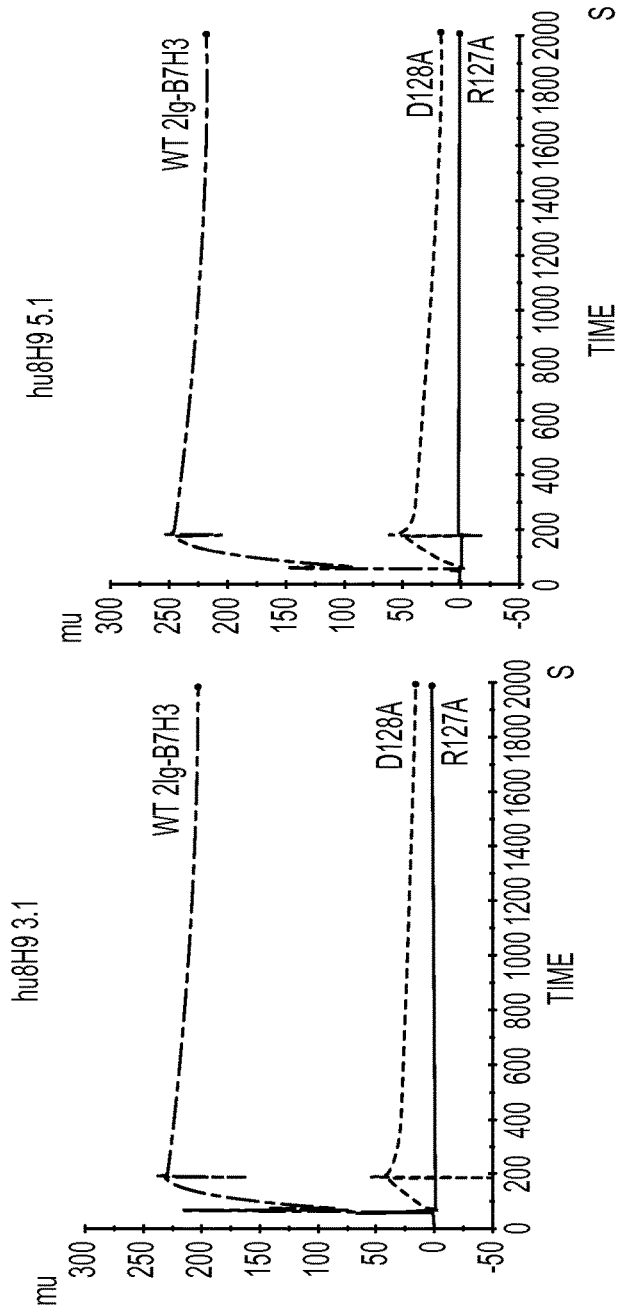
FIG. 18 shows kinetics of binding by IgG anti-B7H3 antibodies hu8H9 3.1 and 5.1 to wild type 2Ig-B7H3-mFc and 2Ig-B7H3-mFc mutants R127A and D128A, as determined by surface plasmon resonance.

Based on the molecular modeling, R127A and D128A point mutations were made in two separate 2Ig-B7H3-mFc constructs and recombinantly expressed. FIG. 17 shows the binding kinetics of ch8H9 (SEQ ID NO.: 9, SEQ ID NO.: 1) to the R127A and D128A mutants of 2Ig-B7H3, along with the binding kinetics of three commercially available anti-B7H3 MAbs (MIH42 and 6A1 from Thermo Scientific Pierce (Rockford, Ill.), and Clone 185504 from R&D Systems (Minneapolis, Minn.)). The maximum RU of binding to WT 2Ig-B7H3-Fc, as well as the relative binding of mutants R127A and D128A are shown in Table 18. ch8H9 shows almost complete loss of binding (99.9%) as to the R127A mutation and partial loss of binding (40%) as to the D128A mutation compared to the wild-type construct. None of the three other anti-B7H3 antibodies showed substantial loss in binding to either mutant B7H3 protein (i.e., antibodies MIH42 and clone 185504 retained ~70-75% of their respective binding to both R127A and D128A mutants; antibody 6A1 had weak overall binding to the WT 2Ig-B7H3, and either the same binding to R127A or elevated binding to the D128A mutants). Similar to ch8H9 (SEQ ID NO.: 9, SEQ ID NO.: 1), the hu8H9 3.1 (SEQ ID NO.: 13, SEQ ID NO.: 5) and 5.1 (SEQ ID NO.: 15, SEQ ID NO.: 7) variants also showed a total and a partial loss of binding (FIG. 18). These binding studies demonstrated that ch8H9 was uniquely specific to the IRDF sequence of B7H3. Lost binding to R127A and D128A B7-H3 mutants by SPR for humanized 8H9 constructs was also confirmed.

TABLE 18

Response Units of binding to WT B7-H3 and mutants D128A and R129

| | Max RU | Relative binding | |
|---|---|---|---|
| Antibody | WT-2Ig-B7-H3 | R127A | D128A |
| ch8H9 | 2875 | 0.1% | 60.0% |
| MIH42 | 2526 | 76.1% | 68.8% |
| 6A1 | 196.1 | 109.1% | 167.5% |
| clone 185504 | 3344 | 75.5% | 74.9% |

Use of MAb 8H9 for Immune Modulation

It has previously been shown that the FG loop of the IgV domain of B7H3 plays a critical role in the proteins' T-cell inhibitory function in mouse. Mouse B7H3 only exists in the 2Ig-B7H3 form, in which the critical sequence responsible for the inhibitory function is IQDF (residues 126-129, SEQ ID NO.:86). We have demonstrated that m8H9 and clones 3.1 and 5.1 all bind to the homologous IRDF sequence (residues 126-129) in human B7H3 (SEQ ID NO.: 32), and specifically to Arg127. Additionally, m8H9 and its humanized forms do not bind to the murine B7H3, which contains Gln127. Unlike other anti-B7H3 antibodies tested, only 8H9 can be used to bind the FG-loop of B7H3, which can be used to block the immune-inhibitory function of B7H3.

Figure 19:
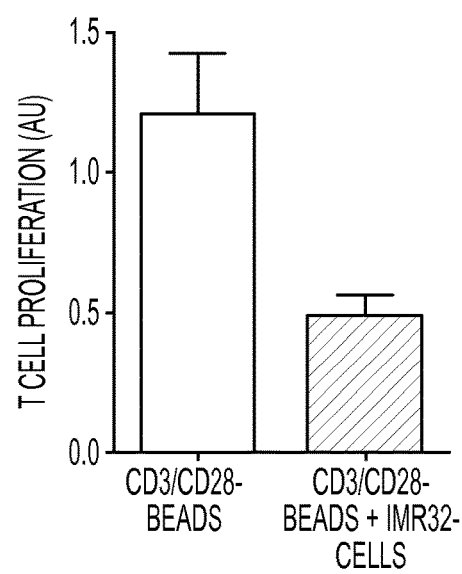
FIG. 19 shows results of experiments in which T cell proliferation was measured in the presence of CD3/CD8 activating beads and in the presence or absence of B7H3-positive neuroblastoma IMR-32 cells.
Figure 20:
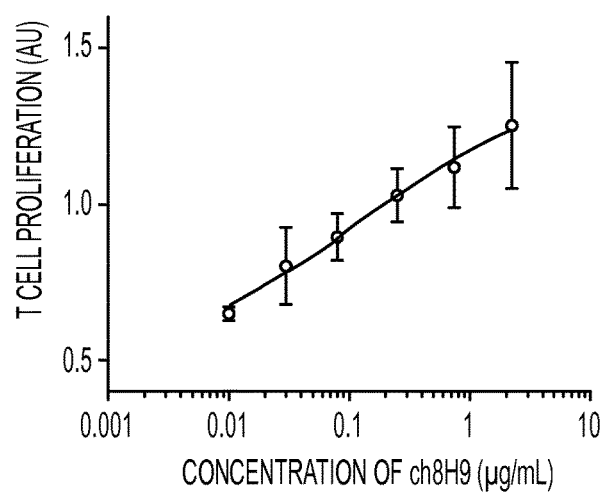
FIG. 20 shows results of experiments in which T cell proliferation was measured in the presence of CD3/CD8 activating beads and B7H3-positive neuroblastoma IMR-32 cells, and increasing concentrations of ch8H9.

FIG. 19 presents data showing that B7H3-positive neuroblastoma IMR-32 cells can inhibit T cell proliferation. In this assay, a 60% reduction in the proliferation of T cells was observed when IMR-32 cells were present. Chimeric 8H9 suppresses this inhibitory effect on T cell proliferation in a dose-dependent manner and even enhances T-cell proliferation in the presence of tumor cells (FIG. 20).

Figure 21:
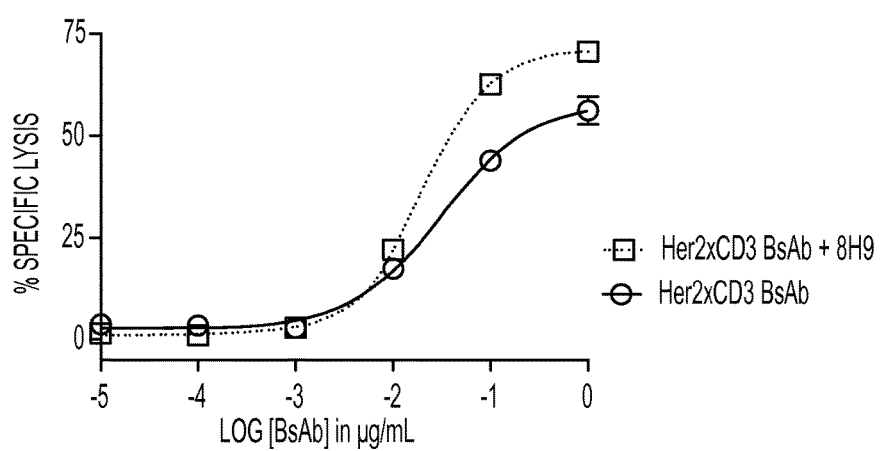
FIG. 21 shows results of experiments in which T cell mediated cytotoxicity regarding human cervical carcinoma cells (HeLa) was measured. Carcinoma cells had been pre-treated with a Her2×CD3 bispecific antibody alone, or with this antibody and additionally m8H9 IgG.

It was also tested whether m8H9 can overcome the inhibitory effect of B7H3 on T-cell function. Using an anti-Her2× anti-CD3 bispecific antibody (trastuzumab fused to huOKT3 scFv), it was tested whether m8H9 could enhance T-cell mediated cytotoxicity of the Her2-positive, B7H3-positive human cervical carcinoma cells (HeLa) (FIG. 21). It was observed that when tumor cells are pre-incubated with 8H9, maximal killing is enhanced from 58% (no pre-treatment) to 71% (with 8H9 pre-treatment).

These sets of experiments are the first demonstration that m8H9 and its derivatives can be used for immune-modulation therapy.

Methods

Homology Modeling

Homology models of the variable region of 8H9 were generated using the ROSETTA antibody modeling server and Discovery Studio 3.0 (Accerlys, San Diego, Calif.).

X-Ray Crystallography

Fab fragments of ch8H9 were generated by papain digestion using a standard Fab preparation kit (Pierce Biotechnology, Rockford, Ill.). The purified Fab fragment was concentrated to 10 mg/ml in 20 mM HEPES, pH 6.5, and then crystallized in a hanging drop by vapor diffusion at 16° C. against a reservoir of Hampton Index reagent containing 0.2 M Lithium sulfate monohydrate, 0.1 M BIS-TRIS pH 6.5, and 25% w/v polyethylene glycol 3,350 (Hampton Research, Aliso Viejo, Calif.). The droplet was formed by mixing 1 µl of protein solution and 1 µl of reservoir solution. Data were collected at the Argonne Advanced Photon Source beamline 24IDE. The Fab structure was solved by molecular replacement using MolRep (CCP4 suite) (Mccoy, A. J., et al., 2007, J. Appl. Crystallogr. 40:658-674). The best molecular replacement model was refined using Phenix (Adams, P. D. et al., 2010, Acta crystallographica Section D Biological crystallography 66:213-221), and manual fitting was performed with O (Bailey, S., 1994, Acta Crystallogr. D 50:760-763). The crystals structure was resolved at 2.5 Å.

Molecular Simulations of ch8H9 Structure

The crystal structure of ch8H9 was simulated using CHARMm (CHemistry at Harvard Molecular mechanics) force fields and the effect of each point mutation calculated from the difference between the folding free energy of the mutated and the wild type protein. Generalized Born approximation was used to account for the effect of the solvent and all electrostatic terms were calculated as a sum of coulombic interactions and polar contributions to the solvation energy. A weighted sum of the van der Waals, electrostatic, entropy and non-polar terms was calculated for each point mutation. All calculations were performed using Discovery Studio 3.0 (Accelrys, San Diego, Calif.). Forward and backward mutations were being tested for their effect on the stability of the next generation hu8H9. Docking simulations were generated using ZDOCK software (available through Boston University, Boston, Mass.). Docking simulations were generated using ZDOCK (Chen, R. et al. 2003, Proteins 52:80-87) and homology modeling of B7H3 was done using MODELLER (Sanchez, R., and Sali, A., 1997, Proteins Suppl. 1:50-58). Electrostatic surface potentials were generated using DelPhi (Rocchia, W. et al., 2002, J. Comput. Chem. 23:128-137).

Biotinylation of B7H3 Antigen

The gene for the human B7H3-mouse-Fc (mFc) fusion protein was optimized for expression in CHO cells (Genscript, Piscataway, N.J.). Using the pBluescript vector (Agilent Technologies, Inc., Santa Clara, Calif.), the gene were transfected into DG44 CHO cells and expressed as previously described (Cheung et al., 2012 OncoImmunology 1:477-486). Biotinylation of the B7H3-mFc fusion protein was performed using EZ-Link Sulfo-NHS-Biotin and a Biotinylation Kit (Thermo Scientific, Tewksbury, Mass.) according to the manufacturer's instructions. The biotinylated protein was subsequently concentrated using a 50,000 MWCO Vivaspin centrifuge tube (Sartorius Stedim, Goettingen, Germany) and tested for its biotinylation in a streptavidin binding ELISA.

Mutagenesis by Error-Prone PCR

Error-prone PCR of the entire hu8H9 scFv (V3) gene was performed using Stratagene GeneMorph® II Random Mutagenesis Kit according to the instructions of the manufacturer. Briefly, PCR was conducted in a 50-µL reaction containing 1× Mutazyme II reaction buffer, 0.5 µM each of primers ERRORF (5' TCAGTTTTGGCCCAGGCGGCC 3'; SEQ ID NO.: 81) and ERRORR (5' ACCACTAGTTGGGC-CGGCCTG 3'; SEQ ID NO.: 82), 0.2 mM (each) dNTPs, 1 ng of DNA template, 2 µM 8-oxo-deoxyguanosine triphosphate, 2 µM 2'-deoxy-p-nucleoside-5'-triphosphate, and 2.5 U of Mutazyme II DNA polymerase. The reaction mixtures were denatured at 95° C. for 2 min, cycled 35 times at 95° C. for 1 min, 60° C. for 1 min, and 72° C. for 1 min, and finally extended at 72° C. for 10 min. The PCR products were purified by 1% agarose gel electrophoresis and each amplified in four 100-µL PCR reactions containing 1×NEB PCR reaction mix, 1 µM of primers YDRDF (5'CTTCGCT-GTT TTTCAATATT TTCTGTTATT GCTTCAGTTT TGGCCCAGGC GGCC 3'; SEQ ID NO.: 83) and YDRDR (5'GAGCCGCCAC CCTCAGAACC GCCACCCTCA GAGCCACCAC TAGTTGGGCC GGCCTG 3'; SEQ ID NO.: 84), 120 ng of error-prone PCR product, and 2.5 U of DNA polymerase. The reactions were thermally cycled using 30 cycles and as otherwise described above. Reaction products were purified by 1% agarose gel electrophoresis and concentrated by ultrafiltration with water.

Selection of hu8H9 Mutants from the Yeast Libraries

The construction and growth of yeast libraries for affinity maturation were modified from the protocol previously published (Zhao et al. 2011 Mol Cancer Ther 10:1677-1685). Before fluorescent cell sorting (FACS), the yeast library (1×10$^9$ cells) was pre-incubated with mouse 3F8 IgG at RT for 1 h, sequentially panned against 10 µg of B7H3-mFc-conjugated magnetic beads for 1 h at RT in PBSA buffer (0.1% BSA in PBS), followed by the separation with a magnetic stand. The isolated beads were washed for 3 times with PBSA buffer, resuspended in 10 ml of SDCAA media and grown overnight in a 30° C. shaker at 250 rpm. The yeast cells recovered from magnetic beads were incubated in SG/RCAA media for 18 h at 20° C. with 250 rpm shaking. For the first FACS selection, approximately 1×10$^8$ yeast cells were pelleted, washed twice with PBSA buffer and resuspended in 1 ml PBSA buffer containing 10 µg/ml biotinylated B7H3-mFc and a mouse anti-c-myc antibody (Jackson Research Laboratories, Bar Harbor, Me.). After incubation, yeast cells were washed 3 times and then resuspended in 1 ml PBSA buffer. Both a 1:100 dilution of R-phycoerythrin conjugated Streptavidin (BD Bioscience)

and FITC conjugated goat anti-mouse (Fab)$_2$ (Invitrogen, Carlsbad, Calif.) were added to the yeast cells to be sorted, after which the cells were incubated at 4° C. for 30 min, washed 3 times with PBSA buffer, and then resuspended in PBSA buffer for sorting. Sorting gates were determined to select for higher antigen binding signals. Collected cells were grown overnight in SDCAA media at 30° C. and then incubated in SG/RCAA for the next round of sorting. For the next two selections, approximately 1-2×10$^7$ yeast cells were used for staining with 3 µg/ml and 1 µg/ml biotinylated B7H3, respectively. Yeast plasmids were isolated using Zymoprep yeast Plasmid Mimiprep II Kit (Zymo Research, Irvine, Calif.) according to the manufacturer's instructions and used as templates for the second library construction. Construction and selection of the second library was done as with respect to the first yeast library. However, the second yeast library was subjected to four FACS selections with 1, 0.2, 0.05 and 0.01 µg/ml of biotinylated B7H3-mFc, respectively. Cells from the last selection were spread on SDCAA plates. Monoclonal yeast cells were characterized and isolated plasmids encoding scFvs with improved affinity were sequenced.

Expression and Purification of Soluble scFv

ScFvs were expressed and purified as previously described (Zhao et al., 2011, Mol. Cancer Ther. 10:1677-1685). HB2151 bacterial cells were transformed with pComb3× plasmid containing scFv sequences. Single fresh colonies were inoculated into 2YT medium containing 100 µg/ml ampicillin and 0.2% glucose. The culture was induced by isopropyl-L-thio-h-D-galactopyranoside (final concentration 0.5 mM). After overnight growth at 30° C., the bacteria were centrifuged at 5,000×g for 15 min. Soluble scFv was released from the bacterial periplasm by incubating bacteria at 30° C. for 30 minutes. The clear supernatant was recovered and purified on a Ni-NTA column. All recombinant scFvs had FLAG and His tags.

Expression and Purification of IgG Constructs

Gene constructs (based on the pBluescript vector (Agilent Technologies, Inc., Santa Clara, Calif.)) encoding the heavy and light chain of 8H9 were transfected into CHO-S cells and selected with G418 (Invitrogen, Carlsbad, Calif.). Antibody producer lines were cultured in OptiCHO serum free medium (Invitrogen, Carlsbad, Calif.) and the supernatant was then harvested. A protein A-affinity column was pre-equilibrated with 25 mM sodium citrate buffer/0.15 M NaCl at pH 8.2. Bound 8H9 was eluted with 0.1 M citric acid/sodium citrate buffer, pH 3.9 and dialyzed in 25 mM sodium citrate and 150 mM NaCl at pH 8.2.

ELISA

B7H3-mFc (100 ng/well) or 2IgB7H3 (R&D, Minneapolis, Minn.) (25 ng/well) were coated on polyvinyl microtiter plates in PBS overnight. Plates were then blocked with 0.5% BSA in PBS at 150 µl per well for 1 h at room temperature. Antibodies were added in triplicates with serial dilution in 0.5% BSA. Following incubation for 1 h at room temperature and washing with PBS, HRP-mouse anti-human Fc antibody, HRP-streptavidin, or HRP-mouse anti-Flag antibody was added. After incubation for 1 h at room temperature and further washing, the color was developed and quantified using an ELISA plate reader at 490 nm.

Flow Cytometric Analysis

For the staining of yeast cells displaying scFv on their surface, cells were incubated with B7H3-mFc antigen at different concentrations (0.1 and 1 µg/ml) in PBSA for 30 min on ice, followed by incubation with an APC-conjugated anti-mouse antibody (BD Bioscience, San Jose, Calif.) as the secondary antibody. For the staining of tumor cells, cells were harvested in culture medium and incubated with 1 µg/ml purified scFvs, followed by sequential incubation with a mouse anti-his antibody and a PE-anti-mouse antibody. Flow cytometry was performed using FACScalibur™ (BD Bioscience, San Jose, Calif.).

Affinity Determination by Surface Plasmon Resonance

In brief, B7H3 antigen (either 2Ig-B7H3, 4Ig-B7H3, 2Ig-B7H3-mFc, 4Ig-B7H3-mFc), was directly immobilized onto the CM5 sensor chip via hydrophobic interaction. Reference surface was set up for nonspecific binding and refractive index changes. For analysis of the kinetics of interactions, varying concentrations of scFvs were injected at flow rate of 30 µl/min using running buffer containing 10 mM HEPES, 150 mM NaCl, 3 mM EDTA, and 0.05% Surfactant P-20 (pH 7.4). The association and dissociation phase data were fitted simultaneously to a 1:1 model by using BIAevaluation 3.2. All the experiments were done at 25° C. For epitope determination, WT 2Ig-B7H3, R127A and D128A was immobilized onto the chip, 400 nM of ch8H9, MIH42, 6A1 and clone 185504 were injected as described above (contact time 180 s, dissociate time 600 s).

T Cell Proliferation Assay

T cells were purified from human peripheral blood mononuclear cells (PBMCs) using a Pan T cell isolation kit (Miltenyi Biotec, Cambridge, Mass.). Neuroblastoma IMR-32 cells were irradiated at 80 Gy and resuspended in RPMI (GIBCO) at 0.1 million/ml. 1×10$^4$ IMR-32 cells/well (100 µl) with different concentrations of ch8H9 (50 µl) were added to a 96 well cell culture plate and incubated for 2 hr at room temperature. Subsequently, 2×10$^5$/well-purified T cells were mixed with 1.5 µl CD3/CD28 dynabeads (Invitrogen, Carlsbad, Calif.) were added to the wells with the IMR-32 cells. The cells were cultured and maintained in RPMI supplemented with FBS and 30 U/ml IL-2 at 37° C. for 6 days. T cell proliferation was quantitated using the Cell counting Kit-8 (CCK-8) assay (Dojindo Mol, Rockville, Md.) according to the manufacturer's protocol.

T Cell Mediated Cytotoxicity Assay

The HER2(+) and B7H3(+) human cervical carcinoma cells (HeLa) were cultured at 37° C. with RPMI+10% FBS, 2% L-Glutamine, and 1% P/S. Cells were harvested with Trypsin/EDTA and 1×10$^6$ cells were incubated with 100 mCi of $^{51}$Cr for 60 min at 37° C. and with or without 100 mg/mL of the B7H3 specific mouse antibody 8H9. After incubation, cells were washed twice and 5,000 target cells were plated in each well of a 96-well round bottom plate together with T-cells at a ratio of 1:10, respectively. Different concentrations (from 1 to 1×10$^{-6}$ 1 mg/mL) of an anti-HER2× anti-CD3 bispecific antibody (trastuzumab fused to huOKT3 scFv) and 10 mg/mL of murine 8H9 antibody were then added (the latter only to cells preincubated with the 8H9 antibody). Supernatants were harvested after a fours of hour incubation and their radioactivity measured in a scintillation counter. Specific lysis of tumor cells was calculated based on the following formula: % specific lysis=(sample cpm−spontaneous cpm)/(maximal cpm−spontaneous cpm)×100%.

Tumor Cell Culture and Antibody-Dependent Cell-Mediated Cytotoxicity (ADCC) Assay Neuroblastoma LAN-1 tumor cells were obtained from Children's Hospital of Los Angeles. Cells were cultured in RPMI1640 (Cellgro, Manassas, Va.) supplemented with 10% of fetal bovine serum (FBS, Life Technologies, Grand Island, N.Y.) at 37° C. in a 5% $CO_2$-humidified incubator. ADCC assays were performed as previously described (Cheung, N. K. et al., 2012, Oncoimmunology 1:477-48652). Briefly, LAN-1 neuroblastoma tumor cells were radiolabeled with $^{51}$Cr, and peripheral blood mononuclear cells (PBMC) were used as effectors at a 25:1 effector-to-target ratio. The cytotoxicity was measured by $^{51}$Cr release.

Biodistribution of Antibody in Xenografted Mice

Female athymic nude mice (6-8 week old) were purchased from Harlan Sprague Dawley, Inc. All procedures were carried out in accordance with the protocols approved by Memorial Sloan-Kettering Cancer Center Institutional Animal Care and Use Committee and institutional guidelines for the proper and humane use of animals in research. Tumor cells (LAN-1) were harvested, and subcutaneously (s.c.) implanted to the flank of mice ($5 \times 10^6$ cells per each mouse). When the tumor volumes were approximately 200 mm$^3$, randomized groups of mice (n=4-5/group, one radiolabeled antibody preparation/group) were intravenously injected with 50 µCi of $^{131}$I radioiodinated antibody (prepared according to the IODO-GEN method (Salacinski, P. R. et al., 1981, Analytical biochemistry 117:136-146; Harlow, E. and D. Lane, 1999, Using antibodies: a laboratory manual, Cold Spring Harbor Laboratory Press, Cold Spring Harbor, N.Y.) followed with gel-filtration purification using commercial pre-packed Sephadex G-25 columns into PBS+ 1% BSA; specific activity: 1.67-3.81 mCi/mg; 13-30 µg of antibody/dose). The immunoreactivity of each tracer was evaluated using an in vitro cell-binding assay with freshly harvested LAN-1. Mice were scarified in 48 hours post-injection (p.i.), organs were removed and counted in a gamma counter (Perkin Elmer Wallac Wizard 3). These organs included skin, liver, spleen, kidney, adrenal, stomach, small intestine, large intestine, femur, muscle, tumor, heart, lung, spine, and brain. Count rates were background and decay corrected, converted to activities using a system calibration factor specific for the isotope, normalized to the administered activity, and expressed as percent injected dose per gram (% ID/g). Tumor to non-tumor ratios of % ID/gm were also calculated.

Clinical Use of 8H9 in Compartmental Radioimmunotherapy

Metastasis to the Central Nervous System (CNS)

Brain metastasis is a devastating complication and a major hurdle to cancer cure for most solid tumors; its biology is poorly understood, management inadequate, and cure is rare (Maher E. A. et al., Cancer Res 69:6015-20, 2009). Tumor cells from blood or from brain metastases can invade the CSF and disseminate throughout the neuroaxis by the constant flow of CSF from the ventricles to the spinal canal and over the cortical convexities, a condition called leptomeningeal (LM) carcinomatosis (Grossman, S. A. et al., 1999, Oncology 13:144-152; Bruno, M. K. et al., 2005, Cancer Treat. Res. 125:31-52; Gleissner, B. et al., 2006, Lancet Neurol. 5:443-52).

LM carcinomatosis is most common in patients with disseminated systemic metastasis (Wasserstrom, W. R. et al., 1982, Cancer 49:759-72; Balm, M. et al., 1996, Arch. Neurol. 53:626-32; Chamberlain, M. C. et al., 2005, J. Clin. Oncol. 23:3605-13). Concurrent parenchymal brain metastases are not uncommon (11%-31% of patients) (Wasserstrom, W. R. et al., 1982, Cancer 49:759-72; Freilich, R. J. et al., 1995, Annals of Neurology 38:51-57; Posner, J. B., Neurologic Complications of Cancer, Comtemporary Neurology Series, Philadelphia, F. A. Davis Company, 1995). In contrast to leukemia, where LM metastasis is well controlled by intrathecal chemotherapy (Littman, P. et al., 1987, Int. J. Radiat. Oncol. Biol. Phys. 13:1443-9), the prognosis with respect to solid tumors is extremely guarded despite the use of chemotherapy and radiation therapy (Wasserstrom, W. R. et al., 1982, Cancer 49:759-72; Grossman, S. A. et al., 1991, Neurol. Clin. 9:843-56).

Malignant Ascites

Malignant ascites (peritoneal carcinomatosis) accompanies a wide spectrum of abdominal and extra-abdominal tumors. Lymphatic obstruction and vascular permeability are major factors in its pathogenesis (Holm-Nielsen, P., 1953, Acta Pathol. Microbiol. Scand. 33:10-21; Sangisetty, S. L. et al., 2012, World J. Gastrointest. Surg. 4:87-95). Malignant ascites reduces patients' quality of life significantly because it results in protein loss, electrolyte imbalance, diffuse edema and abdominal sepsis. Among abdominal tumors, ovarian, endometrial, colorectal, gastric, pancreatic and peritoneal malignancy are associated with malignant ascites. In some studies, up to 15% of all patients with gastrointestinal cancers develop malignant ascites at some stage of their disease (Smith, E. M. et al., 2003, Clin. Oncol. (R. Coll. Radiol.) 15:59-72; Koppe, M. J. et al., 2006, Ann. Surg. 243:212-22). While epithelial ovarian cancer accounts for 25% (22,240 new cases, 14,030 deaths per year in the US) of all female genital tract cancers, two-thirds of these patients develop malignant ascites (Eskander, R. N. et al., 2012, Int. J. Womens Health 4:395-404).

Also extra-abdominal tumors, e.g., breast cancer, lung cancers and lymphoma, are known to cause malignant ascites. In up to 20% of all patients with malignant ascites, the primary tumor site is unknown (Saif, M. W. et al., 2009, Ann. Saudi Med. 29:369-77).

According to the multicenter Evolution of Peritoneal Carcinomatosis (EVOCAPE) study, malignant ascites is an adverse prognostic factor resulting in a median survival of a few month (Sadeghi, B. et al, 2000, Cancer 88:358-63). Curative therapies do not exist, while palliative treatments are inadequate, often leading to a painful death (Sangisetty, S. L. et al., 2012, World J. Gastrointest. Surg. 4:87-95; Sugarbaker, P. H. et al., 2006, Ann. Surg. Oncol. 13:635-44).

Previous Experience with Compartmental Radioimmunotherapy (cRIT)

One approach to malignant ascites and LM carcinomatosis is compartmental radioimmunotherapy (cRIT), where radiolabeled antibodies are injected directly into the compartment (peritoneal cavity or CSF space) to target radiation to tumors. Intraperitoneal administration of antibody $^{90}$Y-CC49 (mouse anti-TAG-72, ≤24 mCi/m$^2$) (Alvarez, R. D. et al., 2002, Clin. Cancer Res. 8:2806-11) and antibody $^{90}$Y-HMFG1 (mouse anti-MUC1, 666 MBq/m$^2$) (Verheijen, R. H. et al., 2006, J. Clin. Oncol. 24:571-8) was tolerated by patients with recurrent ovarian cancer, although the study showed no evidence of survival gain. Intrathecal and intraventricular administration for treatment of LM carcinomatosis and intra-tumoral therapy of malignant brain tumors using antibody $^{131}$I-81C6 (anti-tenascin MAb) prolonged patient survival (Reardon et al., 2006, J. Clin. Oncol. 24:115-22; Reardon, D. A. et al., 2008, Neuro. Oncol. 10:182-9). The use of antibody At-81C6 is one example of α-particle therapy for minimal residual disease in malignant glioma (Zalutsky, M. R. et al., 2008, J. Nucl. Med. 49:30-8).

The CSF Compartment is Ideally Suited for cRIT to Achieve Highly Favorable Therapeutic Index The CSF (thecal sac) space has unique characteristics suitable for cRIT: (1) the blood brain barrier (BBB) prevents MAb recirculation; (2) compared to blood, CSF has few white cells and therefore no FcR(N) and ~1000-fold less IgG (Dayson, H., Segal M. B.: Physiology of the CSF and blood-brain barriers. Boca Raton, Fla., CRC Press, 1996, pp 489-523). (3) MAb injected into the CSF compartment is better shielded from host immunity, with less sequestration by Fc receptors or degradation by enzymes; (4) the 200-fold lower protein content of CSF (versus serum) facilitates MAb binding to its intended target; (5) since CSF volume is small (140 ml), MAb achieves a very high compartmental concentration; (6) the CSF compartment is renewed every 7-8 hours, providing a built-in washing step; (7) CSF flow can be reduced pharmacologically, permitting longer MAb reaction time; (8) the apparent absence of an anatomic barrier facilitates the movement of MAb between CSF and the extracellular space of the brain (Dayson H, Segal M. B.: Physiology of the CSF and blood-brain barriers. Boca Raton, Fla., CRC Press, 1996, pp 489-523; Spector, R., Mock D. M., 1988, Neurochem. Res. 13:213-9) especially if there is damage to the meninges either by tumor or by surgery.

Neuroblastoma Metastasis to the CNS

Neuroblastoma metastasis to the CNS was once considered rare. In a retrospective analysis of 61 patients with neuroblastoma metastatic to the CNS at Memorial Sloan Kettering Cancer Center over the last decade, 34 patients with CNS NB (with no evidence of bony disease in the skull) had MYCN amplified disease, while 9 had a lumbar puncture at initial diagnosis, both being known risk factors (Kramer, K. et al., 2001, Cancer 91:1510-9). Two patients had CNS disease at initial NB presentation, both with headaches and high intracranial pressure requiring shunts. 57 patients had CNS NB at 5-61 months (median 21.7) from diagnosis, median 18.5 months in the MYCN amplified cohort. Forty patients (68%) had isolated CNS relapse including 26 (44%) with a single parenchymal focus. Leptomeningeal spread occurred in 19 (32%) patients, the remainder having multifocal disease. As the natural history of NB changed, isolated CNS relapse has made cure elusive, now afflicting >20% of patients at MSKCC whose systemic disease has been "eradicated" (Cheung, N. K. et al., 2012, J. Clin. Oncol. 30:3264-70). Conventional treatment modalities, including surgical resection, chemotherapy and radiation, have not improved patient outcome (Caussa, L. et al., 2010, Int. J. Radiat. Oncol. Biol. Phys. 79(1):214-9; Croog, V. J. et al., 2010, Int. J. Radiat. Oncol. Biol. Phys. 78(3): 849-54).

cRIT of Metastatic Cancer to the Central Nervous System in a Phase I/II Study Using Intra-Ommaya $^{131}$I-8H9

The first in human use of intrathecal $^{131}$I-monoclonal antibody was successfully tested in a phase I clinical trial with favorable toxicity profile and patient outcome (Kramer, K. et al., 2007, J. Clin. Oncol. 25:5465-70). Using this platform, $^{131}$I-8H9 was tested in a phase I/II study. Patients were studied with SPECT (Single Photon Emission Computed Tomography) after receiving 2 mCi of $^{131}$I-8H9, or PET (Positron emission tomography) after receiving $^{124}$I-8H9 injected through an Ommaya reservoir. Serial CSF and blood samples were taken over 48 hours for dosimetry calculations. SPECT or PET scans were obtained at approximately 4, 24, and 48 hours. MR brain and spine as well as CSF cytology were obtained prior to and 4 weeks after injection. A second injection of $^{131}$I-8H9 was given unless patients developed progressive disease. Acute side effects included grade 1 or 2 fever, headache or vomiting, and occasional transient grade 3 ALT elevation. Calculated mean radiation dose to the CSF was 36.3 (range 12.8-106) cGy/mCi; mean blood dose was 2.5 cGy/mCi. $^{124}$I-8H9/PET provided high resolution images of drug distribution within the CSF space, and correlated well with the predicted dose delivered by $^{131}$I-8H9 therapy. Radiographic response of LM disease was seen; acute side effects were limited. Intra-Ommaya $^{131}$I-8H9 appears relatively safe, has a favorable therapeutic ratio, and other than medullary toxicity, the MTD has not yet been reached (80 mCi per dose).

Prolonged Survival for Patients with CNS Neuroblastoma (Kramer K et al., J Neurooncol 97:409-18, 2010; Kramer K et al., Advances in Neuroblastoma Research A-0241, 2014)

Patients at Memorial Sloan Kettering Cancer Center underwent a temozolamide/irinotecan based CNS salvage regimen incorporating cRIT using $^{131}$I-8H9 (n=37) and $^{131}$I-3F8 (n=5), plus systemic immunotherapy using 3F8+ GMCSF (Granulocyte macrophage colony-stimulating factor) (Gp1). Non-regimen treatments used other therapies +/− cRIT (Gp2, all $^{131}$I-8H9). Disease evaluation included serial MR brain/spine, MIBG, CT, and bone marrows. Of 83 patients with CNS NB, cRIT was possible in 56 (67%), 42 (51%) following salvage regimen (Gp1), 33% presenting with multiple parenchymal masses +/− leptomeningeal disease. In Gp1, 26/42 (62%) patients are alive and well, mean overall survival (OS) 82.6 months, including 5/14 (35%) with leptomeningeal disease or multiple parenchymal masses; 3/42 (7%) deaths were due to non-NB complications. OS for Gp2 patients was 15% (mean 21 months). The only long-term survivors among Gp2 patients included 7 who receive cRIT (mean OS 42.8 moths). Overall, 47 patients (56%) died of NB involving the CNS only (n=12, 25%), systemic only (n=14, 30%), CNS and systemic (n=16, 34%) or toxicity (n=5, 11%). Treatment related toxicity included CNS hemorrhage (1) and pulmonary insufficiency during chemotherapy (1). Deaths in long-term survivors included infection (1), pulmonary fibrosis (1), and AML (1). Radionecrosis was rare. (Kramer, K. et al., 2014, Advances in Neuroblastoma Research A-0246). This is a significant improvement in survival for patients treated with cRIT at their first relapse in the CNS. The cRIT regimen was well tolerated by young patients, despite their prior history of intensive cytotoxic therapies. It has the potential to increase survival with better than expected quality of life.

Intraperitoneal (IP) cRIT with $^{131}$I-8H9 (Modak, M. J. et al., ASCO Annual Meeting, J Clin Oncol 2013)

A phase I study of intraperitoneal (IP) cRIT with $^{131}$I-8H9 for patients with desmoplastic small round cell tumors (DSRCT) and other solid tumors involving the peritoneum is near complete in children and young adults (clinicaltrials.gov NCT01099644). DSRCT, a rare sarcoma of adolescents and young adults usually arising from the peritoneum, is lethal in >80% of patients despite aggressive multimodality therapy. Recurrences often present as multifocal peritoneal implants, making it uniquely suited for IP targeting. IP cRIT, by virtue of prolonged residence time, and slow/incomplete transfer to the circulation, may selectively target IP disease while minimizing organ toxicity. In this study, cohorts of 3-6 patients were treated with $^{131}$I-8H9 at escalated doses from 30 mCi/m$^2$ to 60 mCi/m$^2$ as a single IP injection. A tracer dose of 2 mCi $^{124}$I-8H9 was given IP before $^{131}$I-8H9 to acquire PET images and biodistribution data. Pharmacokinetics (PK) was studied using serial blood draws. 15 heavily prior-treated patients were treated (of which 13 had DSRCT and 2 had rhabdomyosarcoma) received 30, 40, 50 mCi/m$^2$ $^{131}$I-8H9 (3 at each dose level) or 60 mCi/m$^2$ (n=6). Dose limiting toxicity was not seen. Three separate transient, self-limiting, possibly therapy-related grade 3 toxicities were noted in 3 patients, neutropenia, hepatic transaminase elevation and thrombocytopenia, respectively. No patient required hematopoietic stem cell rescue. Blood half life was 32.5±11.5 h (n=12) and mean peritoneal residence time was 14.6 h (n=3). Mean absorbed dose to blood based on blood sampling was 0.56±0.21 rad/mCi (n=14). Mean absorbed doses (rad/mCi) to kidney, liver, lung and spleen were 1.72, 1.92, 0.64 and 1.03, respectively (n=3). Dehalogenation was insignificant: >80% iodine remained protein-bound in blood (n=10). 6/7 DSRCT patients treated without evaluable disease remain in remission at a median of 11.1 months post $^{131}$I-8H9. cRIT using IP $^{131}$I-8H9 was safe and $^{124}$I-8H9 provided valuable PK and dosimetry data. Since maximum tolerated dose was not reached, patient accrual was expanded to treat up to 90 mCi/m$^2$.

Convection Enhanced Delivery (CED) of $^{124}$I-8H9 for Patients with Non-Progressive Diffuse Pontine Gliomas Previously Treated with External Beam Radiation Therapy (Clinicaltrials.gov NCT01502917)

Diffuse pontine glioma (DPG) in childhood is a uniformly lethal condition with a median life expectancy of only 8-10 months from diagnosis. (Dunkel, I. J. et al., 1998, J. Neurooncol. 37:67-73; Kaplan, A. M et al., 1996, Pediatr. Neurosurg. 24:185-92). Despite innovative clinical trials, including hyperfractionated radiotherapy and high dose chemotherapy, the survival of patients with DPG has not changed. CED, also referred to as interstitial infusion, is a mode of local drug delivery that relies on a pressure-dependent gradient to enhance uniform infusate dispersion and volume of distribution. (Laske, D. W. et al., 1997, J. Neurosurg. 87:586-94; Morrison, P. F. et al., 1994, Am. J. Physiol. 266:R292-305). A small-gauge cannula is stereotactically placed in parenchyma or tumor, and infusate is delivered at a slow constant rate. This bypasses the BBB, which poses a natural obstacle to high regional concentration and distribution of systemically administered therapeutics in the brain. In the case of DPG, where the BBB is largely intact, orally or systemically administered anti-cancer therapies have limited CNS penetrance. Preclinical studies have shown that CED of 8H9 in rodent brainstem was safe. (Luther, N. et al., 2008, Neurosurgery 63:1166-74; Occhiogrosso, G. et al., 2003, Neurosurgery 52:388-94; Luther, N. et al., 2014, Neuro. Oncol., in press). Furthermore, intratumoral CED of 8H9 (Luther, N. et al., 2008, Neurosurgery 63:1166-74) or its immunotoxin (8H9-pseudomonas exotoxin) (Luther, N. et al., 2010, Mol. Cancer. Ther. 9:1039-46) in immunoreactive U87 xenografts in rat brain was also found to be safe, with a similar distribution as was found in naïve brain. Finally, $^{124}$I-8H9 was well-tolerated in the rodent as well as primate brain stem following interstitial infusion (Luther, N. et al., 2014, Neuro. Oncol.:in press). By increasing either the dose or volume of antibody infusion, the volume of 8H9 distribution can be increased. $^{124}$I-8H9 is an ideal theranostic agent for dosimetry and therapy. In the phase I clinical trial, patients with DIPG who have undergone external beam radiation therapy as part of standard of care received CED of $^{124}$I-8H9 at 4 dose levels (0.25, 0.5, 0.75, and 1 mCi/injection) with 3-6 patients in each group. At 1 mCi/injection, MTD has not been reached. By PET, $^{124}$I-8H9 showed exquisite tumor localization. There were no complications from the CED, and no significant toxicities (>grade 2) noted. Patients treated at the higher $^{124}$I-8H9 dose levels have survived beyond the historical median time to death. The trial is being amended to continue to dose escalate with 3 additional dose levels (2.5, 3.5, and 4 mCi). CED of radiolabeled 8H9 can be applied to other solitary infiltrative primary or metastatic brain tumors.

EQUIVALENTS AND SCOPE

Those skilled in the art will recognize, or be able to ascertain using no more than routine experimentation, many equivalents to the specific embodiments of the invention, described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein.

The publications discussed above and throughout the text are provided solely for their disclosure prior to the filing date of the present application. Nothing herein is to be construed as an admission that the inventors are not entitled to antedate such disclosure by virtue of prior disclosure.

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

REFERENCES

Mellman I, Coukos G, Dranoff G: Cancer immunotherapy comes of age. Nature 480:480-9, 2011

Topalian S L, Drake C G, Pardoll D M: Targeting the PD-1/B7-H1(PD-L1) pathway to activate anti-tumor immunity. Curr. Opin. Immunol. 24:207-12, 2012

Topalian S L, Hodi F S, Brahmer J R, et al: Safety, Activity, and Immune Correlates of Anti-PD-1 Antibody in Cancer. N. Engl. J. Med., 2012

Brahmer J R, Tykodi S S, Chow L Q, et al: Safety and Activity of Anti-PD-L1 Antibody in Patients with Advanced Cancer. N. Engl. J. Med., 2012

Romagne F, Andre P, Spee P, et al: Preclinical characterization of 1-7F9, a novel human anti-KIR receptor therapeutic antibody that augments natural killer-mediated killing of tumor cells. Blood 114:2667-77, 2009

Godal R, Bachanova V, Gleason M, et al: Natural killer cell killing of acute myelogenous leukemia and acute lymphoblastic leukemia blasts by killer cell immunoglobulin-like receptor-negative natural killer cells after NKG2A and LIR-1 blockade. Biol. Blood Marrow Transplant 16:612-21, 2010

Tarek N, Gallagher M M, Zheng J, et al: Unlicensed natural killer cells dominate neuroblastoma killing in the presence of anti-GD2 monoclonal antibody. J. Clin. Invest. (in press), 2012

Zhao X W, van Beek E M, Schornagel K, et al: CD47-signal regulatory protein-alpha (SIRPalpha) interactions form a barrier for antibody-mediated tumor cell destruction. Proc. Natl. Acad. Sci. U.S.A. 108:18342-7, 2011

Majeti R, Chao M P, Alizadeh A A, et al: CD47 is an adverse prognostic factor and therapeutic antibody target on human acute myeloid leukemia stem cells. Cell 138:286-99, 2009

Chao M P, Alizadeh A A, Tang C, et al: Therapeutic antibody targeting of CD47 eliminates human acute lymphoblastic leukemia. Cancer Res. 71:1374-84, 2011

Chao M P, Jaiswal S, Weissman-Tsukamoto R, et al: Calreticulin is the dominant pro-phagocytic signal on multiple human cancers and is counterbalanced by CD47. Sci. Transl. Med. 2:63ra94, 2010

Chao M P, Alizadeh A A, Tang C, et al: Anti-CD47 antibody synergizes with rituximab to promote phagocytosis and eradicate non-Hodgkin lymphoma. Cell 142:699-713, 2010

Willingham S B, Volkmer J P, Gentles A J, et al: The CD47-signal regulatory protein alpha (SIRPα) interaction is a therapeutic target for human solid tumors. Proc. Natl. Acad. Sci. U.S.A. 109:6662-6667, 2012

Wilcox R A, Ansell S M, Lim M S, et al: The B7 Homologues and their Receptors in Hematologic Malignancies. Eur. J. Haematol., 2012

Chapoval A I, Ni J, Lau J S, et al: B7-H3: a costimulatory molecule for T cell activation and IFN-gamma production. Nat. Immunol. 2:269-74, 2001

Steinberger P, Majdic O, Derdak S V, et al: Molecular characterization of human 4Ig-B7-H3, a member of the B7 family with four Ig-like domains. J. Immunol. 172:2352-9, 2004

Sun M, Richards S, Prasad D V, et al: Characterization of mouse and human B7-H3 genes. J. Immunol. 168:6294-7, 2002

Suh W K, Gajewska B U, Okada H, et al: The B7 family member B7-H3 preferentially down-regulates T helper type 1-mediated immune responses. Nat. Immunol. 4:899-906, 2003

Castriconi R, Dondero A, Augugliaro R, et al: Identification of 4Ig-B7-H3 as a neuroblastoma-associated molecule that exerts a protective role from an NK cell-mediated lysis. Proc. Natl. Acad. Sci. U.S.A. 101:12640-5, 2004

Roth T J, Sheinin Y, Lohse C M, et al: B7-H3 ligand expression by prostate cancer: a novel marker of prognosis and potential target for therapy. Cancer Res. 67:7893-900, 2007

Zang X, Thompson R H, Al-Ahmadie H A, et al: B7-H3 and B7x are highly expressed in human prostate cancer and associated with disease spread and poor outcome. Proc. Natl. Acad. Sci. U.S.A. 104:19458-63, 2007

Crispen P L, Sheinin Y, Roth T J, et al: Tumor cell and tumor vasculature expression of B7-H3 predict survival in clear cell renal cell carcinoma. Clin. Cancer Res. 14:5150-7, 2008

Boorjian S A, Sheinin Y, Crispen P L, et al: T-cell coregulatory molecule expression in urothelial cell carcinoma: clinicopathologic correlations and association with survival. Clin. Cancer Res. 14:4800-8, 2008

Zang X, Sullivan P S, Soslow R A, et al: Tumor associated endothelial expression of B7-H3 predicts survival in ovarian carcinomas. Mod. Pathol. 23:1104-12, 2010

Lemke D, Pfenning P N, Sahm F, et al: Costimulatory protein 4IgB7H3 drives the malignant phenotype of glioblastoma by mediating immune escape and invasiveness. Clin. Cancer Res. 18:105-17, 2012

Wang L, Zhang Q, Chen W, et al: B7-H3 is overexpressed in patients suffering osteosarcoma and associated with tumor aggressiveness and metastasis. PLoS One 8:e70689, 2013

Yamato I, Sho M, Nomi T, et al: Clinical importance of B7-H3 expression in human pancreatic cancer. Br. J. Cancer 101:1709-16, 2009

Gregorio A, Corrias M V, Castriconi R, et al: Small round blue cell tumours: diagnostic and prognostic usefulness of the expression of B7-H3 surface molecule. Histopathology 53:73-80, 2008

Sun X, Vale M, Leung E, et al: Mouse B7-H3 induces antitumor immunity. Gene Ther. 10:1728-34, 2003

Wu C P, Jiang J T, Tan M, et al: Relationship between co-stimulatory molecule B7-H3 expression and gastric carcinoma histology and prognosis. World J. Gastroenterol. 12:457-9, 2006

Loos M, Hedderich D M, Ottenhausen M, et al: Expression of the costimulatory molecule B7-H3 is associated with prolonged survival in human pancreatic cancer. BMC Cancer 9:463, 2009

Hofmeyer K A, Ray A, Zang X: The contrasting role of B7-H3. Proc. Natl. Acad. Sci. U.S.A. 105:10277-8, 2008

Vigdorovich V, Ramagopal U A, Lazar-Molnar E, et al: Structure and T cell inhibition properties of B7 family member, B7-H3. Structure 21:707-17, 2013

Zhou Z, Luther N, Ibrahim G M, et al: B7-H3, a potential therapeutic target, is expressed in diffuse intrinsic pontine glioma. J. Neurooncol. 111:257-64, 2013

Calabro L, Sigalotti L, Fonsatti E, et al: Expression and regulation of B7-H3 immunoregulatory receptor, in human mesothelial and mesothelioma cells: immunotherapeutic implications. J. Cell Physiol. 226:2595-600, 2011

Modak S, Kramer K, Gultekin S H, et al: Monoclonal antibody 8H9 targets a novel cell surface antigen expressed by a wide spectrum of human solid tumors. Cancer Res. 61:4048-54, 2001

Xu H, Cheung I Y, Guo H F, et al: MicroRNA miR-29 modulates expression of immunoinhibitory molecule B7-H3: potential implications for immune based therapy of human solid tumors. Cancer Res. 69:6275-81, 2009

Modak S, Guo H F, Humm J L, et al: Radioimmunotargeting of human rhabdomyosarcoma using monoclonal antibody 8H9. Cancer Biother. Radiopharm. 20:534-46, 2005

Luther N, Cheung N K, Dunkel I J, et al: Intraparenchymal and intratumoral interstitial infusion of anti-glioma monoclonal antibody 8H9. Neurosurgery 63:1166-74; discussion 1174, 2008

Juhl H, Petrella E C, Cheung N K, et al: Additive cytotoxicity of different monoclonal antibody-cobra venom factor conjugates for human neuroblastoma cells Immunobiology 197:444-59, 1997

Onda M, Wang Q C, Guo H F, et al: In vitro and in vivo cytotoxic activities of recombinant immunotoxin 8H9 (Fv)-PE38 against breast cancer, osteosarcoma, and neuroblastoma. Cancer Res. 64:1419-24, 2004

Luther N, Cheung N K, Souliopoulos E P, et al: Interstitial infusion of glioma-targeted recombinant immunotoxin 8H9scFv-PE38. Mol. Cancer Ther. 9:1039-46, 2010

Cheung N K, Guo H F, Modak S, et al: Anti-idiotypic antibody facilitates scFv chimeric immune receptor gene transduction and clonal expansion of human lymphocytes for tumor therapy. Hybrid Hybridomics 22:209-18, 2003

Kramer K, Modak S, Kushner B H, et al: Radioimmunotherapy of metastatic cancer to the central nervous system: Phase I study of intrathecal 131I-8H9. American Association for Cancer Research LB-4 (Presentation), 2007

Kramer K, Kushner B H, Modak S, et al: Effective Intrathecal Radioimmunotherapy-Based Salvage Regimen for Metastatic Central Nervous System (CNS) Neuroblastoma (NB). Presented at the ISPNO 2008, 2008

Kramer K, Kushner B H, Modak S, et al: Compartmental intrathecal radioimmunotherapy: results for treatment for metastatic CNS neuroblastoma. J. Neurooncol. 97:409-18, 2010

Loo D, Alderson R F, Chen F Z, et al: Development of an Fc-enhanced anti-B7-H3 monoclonal antibody with potent antitumor activity. Clin. Cancer Res. 18:3834-45, 2012

Cheung N K, Guo H, Hu J, et al: Humanizing murine IgG3 anti-GD2 antibody m3F8 substantially improves antibody-dependent cell-mediated cytotoxicity while retaining targeting in vivo. Oncolmmunology 1:477-486, 2012

Zhao Q, Feng Y, Zhu Z, et al: Human monoclonal antibody fragments binding to insulin-like growth factors I and II with picomolar affinity. Mol. Cancer Ther. 10:1677-85, 2011

Cheung, I. Y., Farazi, T. A., Ostrovnaya, I., et al: Deep MicroRNA sequencing reveals downregulation of miR-29a in neuroblastoma central nervous system metastasis. Genes, chromosomes & cancer 53:803-814, 2014

Chen, R., Li, L., and Weng, Z.: ZDOCK: an initial-stage protein-docking algorithm. Proteins 52, 80-87, 2003

Sanchez, R., and Sali, A.: Evaluation of comparative protein structure modeling by MODELLER-3. Proteins Suppl. 1:50-58, 1997

Rocchia, W., Sridharan, S., Nicholls, A. et al: Rapid grid-based construction of the molecular surface and the use of induced surface charge to calculate reaction field energies: Applications to the molecular systems and geometric objects. J. Comput. Chem. 23:128-137, 2002

Salacinski, P. R., McLean, C., Sykes, J. E. et al: Iodination of proteins, glycoproteins, and peptides using a solid-phase oxidizing agent, 1,3,4,6-tetrachloro-3 alpha,6 alpha-diphenyl glycoluril (Iodogen). Analytical biochemistry 117:136-146, 1981

Harlow, E., and Lane, D., 1999, Using antibodies: a laboratory manual, Cold Spring Harbor Laboratory Press, Cold Spring Harbor, N.Y.

Ahmed, M., Hu, J., and Cheung, N. K.: Structure Based Refinement of a Humanized Monoclonal Antibody That Targets Tumor Antigen Disialoganglioside GD2. Frontiers in immunology 5:372, 2014

Zhao, Q., Ahmed, M., Tassev, D. V. et al: Affinity maturation of T-cell receptor-like antibodies for Wilms tumor 1 peptide greatly enhances therapeutic potential. Leukemia, 2015

Zhao, Q., Ahmed, M., Guo, H. F., Cheung, I. Y., and Cheung, N. K.: Alteration of Electrostatic Surface Potential Enhances Affinity and Tumor Killing Properties of Anti-ganglioside GD2 Monoclonal Antibody hu3F8. J. Biol. Chem. 290:13017-13027, 2015

Lin, D. Y., Tanaka, Y., Iwasaki, M. et al: The PD-1/PD-L1 complex resembles the antigen-binding Fv domains of antibodies and T cell receptors. Proc. Natl. Acad. Sci. U.S.A. 105:3011-3016, 2008

Lazar-Molnar, E., Yan, Q., Cao, E. et al: Crystal structure of the complex between programmed death-1 (PD-1) and its ligand PD-L2. Proc. Natl. Acad. Sci U.S.A. 105:10483-10488, 2008

Stamper, C. C., Zhang, Y., Tobin, J. F. et al: Crystal structure of the B7-1/CTLA-4 complex that inhibits human immune responses. Nature 410:608-611, 2001

Schwartz, J. C., Zhang, X., Fedorov, A. A. et al: Structural basis for co-stimulation by the human CTLA-4/B7-2 complex. Nature 410:604-608, 2001

Maher E A, Mietz J, Arteaga C L, et al: Brain metastasis: opportunities in basic and translational research. Cancer Res. 69:6015-20, 2009

Grossman S A, Spence A: NCCN clinical practice guidelines for carcinomatous/lymphotous meningitis. Oncology 13:144-152, 1999

Bruno M K, Raizer J: Leptomeningeal metastases from solid tumors (meningeal carcinomatosis). Cancer Treat. Res. 125:31-52, 2005

Gleissner B, Chamberlain M C: Neoplastic meningitis. Lancet Neurol. 5:443-52, 2006

Wasserstrom W R, Glass J P, Posner J B: Diagnosis and treatment of leptomeningeal metastases from solid tumors: experience with 90 patients. Cancer 49:759-72, 1982

Balm M, Hammack J: Leptomeningeal carcinomatosis. Presenting features and prognostic factors. Arch. Neurol. 53:626-32, 1996

Chamberlain M C: Neoplastic meningitis. J. Clin. Oncol. 23:3605-13, 2005

Freilich R J, FRACP, Krol G, et al: Neuroimaging and Cerebrospinal Fluid Cytology in the Diagnosis of Leptomeningeal Metastasis. Annals of Neurology 38:51-57, 1995

Posner J B: Neurologic Complications of Cancer, Comtemporary neurology series. Philadelphia, F. A. Davis Company, 1995

Littman P, Coccia P, Bleyer W A, et al: Central nervous system (CNS) prophylaxis in children with low risk acute lymphoblastic leukemia (ALL). Int. J. Radiat. Oncol. Biol. Phys. 13:1443-9, 1987

Grossman S A, Moynihan T J: Neoplastic meningitis. Neurol. Clin. 9:843-56, 1991

Holm-Nielsen P: Pathogenesis of ascites in peritoneal carcinomatosis. Acta Pathol. Microbiol. Scand. 33:10-21, 1953

Sangisetty S L, Miner T J: Malignant ascites: A review of prognostic factors, pathophysiology and therapeutic measures. World J. Gastrointest. Surg. 4:87-95, 2012

Smith E M, Jayson G C: The current and future management of malignant ascites. Clin. Oncol. (R. Coll. Radiol.) 15:59-72, 2003

Koppe M J, Boerman O C, Oyen W J, et al: Peritoneal carcinomatosis of colorectal origin: incidence and current treatment strategies. Ann. Surg. 243:212-22, 2006

Eskander R N, Tewari K S: Emerging treatment options for management of malignant ascites in patients with ovarian cancer. Int. J. Womens Health 4:395-404, 2012

Saif M W, Siddiqui I A, Sohail M A: Management of ascites due to gastrointestinal malignancy. Ann. Saudi Med. 29:369-77, 2009

Sadeghi B, Arvieux C, Glehen O, et al: Peritoneal carcinomatosis from non-gynecologic malignancies: results of the EVOCAPE 1 multicentric prospective study. Cancer 88:358-63, 2000

Sugarbaker P H, Alderman R, Edwards G, et al: Prospective morbidity and mortality assessment of cytoreductive surgery plus perioperative intraperitoneal chemotherapy to treat peritoneal dissemination of appendiceal mucinous malignancy. Ann. Surg. Oncol. 13:635-44, 2006

Alvarez R D, Huh W K, Khazaeli M B, et al: A Phase I study of combined modality (90)Yttrium-CC49 intraperitoneal radioimmunotherapy for ovarian cancer. Clin. Cancer Res. 8:2806-11, 2002

Verheijen R H, Massuger L F, Benigno B B, et al: Phase III trial of intraperitoneal therapy with yttrium-90-labeled HMFG1 murine monoclonal antibody in patients with epithelial ovarian cancer after a surgically defined complete remission. J. Clin. Oncol. 24:571-8, 2006

Reardon D A, Akabani G, Coleman R E, et al: Salvage radioimmunotherapy with murine iodine-131-labeled antitenascin monoclonal antibody 81C6 for patients with recurrent primary and metastatic malignant brain tumors: phase II study results. J. Clin. Oncol. 24:115-22, 2006

Reardon D A, Zalutsky M R, Akabani G, et al: A pilot study: 131I-antitenascin monoclonal antibody 81c6 to deliver a 44-Gy resection cavity boost. Neuro Oncol. 10:182-9, 2008

Zalutsky M R, Reardon D A, Akabani G, et al: Clinical experience with alpha-particle emitting 211At: treatment of recurrent brain tumor patients with 211At-labeled chimeric antitenascin monoclonal antibody 81C6. J. Nucl. Med. 49:30-8, 2008

Dayson H, Segal M B: Physiology of the CSF and blood-brain barriers. Boca Raton, Fla., CRC Press, 1996, pp 489-523

Spector R, Mock D M: Biotin transport and metabolism in the central nervous system. Neurochem. Res. 13:213-9, 1988

Kramer K, Kushner B, Heller G, et al: Neuroblastoma metastatic to the central nervous system. The Memorial Sloan-kettering Cancer Center Experience and A Literature Review. Cancer 91:1510-9, 2001

Cheung N K, Cheung W, Kushner B H, et al: Murine Anti-GD2 Monoclonal Antibody 3F8 Combined With Granulocyte-Macrophage Colony-Stimulating Factor and 13-Cis-Retinoic Acid in High-Risk Patients With Stage 4 Neuroblastoma in First Remission. J. Clin. Oncol. 30:3264-70, 2012

Caussa L, Hijal T, Michon J, et al: Role of Palliative Radiotherapy in the Management of Metastatic Pediatric Neuroblastoma: A Retrospective Single-Institution Study. Int. J. Radiat. Oncol. Biol. Phys., 2010

Croog V J, Kramer K, Cheung N K, et al: Whole Neuraxis Irradiation to Address Central Nervous System Relapse in High-Risk Neuroblastoma. Int. J. Radiat. Oncol. Biol. Phys., 2010

Kramer K, Humm J L, Souweidane M M, et al: Phase I study of targeted radioimmunotherapy for leptomeningeal cancers using intra-Ommaya 131-I-3F8. J. Clin. Oncol. 25:5465-70, 2007

Kramer K, Kushner B, Modak S, et al: Recurrent Neuroblastoma Metastatic to the Central Nervous System: Is it curable? Advances in Neuroblastoma Research 2014:A-0241, 2014

Kramer K, Kushner B, Modak S, et al: Radionecrosis in Children treated with Conventional Radiation Therapy and Intrathecal Radioimmunotherapy for CNS Neuroblastoma: Is it a Concern? Advances in Neuroblastoma Research 2014:A-0246, 2014

Modak M J, LaQuaglia M, Carrasquillo J A, et al: Intraperitoneal radioimmunotherapy (RIT) for desmoplastic small round cell tumor (DSRCT): Initial results from a phase I trial (clinicaltrials.gov NCT01099644), ASCO Annual Meeting 2013, J. Clin. Oncol., 2013

Dunkel I J, Garvin J H, Jr., Goldman S, et al: High dose chemotherapy with autologous bone marrow rescue for children with diffuse pontine brain stem tumors. Children's Cancer Group. J. Neurooncol. 37:67-73, 1998

Kaplan A M, Albright A L, Zimmerman R A, et al: Brainstem gliomas in children. A Children's Cancer Group review of 119 cases. Pediatr. Neurosurg. 24:185-92, 1996

Laske D W, Morrison P F, Lieberman D M, et al: Chronic interstitial infusion of protein to primate brain: determination of drug distribution and clearance with single-photon emission computerized tomography imaging. J. Neurosurg. 87:586-94, 1997

Morrison P F, Laske D W, Bobo H, et al: High-flow microinfusion: tissue penetration and pharmacodynamics. Am. J. Physiol. 266:R292-305, 1994

Occhiogrosso G, Edgar M A, Sandberg D I, et al: Prolonged convection-enhanced delivery into the rat brainstem. Neurosurgery 52:388-93; discussion 393-4, 2003

Luther N, Zhou Z, Zanzonico P, et al: The potential of theragnostic 124I-8H9 convection-enhanced delivery in diffuse intrinsic pontine glioma. Neuro Oncol.:in press, 2014

Compte, M., Nunez-Prado, N., Sanz, L. & Alvarez-Vallina, L Immunotherapeutic organoids: a new approach to cancer treatment. Biomatter 3, doi:10.4161/biom.23897 (2013).

Noel, D. et al. In vitro and in vivo secretion of cloned antibodies by genetically modified myogenic cells. Hum. Gene Ther. 8:1219-1229, doi:10.1089/hum.1997.8.10-1219 (1997).

Noel, D. et al. High in vivo production of a model monoclonal antibody on adenoviral gene transfer. Hum. Gene Ther. 13:1483-1493, doi:10.1089/10430340260185111 (2002).

Jooss, K. & Chirmule, N. Immunity to adenovirus and adeno-associated viral vectors: implications for gene therapy. Gene Ther. 10:955-963, doi:10.1038/sj.gt.3302037 (2003).

Xiao, P. J., Lentz, T. B. & Samulski, R. J. Recombinant adeno-associated virus: clinical application and development as a gene-therapy vector. Therapeutic delivery 3:835-856 (2012).

Nathwani, A. C. et al. Adenovirus-associated virus vector-mediated gene transfer in hemophilia B. N. Engl. J. Med. 365:2357-2365, doi:10.1056/NEJMoa1108046 (2011).

Patel, N., Reiss, U., Davidoff, A. M. & Nathwani, A. C. Progress towards gene therapy for haemophilia B. International journal of hematology 99:372-376, doi:10.1007/s12185-014-1523-0 (2014).

Fang, J. et al. Stable antibody expression at therapeutic levels using the 2A peptide. Nat. Biotechnol. 23:584-590 (2005).

Watanabe, M., Boyer, J. L. & Crystal, R. G. Genetic delivery of bevacizumab to suppress vascular endothelial growth factor-induced high-permeability pulmonary edema. Hum. Gene Ther. 20:598-610, doi:10.1089/hum.2008.169 (2009).

Ho, D. T. et al. Growth inhibition of an established A431 xenograft tumor by a full-length anti-EGFR antibody following gene delivery by AAV. Cancer Gene Ther. 16:184-194, doi:10.1038/cgt.2008.68 (2009).

Wang, G. et al. Persistent expression of biologically active anti-HER2 antibody by AAVrh.10-mediated gene transfer. Cancer Gene Ther. 17:559-570, doi:10.1038/cgt.2010.11 (2010).

Vigna, E. et al. "Active" cancer immunotherapy by anti-Met antibody gene transfer. Cancer Res. 68:9176-9183, doi: 10.1158/0008-5472.CAN-08-1688 (2008).

Balazs, A. B. et al. Antibody-based protection against HIV infection by vectored immunoprophylaxis. Nature 481: 81-84, doi:10.1038/nature10660 (2012).

Arafat, W. O. et al. Effective single chain antibody (scFv) concentrations in vivo via adenoviral vector mediated expression of secretory scFv. Gene Ther. 9:256-262, doi: 10.1038/sj.gt.3301639 (2002).

Sanz, L., Kristensen, P., Russell, S. J., Ramirez Garcia, J. R. & Alvarez-Vallina, L. Generation and characterization of recombinant human antibodies specific for native laminin epitopes: potential application in cancer therapy. Cancer Immunol. Immunother. 50:557-565 (2001).

Sanz, L. et al. A novel cell binding site in the coiled-coil domain of laminin involved in capillary morphogenesis. Embo J. 22:1508-1517, doi:10.1093/emboj/cdg150 (2003).

Sanz, L. et al. Single-chain antibody-based gene therapy: inhibition of tumor growth by in situ production of phage-derived human antibody fragments blocking functionally active sites of cell-associated matrices. Gene Ther. 9:1049-1053, doi:10.1038/sj.gt.3301725 (2002).

Sanchez-Arevalo Lobo, V. J. et al. Enhanced antiangiogenic therapy with antibody-collagen XVIII NC1 domain fusion proteins engineered to exploit matrix remodeling events. Int. J. Cancer 119:455-462, doi:10.1002/ijc.21851 (2006).

Afanasieva, T. A. et al. Single-chain antibody and its derivatives directed against vascular endothelial growth factor: application for antiangiogenic gene therapy. Gene Ther. 10:1850-1859, doi:10.1038/sj.gt.3302085 (2003).

Liu, X., Wu, J., Zhang, S., Li, C. & Huang, Q. Novel strategies to augment genetically delivered immunotoxin molecular therapy for cancer therapy. Cancer Gene Ther. 16:861-872, doi:10.1038/cgt.2009.30 (2009).

Blanco, B., Holliger, P., Vile, R. G. & Alvarez-Vallina, L. Induction of human T lymphocyte cytotoxicity and inhibition of tumor growth by tumor-specific diabody-based molecules secreted from gene-modified bystander cells. J. Immunol. 171:1070-1077 (2003).

Compte, M. et al. Inhibition of tumor growth in vivo by in situ secretion of bispecific anti-CEAxanti-CD3 diabodies from lentivirally transduced human lymphocytes. Cancer Gene Ther. 14: 380-388, doi:10.1038/sj.cgt.7701021 (2007).

What is claimed is:

1. An antibody agent comprising an immunoglobulin heavy chain and an immunoglobulin light chain, wherein the antibody agent binds specifically to protein 2Ig-B7H3 or 4Ig-B7H3, and wherein said immunoglobulin light chain comprises a sequence as set forth in a SEQ ID NO. selected from the group consisting of SEQ ID NO.: 1, 2, 3, 4, 5, 6, 7 and 8, and said immunoglobulin heavy chain comprises a sequence as set forth in a SEQ ID NO. selected from the group consisting of SEQ ID NO.: 9, 10, 11, 12, 13, 14, 15 and 16.

2. The antibody agent of claim 1, wherein:
   (i) the immunoglobulin light chain is set forth in SEQ ID NO.: 1 and the immunoglobulin heavy chain is set forth in SEQ ID NO.: 9;
   (ii) the immunoglobulin light chain is set forth in SEQ ID NO.: 2 and the immunoglobulin heavy chain is set forth in SEQ ID NO.: 10;
   (iii) the immunoglobulin light chain is set forth in SEQ ID NO.: 3 and the immunoglobulin heavy chain is set forth in SEQ ID NO.: 11;
   (iv) the immunoglobulin light chain is set forth in SEQ ID NO.: 4 and the immunoglobulin heavy chain is set forth in SEQ ID NO.: 12;
   (v) the immunoglobulin light chain is set forth in SEQ ID NO.: 2 and the immunoglobulin heavy chain is set forth in SEQ ID NO.: 11;
   (vi) the immunoglobulin light chain is set forth in SEQ ID NO.: 3 and the immunoglobulin heavy chain is set forth in SEQ ID NO.: 10;
   (vii) the immunoglobulin light chain is set forth in SEQ ID NO.: 5 and the immunoglobulin heavy chain is set forth in SEQ ID NO.: 13;
   (viii) the immunoglobulin light chain is set forth in SEQ ID NO.: 6 and the immunoglobulin heavy chain is set forth in SEQ ID NO.: 14;
   (ix) the immunoglobulin light chain is set forth in SEQ ID NO.: 7 and the immunoglobulin heavy chain is set forth in SEQ ID NO.: 15; or
   (x) the immunoglobulin light chain is set forth in SEQ ID NO.: 8 and the immunoglobulin heavy chain is set forth in SEQ ID NO.: 16.

3. The antibody agent of claim 1, wherein the immunoglobulin light chain is set forth in SEQ ID NO.: 5 and the immunoglobulin heavy chain is set forth in SEQ ID NO.: 13.

4. The antibody agent of claim 1, wherein the immunoglobulin light chain is set forth in SEQ ID NO.: 7 and the immunoglobulin heavy chain is set forth in SEQ ID NO.: 15.

5. The antibody agent of claim 1, wherein the immunoglobulin light chain is fused to a polypeptide set forth in SEQ ID NO.: 30 or SEQ ID NO.: 31.

6. The antibody agent of claim 1, conjugated to a therapeutic agent or detection agent.

7. The antibody agent of claim 6, wherein the antibody is conjugated to a radio-isotope, a drug agent, a nanoparticle, or an immune-toxin.

8. The antibody agent of claim 6, wherein the antibody is conjugated to a diagnostic or imaging agent, or both.

9. The antibody agent of claim 1, wherein the antibody agent is a bispecific antibody.

10. The antibody agent of claim 9, having a first and a second specificity, and wherein the first specificity binds to protein 2Ig-B7H3 or 4Ig-B7H3, and the second specificity binds to CD3 on T cells or 1,4,7,10-tetraazacyclododecane-1,4,7,10-tetraacetic acid (DOTA).

11. An scFv that binds specifically to protein 2Ig-B7H3 or 4Ig-B7H3 and comprising the polypeptide set forth in a SEQ ID NO. selected from the group consisting of SEQ ID NO.: 17, 18, 19, 20, 21, 22, 23, 24, 25, 26 and 27.

12. The scFv of claim 11, wherein the polypeptide is fused to a second polypeptide set forth in SEQ ID NO.: 28 or SEQ ID NO.: 29.

13. The scFv of claim 11, wherein the scFv is conjugated to a therapeutic agent or detection agent.

14. A pharmaceutical composition comprising the antibody agent of claim 1 and a pharmaceutically acceptable carrier.

15. A method of treating cancer, comprising administering to a patient in need thereof a therapeutically effective amount of the antibody agent of claim 1.

16. A method of modulating the immune system, comprising administering to a patient in need thereof a therapeutically effective amount of the antibody agent of claim 1.

17. The method of claim 15, wherein the cancer is or comprises a neuroblastoma.

18. The method of claim 15, wherein the cancer is or comprises a cervical cancer.

19. The method of claim 15, wherein the cancer comprises B7H3-positive tumor cells.

20. A method of enhancing T-cell mediated cytotoxicity in a subject, the method comprising steps of:
   administering to a subject a composition comprising an antibody agent that binds to B7H3's FG-loop, wherein the antibody agent comprises:
   (i) light chain CDR1, CDR2, and CDR3 as set forth in SEQ ID NOs: 34, 36, and 38, respectively, and heavy chain CDR1, CDR2, and CDR3 as set forth in 58, 60, and 62, respectively;
   (ii) light chain CDR1, CDR2, and CDR3 as set forth in SEQ ID NOs: 40, 42, and 44, respectively, and heavy chain CDR1, CDR2, and CDR3 as set forth in 64, 66, and 68, respectively;
   (iii) light chain CDR1, CDR2, and CDR3 as set forth in SEQ ID NOs: 46, 48, and 50, respectively, and heavy chain CDR1, CDR2, and CDR3 as set forth in 70, 72, and 74, respectively; or
   (iv) light chain CDR1, CDR2, and CDR3 as set forth in SEQ ID NOs: 52, 54, and 56, respectively, and heavy chain CDR1, CDR2, and CDR3 as set forth in 76, 78, and 80, respectively.

21. The method of claim 20, wherein the antibody agent comprises an immunoglobulin heavy chain and an immunoglobulin light chain, wherein said immunoglobulin heavy chain comprises a sequence as set forth in SEQ ID NO: 13 or 15, and said immunoglobulin light chain comprises a sequence as set forth in SEQ ID NO: 5 or 7.

22. A DNA or RNA encoding an antibody agent claim 1.

23. A cell that expresses an antibody agent of claim 1.

24. A method of preparing a cell that expresses an antibody agent, comprising transfecting or virally transducing a cell with the DNA of claim 22.

25. A method of treating a patient by compartmental radioimmunotherapy (cRIT), comprising administering an antibody agent of claim 1 to a patient in need thereof.

26. The method of claim 25, wherein the antibody is administered intrathecally, intraperitoneally, or by convection enhanced delivery.

\* \* \* \* \*